(12) United States Patent
Yun et al.

(10) Patent No.: US 8,115,919 B2
(45) Date of Patent: Feb. 14, 2012

(54) METHODS, ARRANGEMENTS AND SYSTEMS FOR OBTAINING INFORMATION ASSOCIATED WITH A SAMPLE USING OPTICAL MICROSCOPY

(75) Inventors: Seok-Hyun Yun, Cambridge, MA (US); Giuliano Scarcelli, Boston, MA (US)

(73) Assignee: The General Hospital Corporation, Boston, MA (US)

( * ) Notice: Subject to any disclaimer, the term of this patent is extended or adjusted under 35 U.S.C. 154(b) by 957 days.

(21) Appl. No.: 12/114,081

(22) Filed: May 2, 2008

(65) Prior Publication Data
US 2009/0323056 A1 Dec. 31, 2009

Related U.S. Application Data

(60) Provisional application No. 60/915,990, filed on May 4, 2007.

(51) Int. Cl.
*G01J 3/44* (2006.01)
(52) U.S. Cl. .......................................... 356/301
(58) Field of Classification Search ................... 356/301, 356/72–73, 326
See application file for complete search history.

(56) References Cited

U.S. PATENT DOCUMENTS

| | | |
|---|---|---|
| 2,339,754 A | 1/1944 | Brace |
| 3,090,753 A | 5/1963 | Matuszak et al. |
| 3,601,480 A | 8/1971 | Randall |
| 3,856,000 A | 12/1974 | Chikama |
| 3,872,407 A | 3/1975 | Hughes |
| 3,941,121 A | 3/1976 | Olinger |
| 3,973,219 A | 8/1976 | Tang et al. |
| 3,983,507 A | 9/1976 | Tang et al. |
| 4,030,827 A | 6/1977 | Delhaye et al. |

(Continued)

FOREIGN PATENT DOCUMENTS
DE 4105221 9/1991
(Continued)

OTHER PUBLICATIONS

Fujimoto et al., "High Resolution in Vivo Intra-Arterial Imaging with Optical Coherence Tomography," *Official Journal of the British Cardiac Society*, vol. 82, pp. 128-133 Heart, 1999.

(Continued)

*Primary Examiner* — Tarifur Chowdhury
*Assistant Examiner* — Abdullahi Nur
(74) *Attorney, Agent, or Firm* — Dorsey & Whitney LLP

(57) ABSTRACT

Exemplary embodiments of methods, arrangements and systems for obtaining information about a sample can be provided. For example, in one exemplary embodiment, it is possible to receive a first electro-magnetic radiation from a sample which is based on a second electro-magnetic radiation forwarded to the sample. The first electro-magnetic radiation may have a first frequency and the second electro-magnetic radiation may have a second frequency which is different from the first frequency. The difference between the first and second frequencies can be based on an acoustic wave inside the sample related to at least one characteristic of the sample. Further, it is possible to receive at least a portion of the first electromagnetic radiation and separate it into a particular finite number (N) of frequency component radiations. In addition, it is possible to receive a particular energy of more than 1/N of energy of the third electro-magnetic radiation, and generate information associated with the sample. Certain exemplary embodiments of the present invention are capable of obtaining information associated with a sample, particularly its mechanical properties, non-contact using electromagnetic radiation.

30 Claims, 9 Drawing Sheets

U.S. PATENT DOCUMENTS

| | | | |
|---|---|---|---|
| 4,140,364 A | 2/1979 | Yamashita et al. | |
| 4,141,362 A | 2/1979 | Wurster | |
| 4,224,929 A | 9/1980 | Furihata | |
| 4,295,738 A | 10/1981 | Meltz et al. | |
| 4,300,816 A | 11/1981 | Snitzer et al. | |
| 4,303,300 A | 12/1981 | Pressiat et al. | |
| 4,428,643 A | 1/1984 | Kay | |
| 4,479,499 A | 10/1984 | Alfano | |
| 4,533,247 A | 8/1985 | Epworth | |
| 4,585,349 A | 4/1986 | Gross et al. | |
| 4,601,036 A | 7/1986 | Faxvog et al. | |
| 4,607,622 A | 8/1986 | Fritch et al. | |
| 4,631,498 A | 12/1986 | Cutler | |
| 4,650,327 A | 3/1987 | Ogi | |
| 4,744,656 A | 5/1988 | Moran et al. | |
| 4,751,706 A | 6/1988 | Rohde et al. | |
| 4,770,492 A | 9/1988 | Levin et al. | |
| 4,834,111 A | 5/1989 | Khanna et al. | |
| 4,868,834 A | 9/1989 | Fox et al. | |
| 4,890,901 A | 1/1990 | Cross, Jr. | |
| 4,892,406 A | 1/1990 | Waters | |
| 4,909,631 A | 3/1990 | Tan et al. | |
| 4,925,302 A | 5/1990 | Cutler | |
| 4,928,005 A | 5/1990 | Lefèvre et al. | |
| 4,965,441 A | 10/1990 | Picard | |
| 4,965,599 A | 10/1990 | Roddy et al. | |
| 4,993,834 A | 2/1991 | Carlhoff et al. | |
| 5,039,193 A | 8/1991 | Snow et al. | |
| 5,040,889 A | 8/1991 | Keane | |
| 5,045,936 A | 9/1991 | Lobb et al. | |
| 5,046,501 A | 9/1991 | Crilly | |
| 5,065,331 A | 11/1991 | Vachon et al. | |
| 5,085,496 A | 2/1992 | Yoshida et al. | |
| 5,120,953 A | 6/1992 | Harris | |
| 5,121,983 A | 6/1992 | Lee | |
| 5,127,730 A | 7/1992 | Brelje et al. | |
| 5,197,470 A | 3/1993 | Helfer et al. | |
| 5,202,745 A | 4/1993 | Sorin et al. | |
| 5,212,667 A | 5/1993 | Tomlinson et al. | |
| 5,214,538 A | 5/1993 | Lobb | |
| 5,228,001 A | 7/1993 | Birge et al. | |
| 5,248,876 A | 9/1993 | Kerstens et al. | |
| 5,262,644 A | 11/1993 | Maguire | |
| 5,291,885 A | 3/1994 | Taniji et al. | |
| 5,293,872 A | 3/1994 | Alfano et al. | |
| 5,293,873 A | 3/1994 | Fang | |
| 5,304,173 A | 4/1994 | Kittrell et al. | |
| 5,304,810 A | 4/1994 | Amos | |
| 5,305,759 A | 4/1994 | Kaneko et al. | |
| 5,317,389 A | 5/1994 | Hochberg et al. | |
| 5,318,024 A | 6/1994 | Kittrell et al. | |
| 5,321,501 A | 6/1994 | Swanson et al. | |
| 5,353,790 A | 10/1994 | Jacques et al. | |
| 5,383,467 A | 1/1995 | Auer et al. | |
| 5,411,016 A | 5/1995 | Kume et al. | |
| 5,419,323 A | 5/1995 | Kittrell et al. | |
| 5,439,000 A | 8/1995 | Gunderson et al. | |
| 5,441,053 A | 8/1995 | Lodder et al. | |
| 5,450,203 A | 9/1995 | Penkethman | |
| 5,454,807 A | 10/1995 | Lennox et al. | |
| 5,459,325 A | 10/1995 | Hueton et al. | |
| 5,459,570 A | 10/1995 | Swanson et al. | |
| 5,465,147 A | 11/1995 | Swanson | |
| 5,486,701 A | 1/1996 | Norton et al. | |
| 5,491,524 A | 2/1996 | Hellmuth et al. | |
| 5,491,552 A | 2/1996 | Kittrell | |
| 5,526,338 A | 6/1996 | Hasman et al. | |
| 5,562,100 A | 10/1996 | Kittrell et al. | |
| 5,565,986 A | 10/1996 | Knüttel | |
| 5,583,342 A | 12/1996 | Ichie | |
| 5,590,660 A | 1/1997 | MacAulay et al. | |
| 5,600,486 A | 2/1997 | Gal et al. | |
| 5,601,087 A | 2/1997 | Gunderson et al. | |
| 5,621,830 A | 4/1997 | Lucey et al. | |
| 5,623,336 A | 4/1997 | Raab et al. | |
| 5,635,830 A | 6/1997 | Itoh | |
| 5,649,924 A | 7/1997 | Everett et al. | |
| 5,697,373 A | 12/1997 | Richards-Kortum et al. | |
| 5,698,397 A | 12/1997 | Zarling et al. | |
| 5,710,630 A | 1/1998 | Essenpreis et al. | |
| 5,716,324 A | 2/1998 | Toida | |
| 5,719,399 A | 2/1998 | Alfano et al. | |
| 5,735,276 A | 4/1998 | Lemelson | |
| 5,740,808 A | 4/1998 | Panescu et al. | |
| 5,748,318 A | 5/1998 | Maris et al. | |
| 5,748,598 A | 5/1998 | Swanson et al. | |
| 5,784,352 A | 7/1998 | Swanson et al. | |
| 5,785,651 A | 7/1998 | Kuhn et al. | |
| 5,795,295 A | 8/1998 | Hellmuth et al. | |
| 5,801,826 A | 9/1998 | Williams | |
| 5,803,082 A | 9/1998 | Stapleton et al. | |
| 5,807,261 A | 9/1998 | Benaron et al. | |
| 5,817,144 A | 10/1998 | Gregory | |
| 5,840,023 A | 11/1998 | Oraevsky et al. | |
| 5,840,075 A | 11/1998 | Mueller et al. | |
| 5,842,995 A | 12/1998 | Mahadevan-Jansen et al. | |
| 5,843,000 A | 12/1998 | Nishioka et al. | |
| 5,843,052 A | 12/1998 | Benja-Athon | |
| 5,847,827 A | 12/1998 | Fercher | |
| 5,862,273 A | 1/1999 | Pelletier | |
| 5,865,754 A | 2/1999 | Sevick-Muraca et al. | |
| 5,867,268 A | 2/1999 | Gelikonov et al. | |
| 5,871,449 A | 2/1999 | Brown | |
| 5,872,879 A | 2/1999 | Hamm | |
| 5,877,856 A | 3/1999 | Fercher | |
| 5,887,009 A | 3/1999 | Mandella et al. | |
| 5,892,583 A | 4/1999 | Li | |
| 5,912,764 A | 6/1999 | Togino | |
| 5,920,373 A | 7/1999 | Bille | |
| 5,920,390 A | 7/1999 | Farahi et al. | |
| 5,921,926 A | 7/1999 | Rolland et al. | |
| 5,926,592 A | 7/1999 | Martin et al. | |
| 5,949,929 A | 9/1999 | Hamm | |
| 5,951,482 A | 9/1999 | Winston et al. | |
| 5,955,737 A | 9/1999 | Hallidy et al. | |
| 5,956,355 A | 9/1999 | Swanson et al. | |
| 5,968,064 A | 10/1999 | Selmon et al. | |
| 5,983,125 A | 11/1999 | Alfano et al. | |
| 5,987,346 A | 11/1999 | Benaron et al. | |
| 5,991,697 A | 11/1999 | Nelson et al. | |
| 5,994,690 A | 11/1999 | Kulkarni et al. | |
| 6,002,480 A | 12/1999 | Izatt et al. | |
| 6,004,314 A | 12/1999 | Wei et al. | |
| 6,006,128 A | 12/1999 | Izatt et al. | |
| 6,010,449 A | 1/2000 | Selmon et al. | |
| 6,014,214 A | 1/2000 | Li | |
| 6,020,963 A | 2/2000 | Dimarzio et al. | |
| 6,033,721 A | 3/2000 | Nassuphis | |
| 6,044,288 A | 3/2000 | Wake et al. | |
| 6,045,511 A | 4/2000 | Lutz et al. | |
| 6,048,742 A | 4/2000 | Weyburne et al. | |
| 6,053,613 A | 4/2000 | Wei et al. | |
| 6,069,698 A | 5/2000 | Ozawa et al. | |
| 6,091,496 A | 7/2000 | Hill | |
| 6,091,984 A | 7/2000 | Perelman et al. | |
| 6,111,645 A | 8/2000 | Tearney et al. | |
| 6,117,128 A | 9/2000 | Gregory | |
| 6,120,516 A | 9/2000 | Selmon et al. | |
| 6,134,003 A | 10/2000 | Tearney et al. | |
| 6,134,010 A | 10/2000 | Zavislan | |
| 6,134,033 A | 10/2000 | Bergano et al. | |
| 6,141,577 A | 10/2000 | Rolland et al. | |
| 6,151,522 A | 11/2000 | Alfano et al. | |
| 6,159,445 A | 12/2000 | Klaveness et al. | |
| 6,160,826 A | 12/2000 | Swanson et al. | |
| 6,161,031 A | 12/2000 | Hochman et al. | |
| 6,166,373 A | 12/2000 | Mao | |
| 6,174,291 B1 | 1/2001 | McMahon et al. | |
| 6,175,669 B1 | 1/2001 | Colston et al. | |
| 6,185,271 B1 | 2/2001 | Kinsinger | |
| 6,191,862 B1 | 2/2001 | Swanson et al. | |
| 6,193,676 B1 | 2/2001 | Winston et al. | |
| 6,198,956 B1 | 3/2001 | Dunne | |
| 6,201,989 B1 | 3/2001 | Whitehead et al. | |
| 6,208,415 B1 | 3/2001 | De Boer et al. | |
| 6,208,887 B1 | 3/2001 | Clarke | |
| 6,245,026 B1 | 6/2001 | Campbell et al. | |

| | | |
|---|---|---|
| 6,249,349 B1 | 6/2001 | Lauer |
| 6,263,234 B1 | 7/2001 | Engelhardt et al. |
| 6,264,610 B1 | 7/2001 | Zhu |
| 6,272,376 B1 | 8/2001 | Marcu et al. |
| 6,274,871 B1 | 8/2001 | Dukor et al. |
| 6,282,011 B1 | 8/2001 | Tearney et al. |
| 6,297,018 B1 | 10/2001 | French et al. |
| 6,308,092 B1 | 10/2001 | Hoyns |
| 6,324,419 B1 | 11/2001 | Guzelsu et al. |
| 6,341,036 B1 | 1/2002 | Tearney et al. |
| 6,353,693 B1 | 3/2002 | Kano et al. |
| 6,359,692 B1 | 3/2002 | Groot |
| 6,377,349 B1 | 4/2002 | Fercher |
| 6,384,915 B1 | 5/2002 | Everett et al. |
| 6,393,312 B1 | 5/2002 | Hoyns |
| 6,394,964 B1 | 5/2002 | Sievert, Jr. et al. |
| 6,396,941 B1 | 5/2002 | Bacus et al. |
| 6,421,164 B2 | 7/2002 | Tearney et al. |
| 6,445,485 B1 | 9/2002 | Frigo et al. |
| 6,445,944 B1 | 9/2002 | Ostrovsky |
| 6,459,487 B1 | 10/2002 | Chen et al. |
| 6,463,313 B1 | 10/2002 | Winston et al. |
| 6,469,846 B2 | 10/2002 | Ebizuka et al. |
| 6,475,159 B1 | 11/2002 | Casscells et al. |
| 6,475,210 B1 | 11/2002 | Phelps et al. |
| 6,485,413 B1 | 11/2002 | Boppart et al. |
| 6,485,482 B1 | 11/2002 | Belef |
| 6,501,551 B1 | 12/2002 | Tearney et al. |
| 6,501,878 B2 | 12/2002 | Hughes et al. |
| 6,538,817 B1 | 3/2003 | Farmer et al. |
| 6,549,801 B1 | 4/2003 | Chen et al. |
| 6,552,796 B2 | 4/2003 | Magnin et al. |
| 6,556,305 B1 | 4/2003 | Aziz et al. |
| 6,556,853 B1 | 4/2003 | Cabib et al. |
| 6,558,324 B1 | 5/2003 | Von Behren et al. |
| 6,564,087 B1 | 5/2003 | Pitris et al. |
| 6,564,089 B2 | 5/2003 | Izatt et al. |
| 6,567,585 B2 | 5/2003 | Martin et al. |
| 6,615,071 B1 | 9/2003 | Casscells, III et al. |
| 6,622,732 B2 | 9/2003 | Constantz |
| 6,680,780 B1 | 1/2004 | Fee |
| 6,685,885 B2 | 2/2004 | Nolte et al. |
| 6,687,007 B1 | 2/2004 | Meigs |
| 6,687,010 B1 | 2/2004 | Horii et al. |
| 6,687,036 B2 | 2/2004 | Riza |
| 6,701,181 B2 | 3/2004 | Tang et al. |
| 6,738,144 B1 | 5/2004 | Dogariu et al. |
| 6,741,355 B2 | 5/2004 | Drabarek |
| 6,790,175 B1 | 9/2004 | Furusawa et al. |
| 6,806,963 B1 | 10/2004 | Wälti et al. |
| 6,816,743 B2 | 11/2004 | Moreno et al. |
| 6,839,496 B1 | 1/2005 | Mills et al. |
| 6,903,820 B2 | 6/2005 | Wang |
| 6,949,072 B2 | 9/2005 | Furnish et al. |
| 6,980,299 B1 | 12/2005 | de Boer |
| 7,006,231 B2 | 2/2006 | Ostrovsky et al. |
| 7,061,622 B2 | 6/2006 | Rollins et al. |
| 7,190,464 B2 | 3/2007 | Alphonse |
| 7,231,243 B2 | 6/2007 | Tearney et al. |
| 7,242,480 B2 | 7/2007 | Alphonse |
| 7,267,494 B2 | 9/2007 | Hongyu et al. |
| 7,355,716 B2 | 4/2008 | De Boer et al. |
| 7,359,062 B2 | 4/2008 | Chen et al. |
| 7,366,376 B2 | 4/2008 | Shishkov et al. |
| 7,391,520 B2 | 6/2008 | Zhou et al. |
| 2001/0047137 A1 | 11/2001 | Moreno et al. |
| 2002/0016533 A1 | 2/2002 | Marchitto et al. |
| 2002/0052547 A1 | 5/2002 | Toida |
| 2002/0064341 A1 | 5/2002 | Fauver et al. |
| 2002/0076152 A1 | 6/2002 | Hughes et al. |
| 2002/0085209 A1 | 7/2002 | Mittleman et al. |
| 2002/0093662 A1 | 7/2002 | Chen et al. |
| 2002/0122246 A1 | 9/2002 | Tearney et al. |
| 2002/0133065 A1* | 9/2002 | Lucassen et al. ............ 600/322 |
| 2002/0140942 A1 | 10/2002 | Fee et al. |
| 2002/0158211 A1 | 10/2002 | Gillispie |
| 2002/0161357 A1 | 10/2002 | Rox et al. |
| 2002/0163622 A1 | 11/2002 | Magnin et al. |
| 2002/0172485 A1 | 11/2002 | Keaton et al. |
| 2002/0183623 A1 | 12/2002 | Tang et al. |
| 2002/0188204 A1 | 12/2002 | McNamara et al. |
| 2002/0196446 A1 | 12/2002 | Roth et al. |
| 2002/0198457 A1 | 12/2002 | Tearney et al. |
| 2003/0023153 A1 | 1/2003 | Izatt et al. |
| 2003/0026735 A1 | 2/2003 | Nolte et al. |
| 2003/0028114 A1 | 2/2003 | Casscells, III et al. |
| 2003/0082105 A1 | 5/2003 | Fischman et al. |
| 2003/0097048 A1 | 5/2003 | Ryan et al. |
| 2003/0108911 A1 | 6/2003 | Klimant et al. |
| 2003/0135101 A1 | 7/2003 | Webler |
| 2003/0164952 A1 | 9/2003 | Deichmann et al. |
| 2003/0171691 A1 | 9/2003 | Casscells, III et al. |
| 2003/0199769 A1 | 10/2003 | Podoleanu et al. |
| 2003/0216719 A1 | 11/2003 | Debenedictis et al. |
| 2003/0220749 A1 | 11/2003 | Chen et al. |
| 2003/0236443 A1 | 12/2003 | Cespedes et al. |
| 2004/0002650 A1 | 1/2004 | Mandrusov et al. |
| 2004/0054268 A1 | 3/2004 | Esenaliev et al. |
| 2004/0072200 A1 | 4/2004 | Rigler et al. |
| 2004/0077949 A1 | 4/2004 | Blofgett et al. |
| 2004/0086245 A1 | 5/2004 | Farroni et al. |
| 2004/0100631 A1 | 5/2004 | Bashkansky et al. |
| 2004/0100681 A1 | 5/2004 | Bjarklev et al. |
| 2004/0126048 A1 | 7/2004 | Dave et al. |
| 2004/0133191 A1 | 7/2004 | Momiuchi et al. |
| 2004/0150829 A1 | 8/2004 | Koch et al. |
| 2004/0152989 A1 | 8/2004 | Puttappa et al. |
| 2004/0166593 A1 | 8/2004 | Nolte et al. |
| 2004/0212808 A1 | 10/2004 | Okawa et al. |
| 2004/0239938 A1 | 12/2004 | Izatt |
| 2004/0263843 A1 | 12/2004 | Knopp et al. |
| 2005/0018201 A1 | 1/2005 | De Boer |
| 2005/0035295 A1 | 2/2005 | Bouma et al. |
| 2005/0046837 A1 | 3/2005 | Izumi et al. |
| 2005/0075547 A1 | 4/2005 | Wang |
| 2005/0083534 A1 | 4/2005 | Riza et al. |
| 2005/0165303 A1 | 7/2005 | Kleen et al. |
| 2005/0171438 A1 | 8/2005 | Chen et al. |
| 2006/0103850 A1 | 5/2006 | Alphonse et al. |
| 2006/0146339 A1 | 7/2006 | Fujita et al. |
| 2006/0155193 A1 | 7/2006 | Leonardi et al. |
| 2006/0244973 A1 | 11/2006 | Yun et al. |
| 2007/0019208 A1 | 1/2007 | Toida et al. |
| 2007/0276242 A1* | 11/2007 | Konofagou ................ 600/437 |
| 2007/0291277 A1 | 12/2007 | Everett et al. |

FOREIGN PATENT DOCUMENTS

| | | |
|---|---|---|
| DE | 4309056 | 9/1994 |
| DE | 19542955 | 5/1997 |
| DE | 10351319 | 6/2005 |
| EP | 0110201 | 6/1984 |
| EP | 0251062 | 1/1988 |
| EP | 0617286 | 2/1994 |
| EP | 0590268 | 4/1994 |
| EP | 0728440 | 8/1996 |
| EP | 0933096 | 8/1999 |
| EP | 1324051 | 7/2003 |
| EP | 1426799 | 6/2004 |
| GB | 1257778 | 12/1971 |
| GB | 2030313 | 4/1980 |
| GB | 2209221 | 5/1989 |
| JP | 4135550 | 5/1992 |
| JP | 4135551 | 5/1992 |
| WO | 7900841 | 10/1979 |
| WO | 9216865 | 10/1992 |
| WO | 9219930 | 11/1992 |
| WO | 9303672 | 3/1993 |
| WO | 9533971 | 12/1995 |
| WO | 9628212 | 9/1996 |
| WO | 9732182 | 9/1997 |
| WO | 9800057 | 1/1998 |
| WO | 9801074 | 1/1998 |
| WO | 9814132 | 4/1998 |
| WO | 9835203 | 8/1998 |
| WO | 9838907 | 9/1998 |
| WO | 9846123 | 10/1998 |
| WO | 9848838 | 11/1998 |
| WO | 9848846 | 11/1998 |

| | | |
|---|---|---|
| WO | 9905487 | 2/1999 |
| WO | 9944089 | 9/1999 |
| WO | 9957507 | 11/1999 |
| WO | 0058766 | 10/2000 |
| WO | 0108579 | 2/2001 |
| WO | 0127679 | 4/2001 |
| WO | 0138820 | 5/2001 |
| WO | 0142735 | 6/2001 |
| WO | 0236015 | 5/2002 |
| WO | 0238040 | 5/2002 |
| WO | 0254027 | 7/2002 |
| WO | 02084263 | 10/2002 |
| WO | 03020119 | 3/2003 |
| WO | 03046636 | 6/2003 |
| WO | 03052478 | 6/2003 |
| WO | 03062802 | 7/2003 |
| WO | 03105678 | 12/2003 |
| WO | 2004034869 | 4/2004 |
| WO | 2004057266 | 7/2004 |
| WO | 2004066824 | 8/2004 |
| WO | 2004088361 | 10/2004 |
| WO | 2004105598 | 12/2004 |
| WO | 2005000115 | 1/2005 |
| WO | 2005054780 | 6/2005 |
| WO | 2005082225 | 9/2005 |
| WO | 2006014392 | 2/2006 |
| WO | 2006039091 | 4/2006 |
| WO | 2006059109 | 6/2006 |
| WO | 2006130797 | 12/2006 |
| WO | 2007028531 | 3/2007 |
| WO | 2007038787 | 4/2007 |
| WO | 2007083138 | 7/2007 |

OTHER PUBLICATIONS

D. Huang et al., "Optical Coherence Tomography," *SCIENCE*, vol. 254, pp. 1178-1181, Nov. 1991.
Tearney et al., "High-Speed Phase -and Group Delay Scanning with a Grating Based Phase Control Delay Line," *Optics Letters*, vol. 22, pp. 1811-1813, Dec. 1997.
Rollins, et al., "In Vivo Video Rate Optical Coherence Tomography," *Optics Express*, vol. 3, pp. 219-229, Sep. 1998.
Saxer, et al., High Speed Fiber-Based Polarization-Sensitive Optical Coherence Tomography of in Vivo Human Skin, *Optical Society of America*, vol. 25, pp. 1355-1357, Sep. 2000.
Oscar Eduardo Martinez, "3000 Times Grating Compress or with Positive Group Velocity Dispersion," *IEEE*, vol. QE-23, pp. 59-64, Jan. 1987.
Kulkarni, et al., "Image Enhancement in Optical Coherence Tomography Using Deconvolution," *Electric Letters*, vol. 33, pp. 1365-1367, Jul. 1997.
Bashkansky, et al., "Signal Processing for Improving Field Cross-Correlation Function in Optical Coherence Tomography," *Optics & Photonics News*, vol. 9, pp. 8137-8138, May 1998.
Yung et al., "Phase-Domain Processing of Optical Coherence Tomography Images," *Journal of Biomedical Optics*, vol. 4, pp. 125-136, Jan. 1999.
Tearney, et al., "In Vivo Endoscopic Optical Biopsy with Optical Coherence Tomography," *SCIENCE*, vol. 276, Jun. 1997.
W. Drexler et al., "In Vivo Ultrahigh-Resolution Optical Coherence Tomography," *Optics Letters* vol. 24, pp. 1221-1223, Sep. 1999.
Nicusor V. Iftimia et al., "A Portable, Low Coherence Interferometry Based Instrument for Fine Needle Aspiration Biopsy Guidance," Accepted to Review of Scientific Instruments, 2005.
Abbas, G.L., V.W.S. Chan et al., "Local-Oscillator Excess-Noise Suppression for Homodyne and Heterodyne-Detection," *Optics Letters*, vol. 8, pp. 419-421, Aug. 1983.
Agrawal, G.P., "Population Pulsations and Nondegenerate 4-Wave Mixing in Semiconductor-Lasers and Amplifiers," *Journal of the Optical Society of America B-Optical Physics*, vol. 5, pp. 147-159, Jan. 1998.
Andretzky, P. et al., "Optical Coherence Tomography by Spectral Radar: Improvement of Signal-to-Noise Ratio," *The International Society for Optical Engineering, USA*, vol. 3915, 2000.

Ballif, J. et al., "Rapid and Scalable Scans at 21 m/s in optical Low-Coherence Reflectometry," *Optics Letters*, vol. 22, pp. 757-759, Jun. 1997.
Barfuss H. et al., "Modified Optical Frequency-Domain Reflectometry with High Spatial-Resolution for Components of Integrated Optic Systems," *Journal of Lightwave Technology*, vol. 7, pp. 3-10, Jan. 1989.
Beaud, P. et al., "Optical Reflectometry with Micrometer Resolution for the Investigation of Integrated Optical-Devices," *Leee Journal of Quantum Electronics*, vol. 25, pp. 755-759, Apr. 1989.
Bouma, Brett et al., "Power-Efficient Nonreciprocal Interferometer and Linear-Scanning Fiber-Optic Catheter for Optical Coherence Tomography," *Optics Letters*, vol. 24, pp. 531-533, Apr. 1999.
Brinkmeyer, E. et al., "Efficient Algorithm for Non-Equidistant Interpolation of Sampled Data," *Electronics Letters*, vol. 28, p. 693, Mar. 1992.
Brinkmeyer, E. et al., "High-Resolution OCDR in Dispersive Wave-Guides," *Electronics Letters*, vol. 26, pp. 413-414, Mar. 1990.
Chinn, S.R. et al., "Optical Coherence Tomography Using a Frequency-Tunable Optical Source," *Optics Letters*, vol. 22, pp. 340-342, Mar. 1997.
Danielson, B.L. et al., "Absolute Optical Ranging Using Low Coherence Interferometry," *Applied Optics*, vol. 30, pp. 2975, Jul. 1991.
Dorrer, C. et al., "Spectral Resolution and Sampling Issues in Fourier-Transform Spectral Interferometry," *Journal of the Optical Society of America B-Optical Physics*, vol. 17, pp. 1795-1802, Oct. 2000.
Dudley, J.M. et al., "Cross-Correlation Frequency Resolved Optical Gating Analysis of Broadband Continuum Generation in Photonic Crystal Fiber: Simulations and Experiments," *Optics Express*, vol. 10, p. 1215, Oct. 2002.
Eickhoff, W. et al., "Optical Frequency-Domain Reflectometry in Single-Mode Fiber," *Applied Physics Letters*, vol. 39, pp. 693-695, 1981.
Fercher, Adolf "Optical Coherence Tomography," *Journal of Biomedical Optics*, vol. 1, pp. 157-173, Apr. 1996.
Ferreira, L.A. et al., "Polarization-Insensitive Fiberoptic White-Light Interferometry," *Optics Communications*, vol. 114, pp. 386-392, Feb. 1995.
Fujii, Yohji, "High-Isolation Polarization-Independent Optical Circulator", *Journal of Lightwave Technology*, vol. 9, pp. 1239-1243, Oct. 1991.
Glance, B., "Polarization Independent Coherent Optical Receiver," *Journal of Lightwave Technology*, vol. LT-5, p. 274, Feb. 1987.
Glombitza, U., "Coherent Frequency-Domain Reflectometry for Characterization of Single-Mode Integrated-Optical Wave-Guides," *Journal of Lightwave Technology*, vol. 11, pp. 1377-1384, Aug. 1993.
Golubovic, B. et al., "Optical Frequency-Domain Reflectometry Using Rapid Wavelength Tuning of a Cr4+:Forsterite Laser," *Optics Letters*, vol. 11, pp. 1704-1706, Nov. 1997.
Haberland, U. H. P. et al., "Chirp Optical Coherence Tomography of Layered Scattering Media," *Journal of Biomedical Optics*, vol. 3, pp. 259-266, Jul. 1998.
Hammer, Daniel X. et al., "Spectrally Resolved White-Light Interferometry for Measurement of Ocular Dispersion," *Journal of the Optical Society of America A-Optics Image Science and Vision*, vol. 16, pp. 2092-2102, Sep. 1999.
Harvey, K. C. et al., "External-Cavity Diode-Laser Using a Grazing-Incidence Diffraction Grating," *Optics Letters*, vol. 16, pp. 910-912, Jun. 1991.
Hausler, Gerd et al., "'Coherence Radar' and 'Spectral Radar' New Tools for Dermatological Diagnosis," *Journal of Biomedical Optics*, vol. 3, pp. 21-31, Jan. 1998.
Hee, Michael R. et al., "Polarization-Sensitive Low-Coherence Reflectometer for Birefringence Characterization and Ranging," *Journal of the Optical Society of America B(Optical Physics)*, vol. 9, p. 903-908, Jun. 1992.
Hotate Kazuo et al., "Optical Coherence Domain Reflectometry by Synthesis of Coherence Function," *Journal of Lightwave Technology*, vol. 11, pp. 1701-1710, Oct. 1993.
Inoue, Kyo et al., "Nearly Degenerate 4-Wave-Mixing in a Traveling-Wave Semiconductor-Laser Amplifier," *Applied Physics Letters*, vol. 51, pp. 1051-1053, 1987.

Ivanov, A. P. et al., "New Method for High-Range Resolution Measurements of Light Scattering in Optically Dense Inhomogeneous Media," *Optics Letters*, vol. 1, pp. 226-228, Dec. 1977.

Ivanov, A. P. et al., "Interferometric Study of the Spatial Structure of a Light-Scattering Medium," *Journal of Applied Spectroscopy*, vol. 28, pp. 518-525, 1978.

Kazovsky, L. G. et al., "Heterodyne Detection Through Rain, Snow, and Turbid Media: Effective Receiver Size at Optical Through Millimeter Wavelenghths," *Applied Optics*, vol. 22, pp. 706-710, Mar. 1983.

Kersey, A. D. et al., "Adaptive Polarization Diversity Receiver Configuration for Coherent Optical Fiber Communications," *Electronics Letters*, vol. 25, pp. 275-277, Feb. 1989.

Kohlhaas, Andreas et al., "High-Resolution OCDR for Testing Integrated-Optical Waveguides: Dispersion-Corrupted Experimental Data Corrected by a Numerical Algorithm," *Journal of Lightwave Technology*, vol. 9, pp. 1493-1502, Nov. 1991.

Larkin, Kieran G., "Efficient Nonlinear Algorithm for Envelope Detection in White Light Interferometry," *Journal of the Optical Society of America A-Optics Image Science and Vision*, vol. 13, pp. 832-843, Apr. 1996.

Leitgeb, R. et al., "Spectral measurement of Absorption by Spectroscopic Frequency-Domain Optical Coherence Tomography," *Optics Letters*, vol. 25, pp. 820-822, Jun. 2000.

Lexer, F. et al., "Wavelength-Tuning Interferometry of Intraocular Distances," *Applied Optics*, vol. 36, pp. 6548-6553, Sep. 1997.

Mitsui, Takahisa, "Dynamic Range of Optical Reflectometry with Spectral Interferometry," *Japanese Journal of Applied Physics Part 1-Regular Papers Short Notes & Review Papers*, vol. 38, pp. 6133-6137, 1999.

Naganuma, Kazunori et al., "Group-Delay Measurement Using the Fourier-Transform of an Interferometric Cross-Correlation Generated by White Light," *Optics Letters*, vol. 15, pp. 393-395, Apr. 1990.

Okoshi,Takanori, "Polarization-State Control Schemes for Heterodyne or Homodyne Optical Fiber Communications," *Journal of Lightwave Technology*, vol. LT-3, pp. 1232-1237, Dec. 1995.

Passy, R. et al., "Experimental and Theoretical Investigations of Coherent OFDR with Semiconductor-Laser Sources," *Journal of Lightwave Technology*, vol. 12, pp. 1622-1630, Sep. 1994.

Podoleanu, Adrian G., "Unbalanced Versus Balanced Operation in an Optical Coherence Tomography System," *Applied Optics*, vol. 39, pp. 173-182, Jan. 2000.

Price, J. H. V. et al., "Tunable, Femtosecond Pulse Source Operating in the Range 1.06-1.33 mu m Based on an Yb3+-doped Holey Fiber Amplifier," *Journal of the Optical Society of America B-Optical Physics*, vol. 19, pp. 1286-1294, Jun. 2002.

Schmitt, J. M. et al, "Measurement of Optical-Properties of Biological Tissues by Low-Coherence Reflectometry," *Applied Optics*, vol. 32, pp. 6032-6042, Oct. 1993.

Silberberg, Y. et al., "Passive-Mode Locking of a Semiconductor Diode-Laser," *Optics Letters*, vol. 9, pp. 507-509, Nov. 1984.

Smith, L. Montgomery et al., "Absolute Displacement Measurements Using Modulation of the Spectrum of White-Light in a Michelson Interferometer," *Applied Optics*, vol. 28, pp. 3339-3342, Aug. 1989.

Sonnenschein, C. M. et al., "Signal-To-Noise Relationships for Coaxial Systems that Heterodyne Backscatter from Atmosphere," *Applied Optics*, vol. 10, pp. 1600-1604, Jul. 1971.

Sorin, W. V. et al., "Measurement of Rayleigh Backscattering at 1.55 mu m Spatial Resolution," *IEEE Photonics Technology Letters*, vol. 4, pp. 374-376, Apr. 1992.

Sorin, W. V. et al., "A Simple Intensity Noise-Reduction Technique for Optical Low-Coherence Reflectometry," *IEEE Photonics Technology Letters*, vol. 4, pp. 1404-1406, Dec. 1992.

Swanson, E. A. et al., "High-Speed Optical Coherence Domain Reflectometry," *Optics Letters*, vol. 17, pp. 151-153, Jan. 1992.

Takada, K. et al., "High-Resolution OFDR with Incorporated Fiberoptic Frequency Encoder," *IEEE Photonics Technology Letters*, vol. 4, pp. 1069-1072, Sep. 1992.

Takada, Kazumasa et al., "Narrow-Band light Source with Acoustooptic Tunable Filter for Optical Low-Coherence Reflectometry," *IEEE Photonics Techology Letters*, vol. 8, pp. 658-660, May, 1996.

Takada, Kazumasa et al., "New Measurement System for Fault Location in Optical Wave-Guide Devices Based on an Interometric-Technique," *Applied Optics*, vol. 26, pp. 1603-1606, May 1987.

Tateda, Mitsuhiro et al., "Interferometric Method for Chromatic Dispersion Measurement in a Single-Mode Optical Fiber," *IEEE Journal of Quantum Electronics*, vol. 17, pp. 404-407, Mar. 1981.

Toide, M. et al., "Two-Dimensional Coherent Detection Imaging in Multiple Scattering Media Based the Directional Resolution Capability of the Optical Heterodyne Method," *Applied Physics B(Photophysics and Laser Chemistry)*, vol. B52, pp. 391-394, 1991.

Trutna, W. R. et al., "Continuously Tuned External-Cavity Semiconductor-Laser," *Journal of Lightwave Technology*, vol. 11, pp. 1279-1286, Aug. 1993.

Uttam, Deepak et al., "Precision Time Domain Reflectometry in Optical Fiber Systems Using a Frequency Modulated Continuous Wave Ranging Technique," *Journal of Lightwave Technology*, vol. 3, pp. 971-977, Oct. 1985.

Von Der Weid, J. P. et al., "On the Characterization of Optical Fiber Network Components with Optical Frequency Domain Reflectometry," *Journal of Lightwave Technology*, vol. 15, pp. 1131-1141, Jul. 1997.

Wysocki, P.F. et al., "Broad-Spectrum Wavelength-Swept, Erbium-Doped Fiber Laser at 1.55-Mu-M," *Optics Letters*, vol. 15, pp. 879-881, Aug. 1990.

Youngquist, Robert C. et al., "Optical Coherence-Domain Reflectometry—A New Optical Evaluation Technique," *Optics Letters*, vol. 12, pp. 158-160, Mar. 1987.

Yun, S. H. et al., "Wavelength-Swept Fiber Laser with Frequency Shifted Feedback and Resonantly Swept Intra-Cavity Acoustooptic Tunable Filter," *IEEE Journal of Selected Topics in Quantum Electronics*, vol. 3, pp. 1087-1096, Aug. 1997.

Yun, S. H. et al., "Interrogation of Fiber Grating Sensor Arrays with a Wavelength-Swept Fiber Laser," *Optics Letters*, vol. 23, pp. 843-845, Jun. 1998.

Yung, K. M., "Phase-Domain Processing of Optical Coherence Tomography Images," *Journal of Biomedical Optics*, vol. 4, pp. 125-136, Jan. 1999.

Zhou, Xiao-Qun et al., "Extended-Range FMCW Reflectometry Using an optical Loop with a Frequency Shifter," *IEEE Photonics Technology Letters*, vol. 8, pp. 248-250, Feb. 1996.

Zorabedian, Paul et al., "Tuning Fidelity of Acoustooptically Controlled External Cavity Semiconductor-Lasers," *Journal of Lightwave Technology*, vol. 13, pp. 62-66, Jan. 1995.

Victor S. Y. Lin et al., "A Porous Silicon-Based Optical Interferometric Biosensor," *Science Magazine*, vol. 278, pp. 840-843, Oct. 31, 1997.

De Boer, Johannes F. et al., "Review of Polarization Sensitive Optical Coherence Tomography and Stokes Vector Determination," *Journal of Biomedical Optics*, vol. 7, No. 3, Jul. 2002, pp. 359-371.

Jiao, Shuliang et al., "Depth-Resolved Two-Dimensional Stokes Vectors of Backscattered Light and Mueller Matrices of Biological Tissue Measured with Optical Coherence Tomography," *Applied Optics*, vol. 39, No. 34, Dec. 1, 2000, pp. 6318-6324.

Park, B. Hyle et al., "In Vivo Burn Depth Determination by High-Speed Fiber-Based Polarization Sensitive Optical Coherence Tomography," *Journal of Biomedical Optics*, vol. 6 No. 4, Oct. 2001, pp. 474-479.

Roth, Jonathan E. et al., "Simplified Method for Polarization-Sensitive Optical Coherence Tomography," *Optics Lettes*, vol. 26, No. 14, Jul. 15, 2001, pp. 1069-1071.

Hitzenberger, Christoper K. et al., "Measurement and Imaging of Birefringence and Optic Axis Orientation by Phase Resolved Polarization Sensitive Optical Coherence Tomography," *Optics Express*, vol. 9, No. 13, Dec. 17, 2001, pp. 780-790.

Wang, Xueding et al., "Propagation of Polarized Light in Birefringent Turbid Media: Time-Resolved Simulations," Optical Imaging Laboratory, Biomedical Engineering Program, Texas A&M University.

Wong, Brian J.F. et al., "Optical Coherence Tomography of the Rat Cochlea," *Journal of Biomedical Optics*, vol. 5, No. 4, Oct. 2000, pp. 367-370.

Yao, Gang et al., "Propagation of Polarized Light in Turbid Media: Simulated Animation Sequences," *Optics Express*, vol. 7, No. 5, Aug. 28, 2000, pp. 198-203.

Wang, Xiao-Jun et al., "Characterization of Dentin and Enamel by Use of Optical Coherence Tomography," *Applied Optics*, vol. 38, No. 10, Apr. 1, 1999, pp. 2092-2096.

De Boer, Johannes F. et al., "Determination of the Depth-Resolved Stokes Parameters of Light Backscattered from Turbid Media by use of Polarization-Sensitive Optical Coherence Tomography," *Optics Letters*, vol. 24, No. 5, Mar. 1, 1999, pp. 300-302.

Ducros, Mathieu G. et al., "Polarization Sensitive Optical Coherence Tomography of the Rabbit Eye," *IEEE Journal of Selected Topics in Quantum Electronics*, vol. 5, No. 4, Jul./Aug. 1999, pp. 1159-1167.

Groner, Warren et al., "Orthogonal Polarization Spectral Imaging: A New Method for Study of the Microcirculation," *Nature Medicine Inc.*, vol. 5 No. 10, Oct. 1999, pp. 1209-1213.

De Boer, Johannes F. et al., "Polarization Effects in Optical Coherence Tomography of Various Viological Tissues," *IEEE Journal of Selected Topics in Quantum Electronics*, vol. 5, No. 4, Jul./Aug. 1999, pp. 1200-1204.

Yao, Gang et al., "Two-Dimensional Depth-Resolved Mueller Matrix Characterization of Biological Tissue by Optical Coherence Tomography," *Optics Letters*, Apr. 15, 1999, vol. 24, No. 8, pp. 537-539.

Lu, Shih-Yau et al., "Homogeneous and Inhomogeneous Jones Matrices," *J. Opt. Soc. Am. A.*, vol. 11, No. 2, Feb. 1994, pp. 766-773.

Bickel, S. William et al., "Stokes Vectors, Mueller Matrices, and Polarized Scattered Light," *Am. J. Phys.*, vol. 53, No. 5, May 1985 pp. 468-478.

Bréhonnet, F. Le Roy et al., "Optical Media and Target Characterization by Mueller Matrix Decomposition," *J. Phys. D: Appl. Phys.* 29, 1996, pp. 34-38.

Cameron, Brent D. et al., "Measurement and Calculation of the Two-Dimensional Backscattering Mueller Matrix of a Turbid Medium," *Optics Letters*, vol. 23, No. 7, Apr. 1, 1998, pp. 485-487.

De Boer, Johannes F. et al., "Two-Dimensional Birefringence Imaging in Biological Tissue by Polarization-Sensitive Optical Coherence Tomography," *Optics Letters*, vol. 22, No. 12, Jun. 15, 1997, pp. 934-936.

De Boer, Johannes F. et al., "Imaging Thermally Damaged Tissue by Polarization Sensitive Optical Coherence Tomography," *Optics Express*, vol. 3, No. 6, Sep. 14, 1998, pp. 212-218.

Everett, M.J. et al., "Birefringence Characterization of Biological Tissue by Use of Optical Coherence Tomography," *Optics Letters*, vol. 23, No. 3, Feb. 1, 1998, pp. 228-230.

Hee, Michael R. et al., "Polarization-Sensitive Low-Coherence Reflectometer for Birefringence Characterization and Ranging," *J. Opt. Soc. Am. B.*, vol. 9, No. 6, Jun. 1992, pp. 903-908.

Barakat, Richard, "Statistics of the Stokes Parameters," *J. Opt. Soc. Am. B.*, vol. 4, Jul. 1987, pp. 1256-1263.

Schmitt, J.M. et al., "Cross-Polarized Backscatter in Optical Coherence Tomography of Biological Tissue," *Optics Letters*, vol. 23, No. 13, Jul. 1, 1998, pp. 1060-1062.

Schoenenberger, Klaus et al., "Mapping of Birefringence and Thermal Damage in Tissue by use of Polarization-Sensitive Optical Coherence Tomography," *Applied Optics*, vol. 37, No. 25, Sep. 1, 1998, pp. 6026-6036.

Pierce, Mark C. et al., "Simultaneous Intensity, Birefringence, and Flow Measurements with High-Speed Fiber-Based Optical Coherence Tomography," *Optics Letters*, vol. 27, No. 17, Sep. 1, 2002, pp. 1534-1536.

De Boer, Johannes F. et al., "Review of Polarization Sensitive Optical Coherence Tomography and Stokes Vector Determination," *Journal of Biomedical Optics*, Jul. 2002, vol. 7, No. 3, pp. 359-371.

Fried, Daniel et al., "Imaging Caries Lesions and Lesion Progression with Polarization Sensitive Optical Coherence Tomography," *Journal of Biomedical Optics*, vol. 7, No. 4, Oct. 2002, pp. 618-627.

Jiao, Shuliang et al., "Two-Dimensional Depth-Resolved Mueller Matrix of Biological Tissue Measured with Double-Beam Polarization-Sensitive Optical Coherence Tomography," *Optics Letters*, vol. 27, No. 2, Jan. 15, 2002, pp. 101-103.

Jiao, Shuliang et al., "Jones-Matrix Imaging of Biological Tissues with Quadruple-Channel Optical Coherence Tomography," *Journal of Biomedical Optics*, vol. 7, No. 3, Jul. 2002, pp. 350-358.

Kuranov, R.V. et al., "Complementary Use of Cross-Polarization and Standard OCT for Differential Diagnosis of Pathological Tissues," *Optics Express*, vol. 10, No. 15, Jul. 29, 2002, pp. 707-713.

Cense, Barry et al., "In Vivo Depth-Resolved Birefringence Measurements of the Human Retinal Nerve Fiber Layer by Polarization-Sensitive Optical Coherence Tomography," *Optics Letters*, vol. 27, No. 18, Sep. 15, 2002, pp. 1610-1612.

Ren, Hongwu et al., "Phase-Resolved Functional Optical Coherence Tomography: Simultaneous Imaging of In Situ Tissue Structure, Blood Flow Velocity, Standard Deviation, Birefringence, and Stokes Vectors in Human Skin," *Optics Letters*, vol. 27, No. 19, Oct. 1, 2002, pp. 1702-1704.

Tripathi, Renu et al., "Spectral Shaping for Non-Gaussian Source Spectra in Optical Coherence Tomography," *Optics Letters*, vol. 27, No. 6, Mar. 15, 2002, pp. 406-408.

Yasuno, Y. et al., "Birefringence Imaging of Human Skin by Polarization-Sensitive Spectral Interferometric Optical Coherence Tomography," *Optics Letters*, vol. 27, No. 20, Oct. 15, 2002 pp. 1803-1805.

White, Brian R. et al., "In Vivo Dynamic Human Retinal Blood Flow Imaging Using Ultra-High-Speed Spectral Domain Optical Doppler Tomography," *Optics Express*, vol. 11, No. 25, Dec. 15, 2003, pp. 3490-3497.

De Boer, Johannes F. et al., "Improved Signal-to-Noise Ratio in Spectral-Domain Compared with Time-Domain Optical Coherence Tomography," *Optics Letters*, vol. 28, No. 21, Nov. 1, 2003, pp. 2067-2069.

Jiao, Shuliang et al., "Optical-Fiber-Based Mueller Optical Coherence Tomography," *Optics Letters*, vol. 28, No. 14, Jul. 15, 2003, pp. 1206-1208.

Jiao, Shuliang et al., "Contrast Mechanisms in Polarization-Sensitive Mueller-Matrix Optical Coherence Tomography and Application in Burn Imaging," *Applied Optics*, vol. 42, No. 25, Sep. 1, 2003, pp. 5191-5197.

Moreau, Julien et al., "Full-Field Birefringence Imaging by Thermal-Light Polarization-Sensitive Optical Coherence Tomography. I. Theory," *Applied Optics*, vol. 42, No. 19, Jul. 1, 2003, pp. 3800-3810.

Moreau, Julien et al., "Full-Field Birefringence Imaging by Thermal-Light Polarization-Sensitive Optical Coherence Tomography. II. Instrument and Results," *Applied Optics*, vol. 42, No. 19, Jul. 1, 2003, pp. 3811-3818.

Morgan, Stephen P. et al., "Surface-Reflection Elimination in Polarization Imaging of Superficial Tissue," *Optics Letters*, vol. 28, No. 2, Jan. 15, 2003, pp. 114-116.

Oh, Jung-Taek et al., "Polarization-Sensitive Optical Coherence Tomography for Photoelasticity Testing of Glass/Epoxy Composites," *Optics Express*, vol. 11, No. 14, Jul. 14, 2003, pp. 1669-1676.

Park, B. Hyle et al., "Real-Time Multi-Functional Optical Coherence Tomography," *Optics Express*, vol. 11, No. 7, Apr. 7, 2003, pp. 782-793.

Shribak, Michael et al., "Techniques for Fast and Sensitive Measurements of Two-Dimensional Birefringence Distributions," *Applied Optics*, vol. 42, No. 16, Jun. 1, 2003, pp. 3009-3017.

Somervell, A.R.D. et al., "Direct Measurement of Fringe Amplitude and Phase Using a Heterodyne Interferometer Operating in Broadband Light," *Elsevier, Optics Communications*, Oct. 2003.

Stifter, D. et al., "Polarisation-Sensitive Optical Coherence Tomography for Material Characterisation and Strain-Field Mapping," *Applied Physics A* 76, Materials Science & Processing, Jan. 2003, pp. 947-951.

Davé, Digant P. et al., "Polarization-Maintaining Fiber-Based Optical Low-Coherence Reflectometer for Characterization and Ranging of Birefringence," *Optics Letters*, vol. 28, No. 19, Oct. 1, 2003, pp. 1775-1777.

Yang, Ying et al., "Observations of Birefringence in Tissues from Optic-Fibre-Based Optical Coherence Tomography," *Measurement Science and Technology*, Nov. 2002, pp. 41-46.

Yun, S.H. et al., "High-Speed Optical Frequency-Domain Imaging," *Optics Express*, vol. 11, No. 22, Nov. 3, 2003, pp. 2953-2963.

Yun, S.H. et al., "High-Speed Spectral-Domain Optical Coherence Tomography at 1.3 μm Wavelength," *Optics Express*, vol. 11, No. 26, Dec. 29, 2003, pp. 3598-3604.

Zhang, Jun et al., "Determination of Birefringence and Absolute Optic Axis Orientation Using Polarization-Sensitive Optical Coherence Tomography with PM Fibers," *Optics Express*, vol. 11, No. 24, Dec. 1, 2003, pp. 3262-3270.

Pircher, Michael et al., "Three Dimensional Polarization Sensitive OCT of Human Skin In Vivo," 2004, *Optical Society of America*.

Götzinger, Erich et al., "Measurement and Imaging of Birefringent Properties of the Human Cornea with Phase-Resolved, Polarization-Sensitive Optical Coherence Tomography," *Journal of Biomedical Optics*, vol. 9, No. 1, Jan./Feb. 2004, pp. 94-102.

Guo, Shuguang et al., "Depth-Resolved Birefringence and Differential Optical Axis Orientation Measurements with Finer-based Polarization-Sensitive Optical Coherence Tomography," *Optics Letters*, vol. 29, No. 17, Sep. 1, 2004, pp. 2025-2027.

Huang, Xiang-Run et al.,"Variation of Peripapillary Retinal Nerve Fiber Layer Birefringence in Normal Human Subjects," *Investigative Ophthalmology & Visual Science*, vol. 45, No. 9, Sep. 2004, pp. 3073-3080.

Matcher, Stephen J. et al., "The Collagen Structure of Bovine Intervertevbral Disc Studied Using Polarization-Sensitive Optical Coherence Tomography," *Physics in Medicine and Biology*, 2004, pp. 1295-1306.

Nassif, Nader et al., "In Vivo Human Retinal Imaging by Ultrahigh-Speed Spectral Domain Optical Coherence Tomography," *Optics Letters*, vol. 29, No. 5, Mar. 1, 2004, pp. 480-482.

Nassif, N. A. et al., "In Vivo High-Resolution Video-Rate Spectral-Domain Optical Coherence Tomography of the Human Retina and Optic Nerve," *Optics Express*, vol. 12, No. 3, Feb. 9, 2004, pp. 367-376.

Park, B. Hyle et al., "Comment on Optical-Fiber-Based Mueller Optical Coherence Tomography," *Optics Letters*, vol. 29, No. 24, Dec. 15, 2004, pp. 2873-2874.

Park, B. Hyle et al., "Jones Matrix Analysis for a Polarization-Sensitive Optical Coherence Tomography System Using Fiber-Optic Components," *Optics Letters*, vol. 29, No. 21, Nov. 1, 2004, pp. 2512-2514.

Pierce, Mark C. et al., "Collagen Denaturation can be Quantified in Burned Human Skin Using Polarization-Sensitive Optical Coherence Tomography," *Elsevier, Burns*, 2004, pp. 511-517.

Pierce, Mark C. et al., "Advances in Optical Coherence Tomography Imaging for Dermatology," *The Society for Investigative Dermatology, Inc.* 2004, pp. 458-463.

Pierce, Mark C. et al., "Birefringence Measurements in Human Sking Using Polarization-Sensitive Optical Coherence Tomography," *Journal of Biomedical Optics*, vol. 9, No. 2, Mar./Apr. 2004, pp. 287-291.

Cense, Barry et al., "In Vivo Birefringence and Thickness Measurements of the Human Retinal Nerve Fiber Layer Using Polarization-Sensitive Optical Coherence Tomography," *Journal of Biomedical Optics*, vol. 9, No. 1, Jan./Feb. 2004, pp. 121-125.

Pircher, Michael et al., "Imaging of Polarization Properties of Human Retina in Vivo with Phase Resolved Transversal PS-OCT," *Optics Express*, vol. 12, No. 24, Nov. 29, 2004 pp. 5940-5951.

Pircher, Michael et al., "Transversal Phase Resolved Polarization Sensitive Optical Coherence Tomography," *Physics in Medicine & Biology*, 2004, pp. 1257-1263.

Srinivas, Shyam M. et al., "Determination of Burn Depth by Polarization-Sensitive Optical Coherence Tomography," *Journal of Biomedical Optics*, vol. 9, No. 1, Jan./Feb. 2004, pp. 207-212.

Strasswimmer, John et al., "Polarization-Sensitive Optical Coherence Tomography of Invasive Basal Cell Carcinoma," *Journal of Biomedical Optics*, vol. 9, No. 2, Mar./Apr. 2004, pp. 292-298.

Todorović, Miloš et al., "Determination of Local Polarization Properties of Biological Samples in the Presence of Diattenuation by use of Mueller Optical Coherence Tomography," *Optics Letters*, vol. 29, No. 20, Oct. 15, 2004, pp. 2402-2404.

Yasuno, Yoshiaki et al., "Polarization-Sensitive Complex Fourier Domain Optical Coherence Tomography for Jones Matrix Imaging of Biological Samples," *Applied Physics Letters*, vol. 85, No. 15, Oct. 11, 2004, pp. 3023-3025.

Acioli, L. H., M. Ulman, et al. (1991). "Femtosecond Temporal Encoding in Barium-Titanate," *Optics Letters* 16(24): 1984-1986.

Aigouy, L., A. Lahrech, et al. (1999). "Polarization effects in apertureless scanning near-field optical microscopy: an experimental study." *Optics Letters* 24(4): 187-189.

Akiba, M., K. P. Chan, et al. (2003). "Full-field optical coherence tomography by two-dimensional heterodyne detection with a pair of CCD cameras." *Optics Letters* 28(10): 816-818.

Akkin, T., D. P. Dave, et al. (2004). "Detection of neural activity using phase-sensitive optical low-coherence reflectometry." *Optics Express* 12(11): 2377-2386.

Akkin, T., D. P. Dave, et al. (2003). "Surface analysis using phase sensitive optical low coherence reflectometry." *Lasers in Surgery and Medicine*: 4-4.

Akkin, T., D. P. Dave, et al. (2003). "Imaging tissue response to electrical and photothermal stimulation with nanometer sensitivity." *Lasers in Surgery and Medicine* 33(4): 219-225.

Akkin, T., T. E. Milner, et al. (2002). "Phase-sensitive measurement of birefringence change as an indication of neural functionality and diseases." *Lasers in Surgery and Medicine*: 6-6.

Andretzky, P., Lindner, M.W., Herrmann, J.M., Schultz, A., Konzog, M., Kiesewetter, F., Haeusler, G. (1999). "Optical coherence tomography by 'spectral radar': Dynamic range estimation and in vivo measurements of skin." *Proceedings of SPIE—The International Society for Optical Engineering* 3567: pp. 78-87.

Antcliff, R. J., T. J. ffytche, et al. (2000). "Optical coherence tomography of melanocytoma." *American Journal of Ophthalmology* 130(6): 845-7.

Antcliff, R. J., M. R. Stanford, et al. (2000). "Comparison between optical coherence tomography and fundus fluorescein angiography for the detection of cystoid macular edema in patients with uveitis." *Ophthalmology* 107(3): 593-9.

Anvari, B., T. E. Milner, et al. (1995). "Selective Cooling of Biological Tissues—Application for Thermally Mediated Therapeutic Procedures." *Physics in Medicine and Biology* 40(2): 241-252.

Anvari, B., B. S. Tanenbaum, et al. (1995). "A Theoretical-Study of the Thermal Response of Skin to Cryogen Spray Cooling and Pulsed-Laser Irradiation—Implications for Treatment of Port-Wine Stain Birthmarks." *Physics in Medicine and Biology* 40(9): 1451-1465.

Arend, O., M. Ruffer, et al. (2000). "Macular circulation in patients with diabetes mellitus with and without arterial hypertension." *British Journal of Ophthalmology* 84(12): 1392-1396.

Arimoto, H. and Y. Ohtsuka (1997). "Measurements of the complex degree of spectral coherence by use of a wave-front-folded interferometer." *Optics Letters* 22(13): 958-960.

Azzolini, C., F. Patelli, et al. (2001). "Correlation between optical coherence tomography data and biomicroscopic interpretation of idiopathic macular hole." *American Journal of Ophthalmology* 132(3): 348-55.

Baba, T., K. Ohno-Matsui, et al. (2002). "Optical coherence tomography of choroidal neovascularization in high myopia." *Acta Ophthalmoloqica Scandinavica* 80(1): 82-7.

Bail, M. A. H., Gerd; Herrmann, Juergen M.; Lindner, Michael W.; Ringler, R. (1996). "Optical coherence tomography with the "spectral radar": fast optical analysis in volume scatterers by short-coherence interferometry." *Proc. SPIE*, 2925: p. 298-303.

Baney, D. M. and W. V. Sorin (1993). "Extended-Range Optical Low-Coherence Reflectometry Using a Recirculating Delay Technique." *Ieee Photonics Technology Letters* 5(9): 1109-1112.

Baney, D. M., B. Szafraniec, et al. (2002). "Coherent optical spectrum analyzer." *Ieee Photonics Technology Letters* 14(3): 355-357.

Barakat, R. (1981). "Bilinear Constraints between Elements of the 4by4 Mueller-Jones Transfer-Matrix of Polarization Theory." *Optics Communications* 38(3): 159-161.

Barakat, R. (1993). "Analytic Proofs of the Arago-Fresnel Laws for the Interference of Polarized-Light." *Journal of the Optical Society of America a-Optics Image Science and Vision* 10(1): 180-185.

Barbastathis, G. and D. J. Brady (1999). "Multidimensional tomography imaging using volume holography." *Proceedings of the Ieee* 87(12): 2098-2120.

Bardal, S., A. Kamal, et al. (1992). "Photoinduced Birefringence in Optical Fibers—a Comparative-Study of Low-Birefringence and High-Birefringence Fibers." *Optics Letters* 17(6): 411-413.

Barsky, S. H., S. Rosen, et al. (1980). "Nature and Evolution of Port Wine Stains—Computer-Assisted Study." *Journal of Investigative Dermatology* 74(3): 154-157.

Barton, J. K., J. A. Izatt, et al. (1999). "Three-dimensional reconstruction of blood vessels from in vivo color Doppler optical coherence tomography images." *Dermatology* 198(4): 355-361.

Barton, J. K., A. Rollins, et al. (2001). "Photothermal coagulation of blood vessels: a comparison of high-speed optical coherence tomography and numerical modelling." *Physics in Medicine and Biology* 46.

Barton, J. K., A. J. Welch, et al. (1998). "Investigating pulsed dye laser-blood vessel interaction with color Doppler optical coherence tomography." *Optics Express* 3.

Bashkansky, M., M. D. Duncan, et al. (1997). "Subsurface defect detection in ceramics by high-speed high-resolution optical coherent tomography." *Optics Letters* 22 (1): 61-63.

Bashkansky, M. and J. Reintjes (2000). "Statistics and reduction of speckle in optical coherence tomography." *Optics Letters* 25(8): 545-547.

Baumgartner, A., S. Dichtl, et al. (2000). "Polarization-sensitive optical coherence tomography of dental structures." *Caries Research* 34(1): 59-69.

Baumgartner, A., C. K. Hitzenberger, "Resolution-improved dual-beam and standard optical coherence tomography: a comparison." *Graefes Archive for Clinical and Experimental Ophthalmology* 238(5): 385-392.

Baumgartner, A., C. K. Hitzenberger, et al. (1998). "Signal and resolution enhancements in dual beam optical coherence tomography of the human eye." *Journal of Biomedical Optics* 3(1): 45-54.

Beaurepaire, E., P. Gleyzes, et at. (1998). *Optical coherence microscopy for the in-depth study of biological structures: System based on a parallel detection scheme*, Proceedings of SPIE—The International Society for Optical Engineering.

Beaurepaire, E., L. Moreaux, et al. (1999). "Combined scanning optical coherence and two-photon-excited fluorescence microscopy." *Optics Letters* 24(14): 969-971.

Bechara, F. G., T. Gambichler, et al. (2004). "Histomorphologic correlation with routine histology and optical coherence tomography." *Skin Research and Technology* 10 (3): 169-173.

Bechmann, M., M. J. Thiel, et al. (2000). "Central corneal thickness determined with optical coherence tomography in various types of glaucoma. [see comments]." *British Journal of Ophthalmology* 84(11): 1233-7.

Bek, T. and M. Kandi (2000). "Quantitative anomaloscopy and optical coherence tomography scanning in central serous chorioretinopathy." *Acta Ophthalmologica Scandinavica* 78(6): 632-7.

Benoit, A. M., K. Naoun, et al. (2001). "Linear dichroism of the retinal nerve fiber layer expressed with Mueller matrices." *Applied Optics* 40(4): 565-569.

Bicout, D., C. Brosseau, et al. (1994). "Depolarization of Multiply Scatterd Waves by Spherical Diffusers—Influence of the Size Parameter." *Physical Review* E 49(2): 1767-1770.

Blanchot, L., M. Lebec, et al. (1997). *Low-coherence in depth microscopy for biological tissues imaging: Design of a real time control system*. Proceedings of SPIE—The International Society for Optical Engineering.

Blumenthal, E. Z. and R. N. Weinreb (2001). "Assessment of the retinal nerve fiber layer in clinical trials of glaucoma neuroprotection. [Review] [36 refs]." *Survey of Ophthalmology* 45(Suppl 3): S305-12; discussion S332-4.

Blumenthal, E. Z., J. M. Williams, et al. (2000). "Reproducibility of nerve fiber layer thickness measurements by use of optical coherence tomography." *Ophthalmology* 107(12): 2278-82.

Boppart, S. A., B. E. Bouma, et al. (1996). "Imaging developing neural morphology using optical coherence tomography." *Journal of Neuroscience Methods* 70.

Boppart, S. A., B. E. Bouma, et al. (1997). "Forward-imaging instruments for optical coherence tomography." *Optics Letters* 22.

Boppart, S. A., B. E. Bouma, et al. (1998). "Intraoperative assessment of microsurgery with three-dimensional optical coherence tomography." *Radiology* 208: 81-86.

Boppart, S. A., J. Herrmann, et al. (1999). "High-resolution optical coherence tomography-guided laser ablation of surgical tissue." *Journal of Surgical Research* 82(2): 275-84.

Bouma, B. E. and J. G. Fujimoto (1996). "Compact Kerr-lens mode-locked resonators." *Optics Letters* 21. 134-136.

Bouma, B. E., L. E. Nelson, et al. (1998). "Optical coherence tomographic imaging of human tissue at 1.55 mu m and 1.81 mu m using Er and Tm-doped fiber sources." *Journal of Biomedical Optics* 3. 76-79.

Bouma, B. E., M. Ramaswamy-Paye, et al. (1997). "Compact resonator designs for mode-locked solid-state lasers." *Applied Physics B (Lasers and Optics)* B65. 213-220.

Bouma, B. E. and G. J. Tearney (2002). "Clinical imaging with optical coherence tomography." *Academic Radiology* 9(8): 942-953.

Bouma, B. E., G. J. Tearney, et al. (1996). "Self-phase-modulated Kerr-lens mode-locked Cr:forsterite laser source for optical coherence tomography." *Optics Letters* 21(22): 1839.

Bouma, B. E., G. J. Tearney, et al. (2000). "High-resolution imaging of the human esophagus and stomach in vivo using optical coherence tomography." *Gastrointestinal Endoscopy* 51(4): 467-474.

Bouma, B. E., G. J. Tearney, et al. (2003). "Evaluation of intracoronary stenting by intravascular optical coherence tomography." *Heart* 89(3): 317-320.

Bourquin, S., V. Monterosso, et al. (2000). "Video-rate optical low-coherence reflectometry based on a linear smart detector array." *Optics Letters* 25(2): 102-104.

Bourquin, S., P. Seitz, et al. (2001). "Optical coherence tomography based on a two-dimensional smart detector array." *Optics Letters* 26(8): 512-514.

Bouzid, A., M. A. G. Abushagur, et al. (1995). "Fiber-optic four-detector polarimeter." *Optics Communications* 118(3-4): 329-334.

Bowd, C., R. N. Weinreb, et al. (2000). "The retinal nerve fiber layer thickness in ocular hypertensive, normal, and glaucomatous eyes with optical coherence tomography." *Archives of Ophthalmology* 118(1): 22-6.

Bowd, C., L. M. Zangwill, et al. (2001). "Detecting early glaucoma by assessment of retinal nerve fiber layer thickness and visual function." *Investigative Ophthalmology & Visual Science* 42(9): 1993-2003.

Bowd, C., L. M. Zangwill, et al. (2002). "Imaging of the optic disc and retinal nerve fiber layer: the effects of age, optic disc area, refractive error, and gender." *Journal of the Optical Society of America, A, Optics, Image Science, & Vision* 19(1): 197-207.

Brand, S., J. M. Poneros, et al. (2000). "Optical coherence tomography in the gastrointestinal tract." *Endoscopy* 32(10): 796-803.

Brezinski, M. E. and J. G. Fujimoto (1999). "Optical coherence tomography: high-resolution imaging in nontransparent tissue." *IEEE Journal of Selected Topics in Quantum Electronics* 5(4): 1185-1192.

Brezinski, M. E., G. J. Tearney, et al. (1996). "Imaging of coronary artery microstructure (in vitro) with optical coherence tomography." *American Journal of Cardiology* 77 (1): 92-93.

Brezinski, M. E., G. J. Tearney, et al. (1996). "Optical coherence tomography for optical biopsy—Properties and demonstration of vascular pathology." *Circulation* 93(6): 1206-1213.

Brezinski, M. E., G. J. Tearney, et al. (1997). "Assessing atherosclerotic plaque morphology: Comparison of optical coherence tomography and high frequency intravascular ultrasound." *Heart* 77(5): 397-403.

Brink, H. B. K. and G. J. Vanblokland (1988). "Birefringence of the Human Foveal Area Assessed Invivo with Mueller-Matrix Ellipsometry." *Journal of the Optical Society of America a-Optics Image Science and Vision* 5(1): 49-57.

Brosseau, C. and D. Bicout (1994). "Entropy Production in Multiple-Scattering of Light by a Spatially Random Medium." *Physical Review* E 50(6): 4997-5005.

Burgoyne, C. F., D. E. Mercante, et al. (2002). "Change detection in regional and volumetric disc parameters using longitudinal confocal scanning laser tomography." *Ophthalmology* 109(3): 455-66.

Candido, R. and T. J. Allen (2002). "Haemodynamics in microvascular complications in type 1 diabetes." *Diabetes-Metabolism Research and Reviews* 18(4): 286-304.

Cense, B., T. C. Chen, et al. (2004). "Thickness and birefringence of healthy retinal nerve fiber layer tissue measured with polarization-sensitive optical coherence tomography." *Investigative Ophthalmology & Visual Science* 45(8): 2606-2612.

Cense, B., N. Nassif, et al. (2004). "Ultrahigh-Resolution High-Speed Retinal Imaging Using Spectral-Domain Optical Coherence Tomography." *Optics Express* 12(11): 2435-2447.

Chance, B., J. S. Leigh, et al. (1988). "Comparison of Time-Resolved and Time-Unresolved Measurements of Deoxyhemoglobin in Brain." *Proceedings of the National Academy of Sciences of the United States of America* 85(14): 4971-4975.

Chang, E. P., D. A. Keedy, et al. (1974). "Ultrastructures of Rabbit Corneal Stroma—Mapping of Optical and Morphological Anisotropies." *Biochimica Et Biophysica Acta* 343(3): 615-626.

Chartier, T., A. Hideur, et al. (2001). "Measurement of the elliptical birefringence of single-mode optical fibers." *Applied Optics* 40(30): 5343-5353.

Chauhan, B. C., J. W. Blanchard, et al. "Technique for Detecting Serial Topographic Changes in the Optic Disc and Peripapillary Retina Using Scanning Laser Tomograph." *Invest Ophthalmol Vis Sci* 41: 775-782.

Chen, Z. P., T. E. Milner, et al. (1997). "Optical Doppler tomographic imaging of fluid flow velocity in highly scattering media." *Optics Letters* 22(1): 64-66.

Chen, Z. P., T. E. Milner, et al. (1997). "Noninvasive imaging of in vivo blood flow velocity using optical Doppler tomography." *Optics Letters* 22(14): 1119-1121.

Chen, Z. P., Y. H. Zhao, et al. (1999). "Optical Doppler tomography." *Ieee Journal of Selected Topics in Quantum Electronics* 5(4): 1134-1142.

Cheong, W. F., S. A. Prahl, et al. (1990). "A Review of the Optical-Properties of Biological Tissues." *Ieee Journal of Quantum Electronics* 26(12): 2166-2185.

Chernikov, S. V., Y. Zhu, et al. (1997). "Supercontinuum self-Q-switched ytterbium fiber laser." *Optics Letters* 22(5): 298-300.

Cho, S. H., B. E. Bouma, et al. (1999). "Low-repetition-rate high-peak-power Kerr-lens mode-locked Ti:Al/sub 2/0/sub 3/ laser with a multiple-pass cavity." *Optics Letters* 24(6): 417-419.

Choma, M. A., M. V. Sarunic, et al. (2003). "Sensitivity advantage of swept source and Fourier domain optical coherence tomography." *Optics Express* 11(18): 2183-2189.

Choma, M. A., C. H. Yang, et al. (2003). "Instantaneous quadrature low-coherence interferometry with 3×3 fiber-optic couplers." *Optics Letters* 28(22): 2162-2164.

Choplin, N. T. and D. C. Lundy (2001). "The sensitivity and specificity of scanning laser polarimetry in the detection of glaucoma in a clinical setting." *Ophthalmology* 108 (5): 899-904.

Christens Barry, W. A., W. J. Green, et al. (1996). "Spatial mapping of polarized light transmission in the central rabbit cornea." *Experimental Eye Research* 62(6): 651-662.

Chvapil, M., D. P. Speer, et al. (1984). "Identification of the depth of burn injury by collagen stainability." *Plastic & Reconstructive Surgery* 73(3): 438-41.

Cioffi, G. A. (2001). "Three common assumptions about ocular blood flow and glaucoma." *Survey of Ophthalmology* 45: S325-S331.

Coleman, A. L. (1999). "Glaucoma." *Lancet* 354(9192): 1803-10.

Collaborative Normal-Tension Glaucoma Study Group (1998). "Comparison of Glaucomatous Progression Between Untreated Patients With Normal Tension Glaucoma and Patients with Therapeutically Reduced Intraocular Pressures." *Am J Ophthalmol* 126: 487-97.

Collaborative Normal-Tension Glaucoma Study Group (1998). "The effectiveness of intraocular pressure reduction in the treatment of normal-tension glaucoma." *Am J Ophthalmol* 126: 498-505.

Collaborative Normal-Tension Glaucoma Study Group (2001). "Natural History of Normal-Tension Glaucoma." *Ophthalmology* 108: 247-253.

Colston, B. W., M. J. Everett, et al. (1998). "Imaging of hard- and soft-tissue structure in the oral cavity by optical coherence tomography." *Applied Optics* 37(16): 3582-3585.

Colston, B. W., U. S. Sathyam, et al. (1998). "Dental OCT." *Optics Express* 3(6): 230-238.

Congdon, N. G., D. S. Friedman, et al. (2003). "Important causes of visual impairment in the world today." *Jama-Journal of the American Medical Association* 290(15): 2057-2060.

Cregan, R. F., B. J. Mangan, et al. (1999). "Single-mode photonic band gap guidance of light in air." *Science* 285(5433): 1537-1539.

DalMolin, M., A. Galtarossa, et al. (1997). "Experimental investigation of linear polarization in high-birefringence single-mode fibers." *Applied Optics* 36(12): 2526-2528.

Danielson, B. L. and C. D. Whittenberg (1987). "Guided-Wave Reflectometry with Micrometer Resolution." *Applied Optics* 26(14): 2836-2842.

Dave, D. P. and T. E. Milner (2000). "Doppler-angle measurement in highly scattering media." *Optics Letters* 25(20): 1523-1525.

de Boer, J. F., T. E. Milner, et al. (1998). *Two dimensional birefringence imaging in biological tissue using phase and polarization sensitive optical coherence tomography*. Trends in Optics and Photonics (TOPS): Advances in Optical Imaging and Photon Migration, Orlando, USA, Optical Society of America, Washington, DC 1998.

de Boer, J. F., C. E. Saxer, et al. (2001). "Stable carrier generation and phase-resolved digital data processing in optical coherence tomography." *Applied Optics* 40(31): 5787-5790.

Degroot, P. and L. Deck (1993). "3-Dimensional Imaging by Sub-Nyquist Sampling of White-Light Interferograms." *Optics Letters* 18(17): 1462-1464.

Denk, W., J. H. Strickler, et al. (1990). "2-Photon Laser Scanning Fluorescence Microscopy." *Science* 248(4951): 73-76.

Descour, M. R., A. H. O. Karkkainen, et al. (2002). "Toward the development of miniaturized Imaging systems for detection of pre-cancer." *Ieee Journal of Quantum Electronics* 38(2): 122-130.

Dettwiller, L. (1997). "Polarization state interference: A general investigation." *Pure and Applied Optics* 6(1): 41-53.

DiCarlo, C. D., W. P. Roach, et al. (1999). "Comparison of optical coherence tomography imaging of cataracts with histopathology." *Journal of Biomedical Optics* 4.

Ding, Z., Y. Zhao, et al. (2002). "Real-time phase-resolved optical coherence tomography and optical Doppler tomography." *Optics Express* 10(5): 236-245.

Dobrin, P. B. (1996). "Effect of histologic preparation on the cross-sectional area of arterial rings." *Journal of Surgical Research* 61(2): 413-5.

Donohue, D. J., B. J. Stoyanov, et al. (1995). "Numerical Modeling of the Corneas Lamellar Structure and Birefringence Properties." *Journal of the Optical Society of America a-Optics Image Science and Vision* 12(7): 1425-1438.

Doornbos, R. M. P., R. Lang, et al. (1999). "The determination of in vivo human tissue optical properties and absolute chromophore concentrations using spatially resolved steady-state diffuse reflectance spectroscopy." *Physics in Medicine and Biology* 44(4): 967-981.

Drexler, W., A. Baumgartner, et al. (1997). "Biometric investigation of changes in the anterior eye segment during accommodation." *Vision Research* 37(19): 2789-2800.

Drexler, W., A. Baumgartner, et al. (1997). "Submicrometer precision biometry of the anterior segment of the human eye." *Investigative Ophthalmology & Visual Science* 38(7): 1304-1313.

Drexler, W., A. Baumgartner, et al. (1998). "Dual beam optical coherence tomography: signal identification for ophthalmologic diagnosis." *Journal of Biomedical Optics* 3 (1): 55-65.

Drexler, W., O. Findl, et al. (1998). "Partial coherence interferometry: A novel approach to biometry in cataract surgery." *American Journal of Ophthalmology* 126(4): 524-534.

Drexler, W., O. Findl, et al. (1997). "Clinical feasibility of dual beam optical coherence topography and tomography for ophthalmologic diagnosis." *Investigative Ophthalmology & Visual Science* 38(4): 1038-1038.

Drexler, W., C. K. Hitzenberger, et al. (1998). "Investigation of dispersion effects in ocular media by multiple wavelength partial coherence interferometry." *Experimental Eye Research* 66(1): 25-33.

Drexler, W., C. K. Hitzenberger, et al. (1996). "(Sub)micrometer precision biometry of the human eye by optical coherence tomography and topography." *Investigative Ophthalmology & Visual Science* 37(3): 4374-4374.

Drexler, W., C. K. Hitzenberger, et al. (1995). "Measurement of the Thickness of Fundus Layers by Partial Coherence Tomography." *Optical Engineering* 34(3): 701-710.

Drexler, W., U. Morgner, et al. (2001). "Ultrahigh-resolution ophthalmic optical coherence tomography." *Nature Medicine* 7(4): 502-507.

Drexler, W., U. Morgner, et al. (2001). "Ultrahigh-resolution ophthalmic optical coherence tomography. [erratum appears in Nat Med May 2001;7(5):636.]." *Nature Medicine* 7(4): 502-7.

Drexler, W., H. Sattmann, et al. (2003). "Enhanced visualization of macular pathology with the use of ultrahigh-resolution optical coherence tomography." *Archives of Ophthalmology* 121(5): 695-706.

Drexler, W., D. Stamper, et al. (2001). "Correlation of collagen organization with polarization sensitive imaging of in vitro cartilage: implications for osteoarthritis." *Journal of Rheumatology* 28(6): 1311-8.

Droog, E. J., W. Steenbergen, et al. (2001). "Measurement of depth of burns by laser Doppler perfusion imaging." *Burns* 27(6): 561-8.

Dubois, A., K. Grieve, et al. (2004). "Ultrahigh-resolution full-field optical coherence tomography." *Applied Optics* 43(14): 2874-2883.

Dubois, A., L. Vabre, et al. (2002). "High-resolution full-field optical coherence tomography with a Linnik microscope." *Applied Optics* 41(4): 805-812.

Ducros, M., M. Laubscher, et al. (2002). "Parallel optical coherence tomography in scattering.samples using a two-dimensional smart-pixel detector array." *Optics Communications* 202(1-3): 29-35.

Ducros, M. G., J. D. Marsack, et al. (2001). "Primate retina imaging with polarization-sensitive optical coherence tomography." *Journal of the Optical Society of America a-Optics Image Science and Vision* 18(12): 2945-2956.

Duncan, A., J. H. Meek, et al. (1995). "Optical Pathlength Measurements on Adult Head, Calf and Forearm and the Head of the Newborn-Infant Using Phase-Resolved Optical Spectroscopy." *Physics in Medicine and Biology* 40(2): 295-304.

Eigensee, A., G. Haeusler, et al. (1996). "New method of short-coherence interferometry in human skin (in vivo) and in solid volume scatterers." *Proceedings of SPIE—The International Society for Optical Engineerinq* 2925: 169-178.

Eisenbeiss, W., J. Marotz, et al. (1999). "Reflection-optical multispectral imaging method for objective determination of burn depth." *Burns* 25(8): 697-704.

Elbaum, M., M. King, et al. (1972). "Wavelength-Diversity Technique for Reduction of Speckle Size." *Journal of the Optical Society of America* 62(5): 732-&.

Ervin, J. C., H. G. Lemij, et al. (2002). "Clinician change detection viewing longitudinal stereophotographs compared to confocal scanning laser tomography in the LSU Experimental Glaucoma (LEG) Study." *Ophthalmology* 109(3): 467-81.

Essenpreis, M., C. E. Elwell, et al. (1993). "Spectral Dependence of Temporal Point Spread Functions in Human Tissues." *Applied Optics* 32(4): 418-425.

Eun, H. C. (1995). "Evaluation of skin blood flow by laser Doppler flowmetry. [Review] [151 refs]." *Clinics in Dermatology* 13(4): 337-47.

Evans, J. A., J. M. Poneros, et al. (2004). "Application of a histopathologic scoring system to optical coherence tomography (OCT) images to identify high-grade dysplasia in Barrett's esophagus." *Gastroenterology* 126(4): A51-A51.

Feldchtein, F. I., G. V. Gelikonov, et al. (1998). "In vivo OCT imaging of hard and soft tissue of the oral cavity." *Optics Express* 3(6): 239-250.

Feldchtein, F. I., G. V. Gelikonov, et al. (1998). "Endscopic applications of optical coherence tomography." *Optics Express* 3(6): 257-270.

Fercher, A. F., W. Drexler, et al. (1997). "Optical ocular tomography." *Neuro—Ophthalmology* 18(2): 39-49.

Fercher, A. F., W. Drexler, et al. (1994). *Measurement of optical distances by optical spectrum modulation.* Proceedings of SPIE—The International Society for Optical Engineering.

Fercher, A. F., W. Drexler, et al. (2003). "Optical coherence tomography—principles and applications." *Reports on Progress in Physics* 66(2): 239-303.

Fercher, A. F., C. Hitzenberger, et al. (1991). "Measurement of Intraocular Optical Distances Using Partially Coherent Laser-Light." *Journal of Modern Optics* 38(7): 1327-1333.

Fercher, A. F., C. K. Hitzenberger, et al. (1996). *Ocular partial coherence interferometry.* Proceedings of SPIE—The International Society for Optical Engineering.

Fercher, A. F., C. K. Hitzenberger, et al. (1993). "In-Vivo Optical Coherence Tomography." *American Journal of Ophthalmology* 116(1): 113-115.

Fercher, A. F., C. K. Hitzenberger, et al. (1994). *In-vivo dual-beam optical coherence tomography.* Proceedings of SPIE—The International Society for Optical Engineering.

Fercher, A. F., C. K. Hitzenberger, et al. (1995). "Measurement of Intraocular Distances by Backscattering Spectral Interferometry." *Optics Communications* 117(1-2): 43-48.

Fercher, A. F., C. K. Hitzenberger, et al. (2000). "A thermal light source technique for optical coherence tomography." *Optics Communications* 185(1-3): 57-64.

Fercher, A. F., C. K. Hitzenberger, et al. (2001). "Numerical dispersion compensation for Partial Coherence Interferometry and Optical Coherence Tomography." *Optics Express* 9(12): 610-615.

Fercher, A. F., C. K. Hitzenberger, et al. (2002). "Dispersion compensation for optical coherence tomography depth—scan signals by a numerical technique." *Optics Communications* 204(1-6): 67-74.

Fercher, A. F., H. C. Li, et al. (1993). "Slit Lamp Laser-Doppler Interferometer." *Lasers in Surgery and Medicine* 13(4): 447-452.

Fercher, A. F., K. Mengedoht, et at. (1988). "Eye-Length Measurement by Interferometry with Partially Coherent-Light." *Optics Letters* 13(3): 186-188.

Ferro, P., M. Haelterman, et al. (1991). "All-Optical Polarization Switch with Long Low-Birefringence Fiber." *Electronics Letters* 27(16): 1407-1408.

Fetterman, M. R., D. Goswami, et al. (1998). "Ultrafast pulse shaping: amplification and characterization." *Optics Express* 3(10): 366-375.

Findl, O., W. Drexler, et al. (2001). "Improved prediction of intraocular lens power using partial coherence interferometry." *Journal of Cataract and Refractive Surgery* 27 (6): 861-867.

Fork, R. L., C. H. B. Cruz, et al. (1987). "Compression of Optical Pulses to 6 Femtoseconds by Using Cubic Phase Compensation." *Optics Letters* 12(7): 483-485.

Foschini, G. J. and C. D. Poole (1991). "Statistical-Theory of Polarization Dispersion in Single-Mode Fibers." *Journal of Lightwave Technology* 9(11): 1439-1456.

Francia, C., F. Bruyere, et al. (1998). "PMD second-order effects on pulse propagation in single-mode optical fibers." *Ieee Photonics Technology Letters* 10(12): 1739-1741.

Fried, D., R. E. Glena, et al. (1995). "Nature of Light-Scattering in Dental Enamel and Dentin at Visible and near-Infrared Wavelengths." *Applied Optics* 34(7): 1278-1285.

Fujimoto, J. G., M. E. Brezinski, et al. (1995). "Optical Biopsy and Imaging Using Optical Coherence Tomography." *Nature Medicine* 1(9): 970-972.

Fukasawa, A. and H. Iijima (2002). "Optical coherence tomography of choroidal osteoma." *American Journal of Ophthalmology* 133(3): 419-21.

Fymat, A. L. (1981). "High-Resolution Interferometric Spectrophotopolarimetry." *Optical Engineering* 20(1): 25-30.

Galtarossa, A., L. Palmieri, et al. (2000). "Statistical characterization of fiber random birefringence." *Optics Letters* 25(18): 1322-1324.

Galtarossa, A., L. Palmieri, et al. (2000). "Measurements of beat length and perturbation length in long single-mode fibers." *Optics Letters* 25(6): 384-386.

Gandjbakhche, A. H., P. Mills, et al. (1994). "Light-Scattering Technique for the Study of Orientation and Deformation of Red-Blood-Cells in a Concentrated Suspension." *Applied Optics* 33(6): 1070-1078.

Garcia, N. and M. Nieto-Vesperinas (2002). "Left-handed materials do not make a perfect lens." *Physical Review Letters* 88(20).

Gelikonov, V. M., G. V. Gelikonov, et al. (1995). "Coherent Optical Tomography of Microscopic Inhomogeneities in Biological Tissues." *Jetp Letters* 61(2): 158-162.

George, N. and A. Jain (1973). "Speckle Reduction Using Multiple Tones of Illumination." *Applied Optics* 12(6): 1202-1212.

Gibson, G. N., R. Klank, et al. (1996). "Electro-optically cavity-dumped ultrashort-pulse Ti:sapphire oscillator." *Optics Letters* 21(14): 1055.

Gil, J. J. (2000). "Characteristic properties of Mueller matrices." *Journal of the Optical Society of America a-Optics Image Science and Vision* 17(2): 328-334.

Gil, J. J. and E. Bernabeu (1987). "Obtainment of the Polarizing and Retardation Parameters of a Nondepolarizing Optical-System from the Polar Decomposition of Its Mueller Matrix." *Optik* 76(2): 67-71.

Gladkova, N. D., G. A. Petrova, et al. (2000). "In vivo optical coherence tomography imaging of human skin: norm and pathology." *Skin Research and Technology* 6 (1): 6-16.

Glaessl, A., A. G. Schreyer, et al. (2001). "Laser surgical planning with magnetic resonance imaging-based 3-dimensional reconstructions for intralesional Nd:YAG laser therapy of a venous malformation of the neck." *Archives of Dermatology* 137(10): 1331-1335.

Gloesmann, M., B. Hermann, et al. (2003). "Histologic correlation of pig retina radial stratification with ultrahigh-resolution optical coherence tomography." *Investigative Ophthalmology & Visual Science* 44(4): 1696-1703.

Goldberg, L. and D. Mehuys (1994). "High-Power Superluminescent Diode Source." *Electronics Letters* 30(20): 1682-1684.

Goldsmith, J. A., Y. Li, et al. (2005). "Anterior chamber width measurement by high speed optical coherence tomography." *Ophthalmology* 112(2): 238-244.

Goldstein, L. E., J. A. Muffat, et al. (2003). "Cytosolic beta-amyloid deposition and supranuclear cataracts in lenses from people with Alzheimer's disease." *Lancet* 361(9365): 1258-1265.

Golubovic, B., B. E. Bouma, et al. (1996). "Thin crystal, room-temperature Cr/sup 4 +/:forstefite laser using near-infrared pumping." *Optics Letters* 21(24): 1993-1995.

Gonzalez, S. and Z. Tannous (2002). "Real-time, in vivo confocal reflectance microscopy of basal cell carcinoma." *Journal of the American Academy of Dermatology* 47(6): 869-874.

Gordon, M. O. and M. A. Kass (1999). "The Ocular Hypertension Treatment Study: design and baseline description of the participants." *Archives of Ophthalmology* 117(5): 573-83.

Grayson, T. P., J. R. Torgerson, et al. (1994). "Observation of a Nonlocal Pancharatnam Phase-Shift in the Process of Induced Coherence without Induced Emission." *Physical Review* A 49(1): 626-628.

Greaney, M. J., D. C. Hoffman, et al. (2002). "Comparison of optic nerve imaging methods to distinguish normal eyes from those with glaucoma." *Investigative Ophthalmology & Visual Science* 43(1): 140-5.

Greenfield, D. S., H. Bagga, et al. (2003). "Macular thickness changes in glaucomatous optic neuropathy detected using optical coherence tomography." *Archives of Ophthalmology* 121(1): 41-46.

Greenfield, D. S., R. W. Knighton, et al. (2000). "Effect of corneal polarization axis on assessment of retinal nerve fiber layer thickness by scanning laser polarimetry." *American Journal of Ophthalmology* 129(6): 715-722.

Griffin, R. A., D. D. Sampson, et al. (1995). "Coherence Coding for Photonic Code-Division Multiple-Access Networks." *Journal of Lightwave Technology* 13(9): 1826-1837.

Guedes, V., J. S. Schuman, et al. (2003). "Optical coherence tomography measurement of macular and nerve fiber layer thickness in normal and glaucomatous human eyes." *Ophthalmology* 110(1): 177-189.

Gueugniaud, P. Y., H. Carsin, et al. (2000). "Current advances in the initial management of major thermal burns. [Review] [76 refs]." *Intensive Care Medicine* 26(7): 848-56.

Guido, S. and R. T. Tranquillo (1993). "A Methodology for the Systematic and Quantitative Study of Cell Contact Guidance in Oriented Collagen Gels—Correlation of Fibroblast Orientation and Gel Birefringence." *Journal of Cell Science* 105: 317-331.

Gurses-Ozden, R., H. Ishikawa, et al. (1999). "Increasing sampling density improves reproducibility of optical coherence tomography measurements." *Journal of Glaucoma* 8(4): 238-41.

Guzzi, R. (1998). "Scattering Theory from Homogeneous and Coated Spheres." 1-11.

Haberland, U. B., Vladimir; Schmitt, Hans J. (1996). "Optical coherent tomography of scattering media using electrically tunable near-infrared semiconductor laser." *Applied Optics* Draft Copy.

Haberland, U. R., Walter; Blazek, Vladimir; Schmitt, Hans J. (1995). "Investigation of highly scattering media using near-infrared continuous wave tunable semiconductor laser." *Proc. SPIE*, 2389: 503-512.

Hale, G. M. and M. R. Querry (1973). "Optical-Constants of Water in 200-Nm to 200-Mum Wavelength Region." *Applied Optics* 12(3): 555-563.

Hammer, D. X., R. D. Ferguson, et al. (2002). "Image stabilization for scanning laser ophthalmoscopy." *Optics Express* 10(26): 1542.

Hara, T., Y. Ooi, et al. (1989). "Transfer Characteristics of the Microchannel Spatial Light-Modulator." *Applied Optics* 28(22): 4781-4786.

Harland, C. C., S. G. Kale, et al. (2000). "Differentiation of common benign pigmented skin lesions from melanoma by high-resolution ultrasound." *British Journal of Dermatology* 143(2): 281-289.

Hartl, I., X. D. Li, et al. (2001). "Ultrahigh-resolution optical coherence tomography using continuum generation in an air-silica microstructure optical fiber." *Optics Letters* 26(9): 608-610.

Hassenstein, A., A. A. Bialasiewicz, et al. (2000). "Optical coherence tomography in uveitis patients." *American Journal of Ophthalmology* 130(5): 669-70.

Hattenhauer, M. G., D. H. Johnson, et al. (1998). "The probability of blindness from open-angle glaucoma. [see comments]." *Ophthalmology* 105(11): 2099-104.

Hausler, G., J. M. Herrmann, et al. (1996). "Observation of light propagation in volume scatterers with 10(11)-fold slow motion." *Optics Letters* 21(14): 1087-1089.

Hazebroek, H. F. and A. A. Holscher (1973). "Interferometric Ellipsometry." *Journal of Physics E-Scientific Instruments* 6(9): 822-826.

Hazebroek, H. F. and W. M. Visser (1983). "Automated Laser Interferometric Ellipsometry and Precision Reflectometry." *Journal of Physics E-Scientific Instruments* 16(7): 654-661.

He, Z. Y., N. Mukohzaka, et al. (1997). "Selective image extraction by synthesis of the coherence function using two-dimensional optical lock-in amplifier with microchannel spatial light modulator." *Ieee Photonics Technology Letters* 9(4): 514-516.

Hee, M. R., J. A. Izatt, et al. (1993). "Femtosecond Transillumination Optical Coherence Tomography." *Optics Letters* 18(12): 950-952.

Hee, M. R., J. A. Izatt, et al. (1995). "Optical coherence tomography of the human retina." *Archives of Ophthalmology* 113(3): 325-32.

Hee, M. R., C. A. Puliafito, et al. (1998). "Topography of diabetic macular edema with optical coherence tomography." *Ophthalmology* 105(2): 360-70.

Hee, M. R., C. A. Puliafito, et al. (1995). "Quantitative assessment of macular edema with optical coherence tomography." *Archives of Ophthalmoloqy* 113(8): 1019-29.

Hellmuth, T. and M. Welle (1998). "Simultaneous measurement of dispersion, spectrum, and distance with a fourier transform spectrometer." *Journal of Biomedical Optics* 3(1): 7-11.

Hemenger, R. P. (1989). "Birefringence of a medium of tenuous parallel cylinders." *Applied Optics* 28(18): 4030-4034.

Henry, M. (1981). "Fresnel-Arago Laws for Interference in Polarized-Light—Demonstration Experiment." *American Journal of Physics* 49(7): 690-691.

Herz, P. R., Y. Chen, et al. (2004). "Micromotor endoscope catheter for in vivo, ultrahigh-resolution optical coherence tomography." *Optics Letters* 29(19): 2261-2263.

Hirakawa, H., H. Iijima, et al. (1999). "Optical coherence tomography of cystoid macular edema associated with *Retinitis pigmentosa*." *American Journal of Ophthalmology* 128(2): 185-91.

Hitzenberger, C. K., A. Baumgartner, et al. (1994). "Interferometric Measurement of Corneal Thickness with Micrometer Precision." *American Journal of Ophthalmology* 118(4): 468-476.

Hitzenberger, C. K., A. Baumgartner, et al. (1999). "Dispersion effects in partial coherence interferometry: Implications for intraocular ranging." *Journal of Biomedical Optics* 4(1): 144-151.

Hitzenberger, C. K., A. Baumgartner, et al. (1998). "Dispersion induced multiple signal peak splitting in partial coherence interferometry." *Optics Communications* 154 (4): 179-185.

Hitzenberger, C. K., M. Danner, et al. (1999). "Measurement of the spatial coherence of superluminescent diodes." *Journal of Modern Optics* 46(12): 1763-1774.

Hitzenberger, C. K. and A. F. Fercher (1999). "Differential phase contrast in optical coherence tomography." *Optics Letters* 24(9): 622-624.

Hitzenberger, C. K., M. Sticker, et al. (2001). "Differential phase measurements in low-coherence interferometry without 2 pi ambiguity." *Optics Letters* 26(23): 1864-1866.

Hoeling, B. M., A. D. Fernandez, et al. (2000). "An optical coherence microscope for 3-dimensional imaging in developmental biology." *Optics Express* 6(7): 136-146.

Hoerauf, H., C. Scholz, et al. (2002). "Transscleral optical coherence tomography: a new imaging method for the anterior segment of the eye." *Archives of Ophthalmology* 120(6): 816-9.

Hoffmann, K., M. Happe, et al. (1998). "Optical coherence tomography (OCT) in dermatology." *Journal of Investigative Dermatology* 583-583.

Hoh, S. T., D. S. Greenfield, et al. (2000). "Optical coherence tomography and scanning laser polarimetry in normal, ocular hypertensive, and glaucomatous eyes." *American Journal of Ophthalmology* 129(2): 129-35.

Hohenleutner, U., M. Hilbert, et al. (1995). "Epidermal Damage and Limited Coagulation Depth with the Flashlamp-Pumped Pulsed Dye-Laser—a Histochemical-Study." *Journal of Investigative Dermatology* 104(5): 798-802.

Holland, A. J. A., H. C. O. Martin, et al. (2002). "Laser Doppler imaging prediction of burn wound outcome in children." *Burns* 28(1): 11-17.

Hotate, K. and T. Okugawa (1994). "Optical Information-Processing by Synthesis of the Coherence Function." *Journal of Lightwave Technology* 12(7): 1247-1255.

Hourdakis, C. J. and A. Perris (1995). "A Monte-Carlo Estimation of Tissue Optical-Properties for Use in Laser Dosimetry." *Physics in Medicine and Biology* 40(3): 351-364.

Hu, Z., F. Li, et al. (2000). "Wavelength-tunable narrow-linewidth semiconductor fiber-ring laser." *IEEE Photonics Technology Letters* 12(8): 977-979.

Huang, F., W. Yang, et al. (2001). "Quadrature spectral interferometric detection and pulse shaping." *Optics Letters* 26(6): 382-384.

Huang, X. R. And R. W. Knighton (2002). "Linear birefringence of the retinal nerve fiber layer measured in vitro with a multispectral imaging micropolarimeter." *Journal of Biomedical Optics* 7(2): 199-204.

Huber, R., M. Wojtkowski, et al. (2005). "Amplified, frequency swept lasers for frequency domain reflectometry and OCT imaging: design and scaling principles." *Optics Express* 13(9): 3513-3528.

Hunter, D. G., J. C. Sandruck, et al. (1999). "Mathematical modeling of retinal birefringence scanning." *Journal of the Optical Society of America a-Optics Image Science and Vision* 16(9): 2103-2111.

Hurwitz, H. H. and R. C. Jones (1941). "A new calculus for the treatment of optical systems II. Proof of three general equivalence theorems." *Journal of the Optical Society of America* 31(7): 493-499.

Huttner, B., C. De Barros, et al. (1999). "Polarization-induced pulse spreading in birefringent optical fibers with zero differential group delay." *Optics Letters* 24(6): 370-372.

Huttner, B., B. Gisin, et al. (1999). "Distributed PMD measurement with a polarization-OTDR in optical fibers." *Journal of Lightwave Technology* 17(10): 1843-1848.

Huttner, B., J. Reecht, et al. (1998). "Local birefringence measurements in single-mode fibers with coherent optical frequency-domain reflectometry." *Ieee Photonics Technology Letters* 10(10): 1458-1460.

Hyde, S. C. W., N. P. Barry, et al. (1995). "Sub-100-Mu-M Depth-Resolved Holographic Imaging through Scattering Media in the near-Infrared." *Optics Letters* 20(22): 2330-2332.

Hyde, S. C. W., N. P. Barry, et al. (1995). "Depth-Resolved Holographic Imaging through Scattering Media by Photorefraction." *Optics Letters* 20(11): 1331-1333.

Iftimia, N. V., B. E. Bouma, et al. (2004). "Adaptive ranging for optical coherence tomography." *Optics Express* 12(17): 4025-4034.

Iida, T., N. Hagimura, et al. (2000). "Evaluation of central serous chorioretinopathy with optical coherence tomography." *American Journal of Ophthalmology* 129(1): 16-20.

Imai, M., H. Iijima, et al. (2001). "Optical coherence tomography of tractional macular elevations in eyes with proliferative diabetic retinopathy. [republished in Am J Ophthalmol. Sep. 2001;132(3):458-61 ; 11530091.]." *American Journal of Ophthalmology* 132(1): 81-4.

Indebetouw, G. and P. Klysubun (2000). "Imaging through scattering media with depth resolution by use of low-coherence gating in spatiotemporal digital holography." *Optics Letters* 25(4): 212-214.

Ip, M. S., B. J. Baker, et al. (2002). "Anatomical outcomes of surgery for idiopathic macular hole as determined by optical coherence tomography." *Archives of Ophthalmology* 120(1): 29-35.

Ismail, R., V. Tanner, et al. (2002). "Optical coherence tomography imaging of severe commotio retinae and associated macular hole." *British Journal of Ophthalmology* 86(4): 473-4.

Izatt, J. A., M. R. Hee, et al. (1994). "Optical Coherence Microscopy in Scattering Media." *Optics Letters* 19(8): 590-592.

Izatt, J. A., M. R. Hee, et al. (1994). "Micrometer-scale resolution imaging of the anterior eye in vivo with optical coherence tomography." *Archives of Ophthalmology* 112 (12): 1584-9.

Izatt, J. A., M. D. Kulkami, et al. (1997). "In vivo bidirectional color Doppler flow imaging of picoliter blood volumes using optical coherence tomography." *Optics Letters* 22(18): 1439-1441.

Izatt, J. A., M. D. Kulkarni, et al. (1996). "Optical coherence tomography and microscopy in gastrointestinal tissues." *IEEE Journal of Selected Topics in Quantum Electronics* 2(4): 1017.

Jacques, S. L., J. S. Nelson, et al. (1993). "Pulsed Photothermal Radiometry of Port-Wine-Stain Lesions." *Applied Optics* 32(13): 2439-2446.

Jacques, S. L., J. R. Roman, et al. (2000). "Imaging superficial tissues with polarized light." *Lasers in Surgery and Medicine* 26(2): 119-129.

Jang, I. K., B. E. Bouma, et al. (2002). "Visualization of coronary atherosclerotic plaques in patients using optical coherence tomography: Comparison with intravascular ultrasound." *Journal of the American College of Cardiology* 39(4): 604-609.

Jang, I. K., B. D. MacNeill, et al. (2002). "In-vivo characterization of coronary plaques in patients with ST elevation acute myocardial infarction using optical coherence tomography (OCT)." *Circulation* 106(19): 698-698 3440 Suppl. S.

Jang, I. K., G. J. Tearney, et al. (2000). "Comparison of optical coherence tomography and intravascular ultrasound for detection of coronary plaques with large lipid-core in living patients." *Circulation* 102(18): 509-509.

Jeng, J. C., A. Bridgeman, et al. (2003). "Laser Doppler imaging determines need for excision and grafting in advance of clinical judgment: a prospective blinded trial." *Burns* 29(7): 665-670.

Jesser, C. A., S. A. Boppart, et al. (1999). "High resolution imaging of transitional cell carcinoma with optical coherence tomography: feasibility for the evaluation of bladder pathology." *British Journal of Radiology* 72: 1170-1176.

Johnson, C. A., J. L. Keltner, et al. (2002). "Baseline visual field characteristics in the ocular hypertension treatment study." *Ophthalmology* 109(3): 432-7.

Jones, R. C. (1941). "A new calculus for the treatment of optical systems III. The Sohncke theory of optical activity." *Journal of the Optical Society of America* 31 (7): 500-503.

Jones, R. C. (1941). "A new calculus for the treatment of optical systems I. Description and discussion of the calculus." *Journal of the Optical Society of America* 31(7): 488-493.

Jones, R. C. (1942). "A new calculus for the treatment of optical systems. IV." *Journal of the Optical Society of America* 32(8): 486-493.

Jones, R. C. (1947). "A New Calculus for the Treatment of Optical Systems .6. Experimental Determination of the Matrix." *Journal of the Optical Society of America* 37(2): 110-112.

Jones, R. C. (1947). "A New Calculus for the Treatment of Optical Systems .5. A More General Formulation, and Description of Another Calculus." *Journal of the Optical Society of America* 37(2): 107-110.

Jones, R. C. (1948). "A New Calculus for the Treatment of Optical Systems .7. Properties of the N-Matrices." *Journal of the Optical Society of America* 38(8): 671-685.

Jones, R. C. (1956). "New Calculus for the Treatment of Optical Systems .8. Electromagnetic Theory." *Journal of the Optical Society of America* 46(2): 126-131.

Jopson, R. MThe ., L. E. Nelson, et al. (1999). "Measurement of second-order polarization-mode dispersion vectors in optical fibers." *Ieee Photonics Technology Letters* 11 (9): 1153-1155.

Jost, B. M., A. V. Sergienko, et al. (1998). "Spatial correlations of spontaneously down-converted photon pairs detected with a single-photon-sensitive CCD camera." *Optics Express* 3(2): 81-88.

Kaplan, B., E. Compain, et al. (2000). "Phase-modulated Mueller ellipsometry characterization of scattering by latex sphere suspensions." *Applied Optics* 39 (4): 629-636.

Kass, M. A., D. K. Heuer, et al. (2002). "The Ocular Hypertension Treatment Study: a randomized trial determines that topical ocular hypotensive medication delays or prevents the onset of primary open-angle glaucoma." *Archives of Ophthalmology* 120(6): 701-13; discussion 829-30.

Kasuga, Y., J. Arai, et al. (2000). "Optical coherence tomograghy to confirm early closure of macular holes." *American Journal of Ophthalmology* 130(5): 675-6.

Kaufman, T., S. N. Lusthaus, et al. (1990). "Deep Partial Skin Thickness Burns—a Reproducible Animal-Model to Study Burn Wound-Healing." *Burns* 16(1): 13-16.

Kemp, N. J., J. Park, et al. (2005). "High-sensitivity determination of birefringence in turbid media with enhanced polarization-sensitive optical coherence tomography." *Journal of the Optical Society of America a-Optics Image Science and Vision* 22(3): 552-560.

Kerrigan-Baumrind, L. A., H. A. Quigley, et al. (2000). "Number of ganglion cells in glaucoma eyes compared with threshold visual field tests in the same persons." *Investigative Ophthalmology & Visual Science* 41(3): 741-8.

Kesen, M. R., G. L. Spaeth, et al. (2002). "The Heidelberg Retina Tomograph vs clinical impression in the diagnosis of glaucoma." *American Journal of Ophthalmology* 133(5): 613-6.

Kienle, A. and R. Hibst (1995). "A New Optimal Wavelength for Treatment of Port-Wine Stains." *Physics in Medicine and Biology* 40(10): 1559-1576.

Kienle, A., L. Lilge, et al. (1996). "Spatially resolved absolute diffuse reflectance measurements for noninvasive determination of the optical scattering and absorption coefficients of biological tissue." *Applied Optics* 35(13): 2304-2314.

Kim, B. Y. and S. S. Choi (1981). "Analysis and Measurements of Birefringence in Single-Mode Fibers Using the Backscattering Method." *Optics Letters* 6(11): 578-580.

Kimel, S., L. 0. Svaasand, et al. (1994). "Differential Vascular-Response to Laser Photothermolysis." *Journal of Investigative Dermatology* 103(5): 693-700.

Kloppenberg, F. W. H., G. Beerthuizen, et al. (2001). "Perfusion of burn wounds assessed by Laser Doppler Imaging is related to burn depth and healing times." *Burns* 27(4): 359-363.

Knighton, R. W. and X. R. Huang (2002). "Analytical methods for scanning laser polarimetry." *Optics Express* 10(21): 1179-1189.

Knighton, R. W., X. R. Huang, et al. (2002). "Analytical model of scanning laser polarimetry for retinal nerve fiber layer assessment." *Investigative Ophthalmology & Visual Science* 43(2): 383-392.

Knuettel, A. R. S., Joseph M.: Shay, M.; "Stationary low-coherence light imaging and spectroscopy using a CCD camera." *Proc. SPIE*, vol. 2135: p. 239-250.

Knuttel, A. and M. Boehlau-Godau (2000). "Spatially confined and temporally resolved refractive index and scattering evaluation in human skin performed with optical coherence tomography." *Journal of Biomedical Optics* 5(1): 83-92.

Knuttel, A. and J. M. Schmitt (1993). "Stationary Depth-Profiling Reflectometer Based on Low-Coherence Interferometry." *Optics Communications* 102(3-4): 193-198.

Knuttel, A., J. M. Schmitt, et al. (1994). "Low-Coherence Reflectometry for Stationary Lateral and Depth Profiling with Acoustooptic Deflectors and a Ccd Camera." *Optics Letters* 19(4): 302-304.

Kobayashi, M., H. Hanafusa, et al. (1991). "Polarization-Independent Interferometric Optical-Time-Domain Reflectometer." *Journal of Lightwave Technology* 9(5): 623-628.

Kolios, M. C., M. D. Sherar, et al. (1995). "Large Blood-Vessel Cooling in Heated Tissues—a Numerical Study." *Physics in Medicine and Biology* 40(4): 477-494.

Koozekanani, D., K. Boyer, et al. (2001). "Retinal thickness measurements from optical coherence tomography using a Markov boundary model." *Ieee Transactions on Medical Imaging* 20(9): 900-916.

Kop, R. H. J. and R. Sprik (1995). "Phase-sensitive interferometry with ultrashort optical pulses." *Review of Scientific Instruments* 66(12): 5459-5463.

Kramer, R. Z., J. Bella, et al. (1999). "Sequence dependent conformational variations of collagen triple-helical structure." *Nature Structural Biology* 6(5): 454-7.

Kulkarni, M. D., T. G. van Leeuwen, et al. (1998). "Velocity-estimation accuracy and frame-rate limitations in color Doppler optical coherence tomography." *Optics Letters* 23(13): 1057-1059.

Kwon, Y. H., C. S. Kim, et al. (2001). "Rate of visual field loss and long-term visual outcome in primary open-angle glaucoma." *American Journal of Ophthalmology* 132(1): 47-56.

Kwong, K. F., D. Yankelevich, et al. (1993). "400-Hz Mechanical Scanning Optical Delay-Line." *Optics Letters* 18(7): 558-560.

Landers, J., I. Goldberg, et al. (2002). "Analysis of risk factors that may be associated with progression from ocular hypertension to primary open angle glaucoma." *Ophthalmogy* 30(4): 242-7.

Laszlo, A. and A. Venetianer (1998). Heat resistance in mammalian cells: Lessons and challenges. *Stress of Life*. 851: 169-178.

Laszlo, A. and A. Venetianer (1998). "Heat resistance in mammalian cells: lessons and challenges.[Review] [52 refs]." *Annals of the New York Academy of Sciences* 851: 169-78.

Laufer, J., R. Simpson, et al. (1998). "Effect of temperature on the optical properties of ex vivo human dermis and subdermis." *Physics in Medicine and Biology* 43(9): 2479-2489.

Lederer, D. E., J. S. Schuman, et al. (2003). "Analysis of macular volume in normal and glaucomatous eyes using optical coherence tomography." *American Journal of Ophthalmology* 135(6): 838-843.

Lee, P. P., Z. W. Feldman, et al. (2003). "Longitudinal prevalence of major eye diseases." *Archives of Ophthalmology* 121(9): 1303-1310.

Lehrer, M. S., T. T. Sun, et al. (1998). "Strategies of epithelial repair: modulation of stem cell and transit amplifying cell proliferation." *Journal of Cell Science* 111(Pt 19): 2867-75.

Leibowitz, H. M., D. E. Krueger, et al. (1980). "The Framingham Eye Study monograph: An ophthalmological and epidemiological study of cataract, glaucoma, diabetic retinopathy, macular degeneration, and visual acuity in a general population of 2631 adults, 1973-1975." *Survey of Ophthalmology* 24(Suppl): 335-610.

Leitgeb, R., C. K. Hitzenberger, et al. (2003). "Performance of fourier domain vs. time domain optical coherence tomography." *Optics Express* 11(8): 889-894.

Leitgeb, R., L. F. Schmetterer, et al. (2002). "Flow velocity measurements by frequency domain short coherence interferometry." *Proc. SPIE* 4619: 16-21.

Leitgeb, R. A., W. Drexler, et al. (2004). "Ultrahigh resolution Fourier domain optical coherence tomography." *Optics Express* 12(10): 2156-2165.

Leitgeb, R. A., C. K. Hitzenberger, et al. (2003). "Phase-shifting algorithm to achieve high-speed long-depth-range probing by frequency-domain optical coherence tomography." *Optics Letters* 28(22): 2201-2203.

Leitgeb, R. A., L. Schmetterer, et al. (2003). "Real-time assessment of retinal blood flow with ultrafast acquisition by color Doppler Fourier domain optical coherence tomography." *Optics Express* 11(23): 3116-3121.

Leitgeb, R. A., L. Schmetterer, et al. (2004). "Real-time measurement of in vitro flow by Fourier-domain color Doppler optical coherence tomography." *Optics Letters* 29 (2): 171-173.

LeRoyBrehonnet, F. and B. LeJeune (1997). "Utilization of Mueller matrix formalism to obtain optical targets depolarization and polarization properties." *Progress in Quantum Electronics* 21(2): 109-151.

Leske, M. C., A. M. Connell, et al. (1995). "Risk factors for open-angle glaucoma. The Barbados Eye Study. [see comments]." *Archives of Ophthalmology* 113(7): 918-24.

Leske, M. C., A. M. Connell, et al. (2001). "incidence of open-angle glaucoma: the Barbados Eye Studies. The Barbados Eye Studies Group. [see comments]." *Archives of Ophthalmology* 119(1): 89-95.

Leske, M. C., A. Heijl, et al. (1999). "Early Manifest Glaucoma Trial. Design and Baseline Data." *Ophthalmology* 106(11): 2144-2153.

Lewis, S. E., J. R. DeBoer, et al. (2005). "Sensitive, selective, and analytical improvements to a porous silicon gas sensor." *Sensors and Actuators B: Chemical* 110(1): 54-65.

Lexer, F., C. K. Hitzenberger, et al. (1999). "Dynamic coherent focus OCT with depth—independent transversal resolution." *Journal of Modern Optics* 46(3): 541-553.

Li, X., C. Chudoba, et al. (2000). "Imaging needle for optical coherence tomography." *Optics Letters* 25: 1520-1522.

Li, X., T. H. Ko, et al. (2001). "Intraluminal fiber-optic Doppler imaging catheter for structural and functional optical coherence tomography." *Optics Letters* 26: 1906-1908.

Liddington, M. I. and P. G. Shakespeare (1996). "Timing of the thermographic assessment of burns." *Burns* 22(1): 26-8.

Lindmo, T., D. J. Smithies, et al. (1998). "Accuracy and noise in optical Doppler tomography studied by Monte Carlo simulation." *Physics in Medicine and Biology* 43(10): 3045-3064.

Liu, J., X. Chen, et al. (1999). "New thermal wave aspects on burn evaluation of skin subjected to instantaneous heating." *IEEE Transactions on Biomedical Engineering* 46(4): 420-8.

Luke, D. G., R. McBride, et al. (1995). "Polarization mode dispersion minimization in fiber-wound piezoelectric cylinders." *Optics Letters* 20(24): 2550-2552.

MacNeill, B. D., I. K. Jang, et al. (2004). "Focal and multi-focal plaque distributions in patients with macrophage acute and stable presentations of coronary artery disease." *Journal of the American College of Cardiology* 44(5): 972-979.

Mahgerefteh, D. and C. R. Menyuk (1999). "Effect of first-order PMD compensation on the statistics of pulse broadening in a fiber with randomly varying birefringence." *Ieee Photonics Technology Letters* 11(3): 340-342.

Maitland, D. J. and J. T. Walsh, Jr. (1997). "Quantitative measurements of linear birefringence during heating of native collagen." *Lasers in Surgery & Medicine* 20 (3): 310-8.

Majaron, B., S. M. Srinivas, et al. (2000). "Deep coagulation of dermal collagen with repetitive Er : YAG laser irradiation." *Lasers in Surgery and Medicine* 26(2): 215-222.

Mansuripur, M. (1991). "Effects of High-Numerical-Aperture Focusing on the State of Polarization in Optical and Magnetooptic Data-Storage Systems." *Applied Optics* 30(22): 3154-3162.

Marshall, G. W., S. J. Marshall, et al. (1997). "The dentin substrate: structure and properties related to bonding." *Journal of Dentistry* 25(6): 441-458.

Martin, P. (1997). "Wound healing—Aiming for perfect skin regeneration." *Science* 276 (5309): 75-81.

Martinez, O. E. (1987). "3000 Times Grating Compressor with Positive Group-Velocity Dispersion—Application to Fiber Compensation in 1.3-1.6 Mu-M Region." *Ieee Journal of Quantum Electronics* 23(1): 59-64.

Martinez, O. E., J. P. Gordon, et al. (1984). "Negative Group-Velocity Dispersion Using Refraction." *Journal of the Optical Society of America a-Optics Image Science and Vision* 1(10): 1003-1006.

McKinney, J. D., M. A. Webster, et al. (2000). "Characterization and imaging in optically scattering media by use of laser speckle and a variable-coherence source." *Optics Letters* 25(1): 4-6.

Miglior, S., M. Casula, et al. (2001). "Clinical ability of Heidelberg retinal tomograph examination to detect glaucomatous visual field changes." *Ophthalmology* 108 (9): 1621-7.

Milner, T. E., D. M. Goodman, et al. (1996). "Imaging laser heated subsurface chromophores in biological materials: Determination lateral physical dimensions." *Physics in Medicine and of Biology* 41(1): 31-44.

Milner, T. E., D. M. Goodman, et al. (1995). "Depth Profiling of Laser-Heated Chromophores in Biological Tissues by Pulsed Photothermal Radiometry." *Journal of the Optical Society of America a-Optics Image Science and Vision* 12 (7): 1479-1488.

Milner, T. E., D. J. Smithies, et al. (1996). "Depth determination of chromophores in human skin by pulsed photothermal radiometry." *Applied Optics* 35(19): 3379-3385.

Mishchenko, M. I. and J. W. Hovenier (1995). "Depolarization of Light Backscattered by Randomly Oriented Nonspherical Particles." *Optics Letters* 20(12): 1356-&.

Mistlberger, A., J. M. Liebmann, et al. (1999). "Heidelberg retina tomography and optical coherence tomography in normal, ocular-hypertensive, and glaucomatous eyes." *Ophthalmology* 106(10): 2027-32.

Mitsui, T. (1999). "High-speed detection of ballistic photons propagating through suspensions using spectral interferometry." *Japanese Journal of Applied Physics* Part 1-Regular Papers Short Notes & Review Papers 38(5A): 2978-2982.

Molteno, A. C., N. J. Bosma, et al. (1999). "Otago glaucoma surgery outcome study: long-term results of trabeculectomy—1976 to 1995." *Opthalmology* 106(9): 1742-50.

Morgner, U., W. Drexler, et al. (2000). "Spectroscopic optical coherence tomography." *Optics Letters* 25(2): 111-113.

Morgner, U., F. X. Kartner, et al. (1999). "Sub-two-cycle pulses from a Kerr-lens mode-locked Ti : sapphire laser (vol. 24, p. 411, 1999)." *Optics Letters* 24(13): 920-920.

Mourant, J. R., A. H. Hielscher, et al. (1998). "Evidence of intrinsic differences in the light scattering properties of tumorigenic and nontumorigenic cells." *Cancer Cytopathology* 84(6): 366-374.

Muller, M., J. Squier, et al. (1998). "Dispersion pre-compensation of 15 femtosecond optical pulses for high-numerical-aperture objectives." *Journal of Microscopy-Oxford* 191: 141-150.

Muscat, S., N. McKay, et al. (2002). "Repeatability and reproducibility of corneal thickness measurements by optical coherence tomography." *Investigative Ophthalmology & Visual Science* 43(6): 1791-5.

Musch, D. C., P. R. Lichter, et al. (1999). "The Collaborative Initial Glaucoma Treatment Study. Study Design, MethodsR, and Baseline Characteristics of Enrolled Patients." *Ophthalmology* 106: 653-662.

Neerken, S., Lucassen, G.W., Bisschop, M.A., Lenderink, E., Nuijs, T.A.M. (2004). "Characterization of age-related effects in human skin: A comparative study that applies confocal laser scanning microscopy and optical coherence tomography." *Journal of Biomedical Optics* 9(2): 274-281.

Nelson, J. S., K. M. Kelly, et al. (2001). "Imaging blood flow in human port-wine stain in situ and in real time using optical Doppler tomography." *Archives of Dermatology* 137(6): 741-744.

Newson, T. P., F. Farahi, et al. (1988). "Combined Interferometric and Polarimetric Fiber Optic Temperature Sensor with a Short Coherence Length Source." *Optics Communications* 68(3): 161-165.

November, L. J. (1993). "Recovery of the Matrix Operators in the Similarity and Congruency Transformations—Applications in Polarimetry." *Journal of the Optical Society of America a-Optics Image Science and Vision* 10(4): 719-739.

Oh, W. Y., S. H. Yun, et al. (2005). "Wide tuning range wavelength-swept laser with two semiconductor optical amplifiers." *Ieee Photonics Technology Letters* 17(3): 678-680.

Oka, K. and T. Kato (1999). "Spectroscopic polarimetry with a channeled spectrum." *Optics Letters* 24(21): 1475-1477.

Okugawa, T. and K. Rotate (1996). "Real-time optical image processing by synthesis of the coherence function using real-time holography." *Ieee Photonics Technology Letters* 8(2): 257-259.

Oshima, M., R. Torii, et al. (2001). "Finite element simulation of blood flow in the cerebral artery." *Computer Methods in Applied Mechanics and Engineering* 191 (6-7): 661-671.

Pan, Y. T., H. K. Xie, et al. (2001). "Endoscopic optical coherence tomography based on a microelectromechanical mirror." *Optics Letters* 26(24): 1966-1968.

Parisi, V., G. Manni, et al. (2001). "Correlation between optical coherence tomography, pattern electroretinogram, and visual evoked potentials in open-angle glaucoma patients." *Ophthalmology* 108(5): 905-12.

Park, B. H., M. C. Pierce, et al. (2005). "Real-time fiber-based multi-functional spectral-domain optical coherence tomography at 1.3 mu m." *Optics Express* 13(11): 3931-3944.

Park, D. H., J. W. Hwang, et al. (1998). "Use of laser Doppler flowmetry for estimation of the depth of burns." *Plastic and Reconstructive Surgery* 101(6): 1516-1523.

Pendry, J. B., A. J. Holden, et al. (1999). "Magnetism from conductors and enhanced nonlinear phenomena." *Ieee Transactions on Microwave Theory and Techniques* 47(11): 2075-2084.

Penninckx, D. and V. Morenas (1999). "Jones matrix of polarization mode dispersion." *Optics Letters* 24(13): 875-877.

Pierce, M. C., M. Shishkov, et al. (2005). "Effects of sample arm motion in endoscopic polarization-sensitive optical coherence tomography." *Optics Express* 13(15): 5739-5749.

Pircher, M., E. Gotzinger, et al. (2003). "Measurement and imaging of water concentration in human cornea with differential absorption optical coherence tomography." *Optics Express* 11(18): 2190-2197.

Pircher, M., E. Gotzinger, et al. (2003). "Speckle reduction in optical coherence tomography by frequency compounding." *Journal of Biomedical Optics* 8(3): 565-569.

Podoleanu, A. G., G. M. Dobre, et al. (1998). "En-face coherence imaging using galvanometer scanner modulation." *Optics Letters* 23(3): 147-149.

Podoleanu, A. G. and D. A. Jackson (1999). "Noise analysis of a combined optical coherence tomograph and a confocal scanning ophthalmoscope." *Applied Optics* 38(10): 2116-2127.

Podoleanu, A. G., J. A. Rogers, et al. (2000). "Three dimensional OCT images from retina and skin." *Optics Express* 7(9): 292-298.

Podoleanu, A. G., M. Seeger, et al. (1998). "Transversal and longitudinal images from the retina of the living eye using low coherence reflectometry." *Journal of Biological Optics* 3(1): 12-20.

Poole, C. D. (1988). "Statistical Treatment of Polarization Dispersion in Single-Mode Fiber." *Optics Letters* 13(8): 687-689.

Povazay, B., K. Bizheva, et al. (2002). "Submicrometer axial resolution optical coherence tomography." *Optics Letters* 27(20): 1800-1802.

Qi, B., A. P. Himmer, et al. (2004). "Dynamic focus control in high-speed optical coherence tomography based on a microelectromechanical mirror." *Optics Communications* 232(1-6): 123-128.

Radhakrishnan, S., A. M. Rollins, et al. (2001). "Real-time optical coherence tomography of the anterior segment at 1310 nm." *Archives of Ophthalmology* 119(8): 1179-1185.

Rogers, A. J. (1981). "Polarization-Optical Time Domain Reflectometry—a Technique for the Measurement of Field Distributions." *Applied Optics* 20(6): 1060-1074.

Rollins, A. M. and J. A. Izatt (1999). "Optimal interferometer designs for optical coherence tomography." *Optics Letters* 24(21): 1484-1486.

Rollins, A. M., R. Ung-arunyawee, et al. (1999). "Real-time in vivo imaging of human gastrointestinal ultrastructure by use of endoscopic optical coherence tomography with a novel efficient interferometer design." *Optics Letters* 24(19): 1358-1360.

Rollins, A. M., S. Yazdanfar, et al. (2002). "Real-time in vivo colors Doppler optical coherence tomography." *Journal of Biomedical Optics* 7(1): 123-129.

Rollins, A. M., S. Yazdanfar, et al. (2000). "Imaging of human retinal hemodynamics using color Doppler optical coherence tomography." *Investigative Ophthalmology & Visual Science* 41(4): S548-S548.

Sandoz, P. (1997). "Wavelet transform as a processing tool in white-light interferometry." *Optics Letters* 22(14): 1065-1067.

Sankaran, V., M. J. Everett, et al. (1999). "Comparison of polarized-light propagation in biological tissue and phantoms." *Optics Letters* 24(15): 1044-1046.

Sankaran, V., J. T. Walsh, et al. (2000). "Polarized light propagation through tissue phanto, ehms containing densely packed scatterers." *Optics Letters* 25(4): 239-241

Sarunic, M. V., M. A. Choma, et al. (2005). "Instantaneous complex conjugate resolved spectral domain and swept-source OCT using 3×3 fiber couplers." *Optics Express* 13(3): 957-967.

Sathyam, U. S., B. W. Colston, et al. (1999). "Evaluation of optical coherence quantitation of analytes in turbid media by use of two wavelengths." *Applied Optics* 38(10): 2097-2104.

Schmitt, J. M. (1997). "Array detection for speckle reduction in optical coherence microscopy." *Physics in Medicine and Biology* 42(7): 1427-1439.

Schmitt, J. M. (1999). "Optical coherence tomography (OCT): A review." *Ieee Journal of Selected Topics in Quantum Electronics* 5(4): 1205-1215.

Schmitt, J. M. and A. Knuttel (1997). "Model of optical coherence tomography of heterogeneous tissue." *Journal of the Optical Society of America a-Optics Image Science and Vision* 14(6): 1231-1242.

Schmitt, J. M., S. L. Lee, et al. (1997). "An optical coherence microscope with enhanced resolving power in thick tissue." *Optics Communications* 142(4-6): 203-207.

Schmitt, J. M., S. H. Xiang, et al. (1998). "Differential absorption imaging with optical coherence tomography." *Journal of the Optical Society of America a-Optics Image Science and Vision* 15(9): 2288-2296.

Schmitt, J. M., S. H. Xiang, et al. (1999). "Speckle in optical coherence tomography." *Journal of Biomedical Optics* 4(1): 95-105.

Schmitt, J. M., M. J. Yadlowsky, et al. (1995). "Subsurface Imaging of Living Skin with Optical Coherence Microscopy." *Dermatology* 191(2): 93-98.

Shi, H., J. Finlay, et al. (1997). "Multiwavelength 10-GHz picosecond pulse generation from a single-stripe semiconductor diode laser." *Ieee Photonics Technology Letters* 9(11): 1439-1441.

Shi, H., I. Nitta, et al. (1999). "Demonstration of phase correlation in multiwavelength mode-locked semiconductor diode lasers." *Optics Letters* 24(4): 238-240.

Simon, R. (1982). "The Connection between Mueller and Jones Matrices of Polarization Optics." *Optics Communications* 42(5): 293-297.

Smith, P. J. M., E.M.; Taylor, C.M.; Selviah, D.R.; Day, S.E.; Commander, L.G. "Variable-Focus Microlenses as a Potential Technology for Endoscopy."

Smithies, D. J., T. Lindmo, et al. (1998). "Signal attenuation and localization in optical coherence tomography studied by Monte Carlo simulation." *Physics in Medicine and Biology* 43(10): 3025-3044.

Sorin, W. V. and D. F. Gray (1992). "Simultaneous Thickness and Group Index Measurement Using Optical Low-Coherence Reflectometry." *Ieee Photonics Technology Letters* 4(1): 105-107.

Sticker, M., C. K. Hitzenberger, et al. (2001). "Quantitative differential phase measurement and imaging in transparent and turbid media by optical coherence tomography." *Optics Letters* 26(8): 518-520.

Sticker, M., M. Pircher, et al. (2002). "En face imaging of single cell layers by differential phase-contrast optical coherence microscopy." *Optics Letters* 27(13): 1126-1128.

Stoller, P., B. M. Kim, et al. (2002). "Polarization-dependent optical second-harmonic imaging of a rat-tail tendon." *Journal of Biomedical Optics* 7(2): 205-214.

Sun, C. S. (2003). "Multiplexing of fiber-optic acoustic sensors in a Michelson interferometer configuration." *Optics Letters* 28(12): 1001-1003.

Swanson, E. A., J. A. Izatt, et al. (1993). "In-Vivo Retinal Imaging by Optical Coherence Tomography." *Optics Letters* 18(21): 1864-1866.

Takada, K., A. Himeno, et al. (1991). "Phase-Noise and Shot-Noise Limited Operations of Low Coherence Optical-Time Domain Reflectometry." *Applied Physics Letters* 59(20): 2483-2485.

Takenaka, H. (1973). "Unified Formalism for Polarization Optics by Using Group-Theory I (Theory)." *Japanese Journal of Applied Physics* 12(2): 226-231.

Tanno, N., T. Ichimura, et al. (1994). "Optical Multimode Frequency-Domain Reflectometer." *Optics Letters* 19(8): 587-589.

Tan-no, N., T. Ichimura, et al. (1994). "Optical Multimode Frequency-Domain Reflectometer." *Optics Letters* 19(8): 587-589.

Targowski, P., M. Wojtkowski, et al. (2004). "Complex spectral OCT in human eye imaging in vivo." *Optics Communications* 229(1-6): 79-84.

Tearney, G. J., S. A. Boppart, et al. (1996). "Scanning single-mode fiber optic catheter—endoscope for optical coherence tomography (vol. 21, p. 543, 1996)." *Optics Letters* 21(12): 912-912.

Tearney, G. J., B. E. Bouma, et al. (1996). "Rapid acquisition of in vivo biological images by use of optical coherence tomography." *Optics Letters* 21(17): 1408-1410.

Tearney, G. J., B. E. Bouma, et al. (1997). "In vivo endoscopic optical biopsy with optical coherence tomography." *Science* 276(5321): 2037-2039.

Tearney, G. J., M. E. Brezinski, et al. (1996). "Catheter-based optical imaging of a human coronary artery." *Circulation* 94(11): 3013-3013.
Tearney, G. J., M. E. Brezinski, et al. (1997). "In vivo endoscopic optical biopsy with optical coherence tomography." *Science* 276(5321): 2037-9.
Tearney, G. J., M. E. Brezinski, et al. (1997). "Optical biopsy in human gastrointestinal tissue using optical coherence tomography." *American Journal of Gastroenterology* 92(10): 1800-1804.
Tearney, G. J., M. E. Brezinski, et al. (1995). "Determination of the refractive index of highly scattering human tissue by optical coherence tomography." *Optics Letters* 20(21): 2258-2260.
Tearney, G. J., I. K. Jang, et al. (2000). "Porcine coronary imaging in vivo by optical coherence tomography." *Acta Cardiologica* 55(4): 233-237.
Tearney, G. J., R. H. Webb, et al. (1998). "Spectrally encoded confocal microscopy." *Optics Letters* 23(15): 1152-1154.
Tearney, G. J., H. Yabushita, et al. (2003). "Quantification of macrophage content in atherosclerotic plaques by optical coherence tomography." *Circulation* 107(1): 113-119.
Tower, T. T. and R. T. Tranquillo (2001). "Alignment maps of tissues: I. Microscopic elliptical polarimetry." *Biophysical Journal* 81(5): 2954-2963.
Tower, T. T. and R. T. Tranquillo (2001). "Alignment maps of tissues: II. Fast harmonic analysis for imaging." *Biophysical Journal* 81(5): 2964-2971.
Troy, T. L. and S. N. Thennadil (2001). "Optical properties of human skin in the near infrared wavelength range of 1000 to 2200 nm." *Journal of Biomedical Optics* 6 (2): 167-176.
Vabre, L., A. Dubois, et al. (2002). "Thermal-light full-field optical coherence tomography." *Optics Letters* 27(7): 530-532.
Vakhtin, A. B., D. J. Kane, et al. (2003). "Common-path interferometer for frequency-domain optical coherence tomography." *Applied Optics* 42(34): 6953-6958.
Vakhtin, A. B., K. A. Peterson, et al. (2003). "Differential spectral interferometry: an imaging technique for biomedical applications." *Optics Letters* 28(15): 1332-1334.
Vakoc, B. J., S. H. Yun, et al. (2005). "Phase-resolved optical frequency domain imaging." *Optics Express* 13(14): 5483-5493.
van Leeuwen, T. G., M. D. Kulkarni, et al. (1999). "High-flow-velocity and shear-rate imaging by use of color Doppler optical coherence tomography." *Optics Letters* 24(22): 1584-1586.
Vansteenkiste, N., P. Vignolo, et al. (1993). "Optical Reversibility Theorems for Polarization—Application to Remote-Control of Polarization." *Journal of the Optical Society of America a-Optics Image Science and Vision* 10(10): 2240-2245.
Vargas, O., E. K. Chan, et al. (1999). "Use of an agent to reduce scattering in skin." *Lasers in Surgery and Medicine* 24(2): 133-141.
Wang, R. K. (1999). "Resolution improved optical coherence-gated tomography for imaging through biological tissues." *Journal of Modern Optics* 46(13): 1905-1912.
Wang, X. J., T. E. Milner, et al. (1997). "Measurement of fluid-flow-velocity profile in turbid media by the use of optical Doppler tomography." *Applied Optics* 36(1): 144-149.
Wang, X. J., T. E. Milner, et al. (1995). "Characterization of Fluid-Flow Velocity by Optical Doppler Tomography." *Optics Letters* 20(11): 1337-1339.
Wang, Y. M., J. S. Nelson, et al. (2003). "Optimal wavelength for ultrahigh-resolution optical coherence tomography." *Optics Express* 11(12): 1411-1417.
Wang, Y. M., Y. H. Zhao, et al. (2003). "Ultrahigh-resolution optical coherence tomography by broadband continuum generation from a photonic crystal fiber." *Optics Letters* 28(3): 182-184.
Watkins, L. R., S. M. Tan, et al. (1999). "Determination of interferometer phase distributions by use of wavelets." *Optics Letters* 24(13): 905-907.
Wetzel, J. (2001). "Optical coherence tomography in dermatology: a review." *Skin Research and Technology* 7(1): 1-9.
Wentworth, R. H. (1989). "Theoretical Noise Performance of Coherence-Multiplexed Interferometric Sensors." *Journal of Lightwave Technology* 7(6): 941-956.
Westphal, V., A. M. Rollins, et al. (2002). "Correction of geometric and refractive image distortions in optical coherence tomography applying Fermat's principle." *Optics Express* 10(9): 397-404.
Westphal, V., S. Yazdanfar, et al. (2002). "Real-time, high velocity-resolution color Doppler optical coherence tomography." *Optics Letters* 27(1): 34-36.
Williams, P. A. (1999). "Rotating-wave-plate Stokes polarimeter for differential group delay measurements of polarization-mode dispersion." *Applied Optics* 38(31): 6508-6515.
Wojtkowski, M., T. Bajraszewski, et al. (2003). "Real-time in vivo imaging by high-speed spectral optical coherence tomography." *Optics Letters* 28(19): 1745-1747.
Wojtkowski, M., A. Kowalczyk, et al. (2002). "Full range complex spectral optical coherence tomography technique in eye imaging." *Optics Letters* 27(16): 1415-1417.
Wojtkowski, M., R. Leitgeb, et al. (2002). "In vivo human retinal imaging by Fourier domain optical coherence tomography." *Journal of Biomedical Optics* 7(3): 457-463.
Wojtkowski, M., R. Leitgeb, et al. (2002). "Fourier domain OCT imaging of the human eye in vivo." *Proc. SPIE* 4619: 230-236.
Wojtkowski, M., V. J. Srinivasan, et al. (2004). "Ultrahigh-resolution, high-speed, Fourier domain optical coherence tomography and methods for dispersion compensation." *Optics Express* 12(11): 2404-2422.
Wong, B. J. F., Y. H. Zhao, et al. (2004). "Imaging the internal structure of the rat cochlea using optical coherence tomography at 0.827 mu m and 1.3 mu m." *Otolaryngology-Head and Neck Surgery* 130(3): 334-338.
Yabushita, H. B., B.E.; Houser, S.L.; Aretz, H.T.; Jang, I.; Schlendorf, K.H.; Kauffman, C.R.; Shishkov, M.; Halpern, E.F.; Tearney, G.J. "Measurement of Thin Fibrous Caps in Atherosclerotic Plaques by Optical Coherence Tomography."
Yang, C., A. Wax, et al. (2001). "Phase-dispersion optical tomography." *Optics Letters* 26(10): 686-688.
Yang, C., A. Wax, et al. (2001). "Phase-referenced interferometer with subwavelength and subhertz sensitivity applied to the study of cell membrane dynamics." *Optics Letters* 26(16): 1271-1273.
Yang, C. H., A. Wax, et al. (2001). "Phase-dispersion optical tomography." *Optics Letters* 26(10): 686-688.
Yang, C. H., A. Wax, et al. (2000). "Interferometric phase-dispersion microscopy." *Optics Letters* 25(20): 1526-1528.
Yang, V. X. D., M. L. Gordon, et al. (2002). "Improved phase-resolved optical Doppler tomography using the Kasai velocity estimator and histogram segmentation." *Optics Communications* 208(4-6): 209-214.
Yang, V. X. D., M. L. Gordon, et al. (2003). "High speed, wide velocity dynamic range Doppler optical coherence tomography (Part I): System design, signal processing, and performance." *Optical Express* 11(7): 794-809.
Yang, V. X. D., M. L. Gordon, et al. (2003). "High speed, wide velocity dynamic range Doppler optical coherence tomography (Part II): Imaging in vivo cardiac dynamics of *Xenopus laevis*." *Optics Express* 11(14): 1650-1658.
Yang, V. X. D., M. L. Gordon, et al. (2003). "High speed, wide velocity dynamic range Doppler optical coherence tomography (Part III): in vivo endoscopic imaging of blood flow in the rat and human gastrointestinal tracts." *Optics Express* 11(19): 2416-2424.
Yang, V. X. D., B. Qi, et al. (2003). "In vivo feasibility of endoscopic catheter-based Doppler optical coherence tomography." *Gastroenterology* 124(4): A49-A50.
Yao, G. and L. H. V. Wang (2000). "Theoretical and experimental studies of ultrasound-modulated optical tomography in biological tissue." *Applied Optics* 39(4): 659-664.
Yazdanfar, S. and J. A. Izatt (2002). "Self-referenced Doppler optical coherence tomography." *Optics Letters* 27(23): 2085-2087.
Yazdanfar, S., M. D. Kulkarni, et al. (1997). "High resolution imaging of in vivo cardiac dynamics using color Doppler optical coherence tomography." *Optics Express* 1 (13): 424-431.
Yazdanfar, S., A. M. Rollins, et al. (2000). "Imaging and velocimetry of the human retinal circulation with color Doppler optical coherence tomography." *Optics Letters* 25(19): 1448-1450.

Yazdanfar, S., A. M. Rollins, et al. (2000). "Noninvasive imaging and velocimetry of human retinal blood flow using color Doppler optical coherence tomography." *Investigative Ophthalmology & Visual Science* 41(4): S548-S548.

Yazdanfar, S., A. M. Rollins, et al. (2003). "In vivo imaging of human retinal flow dynamics by color Doppler optical coherence tomography." *Archives of Ophthalmology* 121(2): 235-239.

Yazdanfar, S., C. H. Yang, et al. (2005). "Frequency estimation precision in Doppler optical coherence tomography using the Cramer-Rao lower bound." *Optics Express* 13(2): 410-416.

Yun, S. H., C. Boudoux, et al. (2004). "Extended-cavity semiconductor wavelength—swept laser for biomedical imaging." *Ieee Photonics Technology Letters* 16(1): 293-295.

Yun, S. H., C. Boudoux, et al. (2003). "High-speed wavelength-swept semiconductor laser with a polygon-scanner-based wavelength filter." *Optics Letters* 28(20): 1981-1983.

Yun, S. H., G. J. Tearney, et al. (2004). "Pulsed-source and swept-source spectral—domain optical coherence tomography with reduced motion artifacts." *Optics Express* 12(23): 5614-5624.

Yun, S. H., G. J. Tearney, et al. (2004). "Removing the depth-degeneracy in optical frequency domain imaging with frequency shifting." *Optics Express* 12(20): 4822-4828.

Yun, S. H., G. J. Tearney, et al. (2004). "Motion artifacts in optical coherence tomography with frequency-domain ranging." *Optics Express* 12(13): 2977-2998.

Liptak David C. et al., (2007) "On the Development of a Confocal Rayleigh-Brillouin Microscope" *American Institute of Physics* vol. 78, 016106.

Office Action mailed Oct. 1, 2008 for U.S. Appl. No. 11/955,986.

Invitation of Pay Additional Fees mailed Aug. 7, 2008 for International Application No. PCT/US2008/062354.

Invitation of Pay Additional Fees mailed Jul. 20, 2008 for International Application No. PCT/US2007/081982.

International Search Report and Written Opinion mailed Mar. 7, 2006 for PCT/US2005/035711.

International Search Report and Written Opinion mailed Jul. 18, 2008 for PCT/US2008/057533.

Aizu, Y et al. (1991) "Bio-Speckle Phenomena and Their Application to the Evaluation of Blood Flow" Optics and Laser Technology, vol. 23, No. 4, Aug. 1, 1991.

Richards G.J. et al. (1997) "Laser Speckle Contrast Analysis (LASCA): A Technique for Measuring Capillary Blood Flow Using the First Order Statistics of Laser Speckle Patterns" Apr. 2, 1997.

Gonick, Maria M., et al (2002) "Visualization of Blood Microcirculation Parameters in Human Tissues by Time Integrated Dynamic Speckles Analysis" vol. 972, No. 1, Oct. 1, 2002.

International Search Report and Written Opinion mailed Jul. 4, 2008 for PCT/US2008/051432.

Jonathan, Enock (2005) "Dual Reference Arm Low-Coherence Interferometer-Based Reflectometer for Optical Coherence Tomography (OCT) Application" *Optics Communications* vol. 252.

Motaghian Nezam, S.M.R. (2007) "increased Ranging Depth in optical Frequency Domain Imaging by Frequency Encoding" *Optics Letters*, vol. 32, No. 19, Oct. 1, 2007.

Office Action dated Jun. 30, 2008 for U.S. Appl. No. 11/670,058.

Office Action dated Jul. 7, 2008 for U.S. Appl. No. 10/551,735.

Australian Examiner's Report mailed May 27, 2008 for Australian patent application No. 2003210669.

Notice of Allowance mailed Jun. 4, 2008 for U.S. Appl. No. 11/174,425.

European communication dated May 15, 2008 for European patent application No. 05819917.5.

International Search Report and Written Opinion mailed Jun. 10, 2008 for PCT/US2008/051335.

Oh. W.Y. et al (2006) "Ultrahigh-Speed Optical Frequency Domain Imaging and Application to laser Ablation Monitoring" *Applied Physics Letters*, vol. 88.

Office Action dated Aug. 21, 2008 for U.S. Appl. No. 11/505,700.

Sticker, Markus (2002) En Face Imaging of Single Cell layers by Differential Phase-Contrast Optical Coherence Microscopy) *Optics Letters*, col. 27, No. 13, Jul. 1, 2002.

International Search Report and Written Opinion dated Jul. 17, 2008 for International Application No. PCT/US2008/057450.

International Search Report and Written Opinion dated Aug. 11, 2008 for International Application No. PCT/US2008/058703.

US National Library of Medicine (NLM), Bethesda, MD, US; Oct. 2007, "Abstracts of the 19th Annual Symposium of Transcatheter Cardiovascular Therapeutics, Oct. 20-25, 2007, Washington, DC, USA."

International Search Report and Written Opinion dated May 26, 2008 for International Application No. PCT/US2008/051404.

Office Action dated Aug. 25, 2008 for U.S. Appl. No. 11/264,655.

Office Action dated Sep. 11, 2008 for U.S. Appl. No. 11/624,334.

Office Action dated Aug. 21, 2008 for U.S. Appl. No. 11/956,079.

Gelikono, V. M. et al. (Oct. 1, "Two-Wavelength Optical Coherence Tomography" Radio physics and Quantum Electronics, Kluwer Academic Publishers-Consultants. vol. 47, No. 10-1.

International Search Report and Written Opinion for PCT/US2007/081982 dated Oct. 19, 2007.

Database Compendex Engineering Information, Inc., New York, NY, US; Mar. 5, 2007, Yelin, Dvir et al: "Spectral-Domain Spectrally-Encoded Endoscopy".

Database Biosis Biosciences Information Service, Philadelphia, PA, US; Oct. 2006, Yelin D. et al: "Three-Dimensional Miniature Endoscopy".

International Search Report and Written Opinion mailed Mar. 14, 2005 for PCT/US2004/018045.

Notification of the international Preliminary Report on Patentability mailed Oct. 21, 2005.

Shim M.G. et al., "Study of Fiber-Optic Probes For In vivo Medical Raman Spectroscopy" Applied Spectroscopy. vol. 53, No. 6, Jun. 1999.

Bingid U. et al., "Fibre-Optic Laser-Assisted Infrared Tumour Diagnostics (FLAIR); Infrared Tomour Diagnostics" Journal of Physics D. Applied Physics, vol. 38, No. 15, Aug. 7, 2005.

Jun Zhang et al. "Full Range Polarization-Sensitive Fourier Domain Optical Coherence Tomography" Optics Express, vol. 12, No. 24. Nov. 29, 2004.

Yonghua et al., "Real-Time Phase-Resolved Functional Optical Hilbert Transformation" Optics Letters, vol. 27, No. 2, Jan. 15, 2002.

Siavash et al., "Self-Referenced Doppler Optical Coherence Tomography" Optics Letters, vol. 27, No. 23, Dec. 1, 2002.

International Search Report and Written Opinion dated Dec. 20, 2004 for PCT/US04/10152.

Notification Concerning Transmittal of International Preliminary Report on Patentability dated Oct. 13, 2005 for PCT/US04/10152.

International Search Report and Written Opinion dated Mar. 23, 2006 for PCT/US2005/042408.

International Preliminary Report on Patentability dated Jun. 7, 2007 for PCT/US2005/042408.

International Search Report and Written Opinion dated Feb. 28, 2007 for International Application No. PCT/US2006/038277.

International Search Report and Written Opinion dated Jan. 30, 2009 for International Application No. PCT/US2008/081834.

* cited by examiner

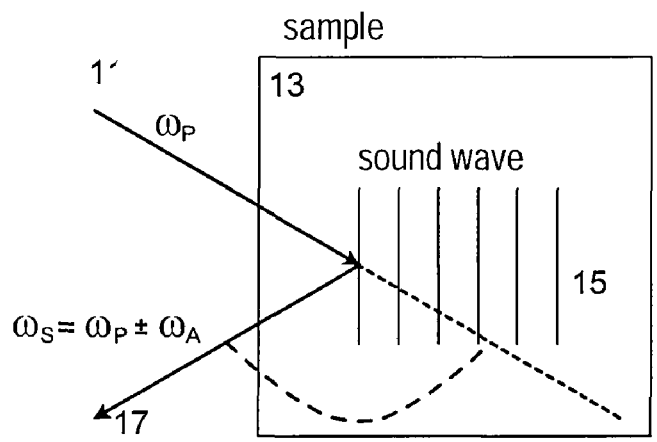
F I G. 1
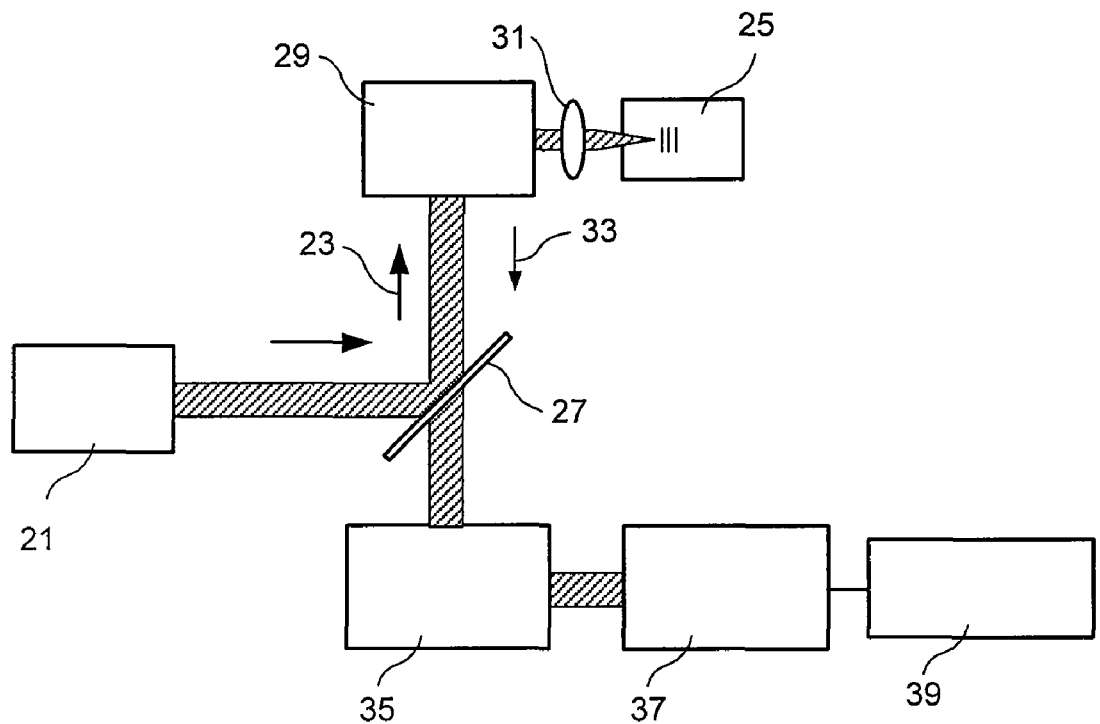
F I G. 2

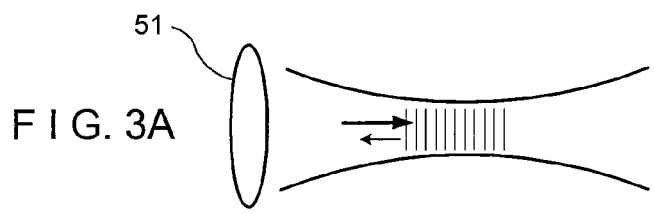
F I G. 3A
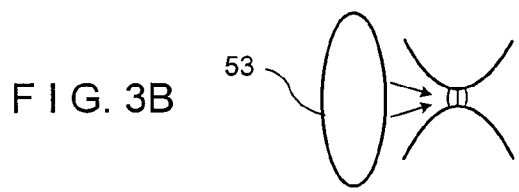
F I G. 3B
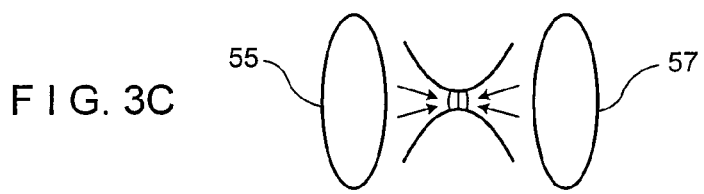
F I G. 3C
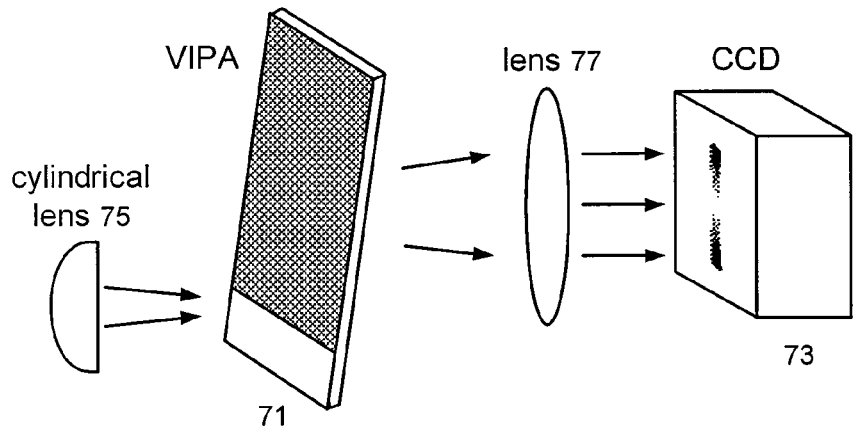
F I G. 4

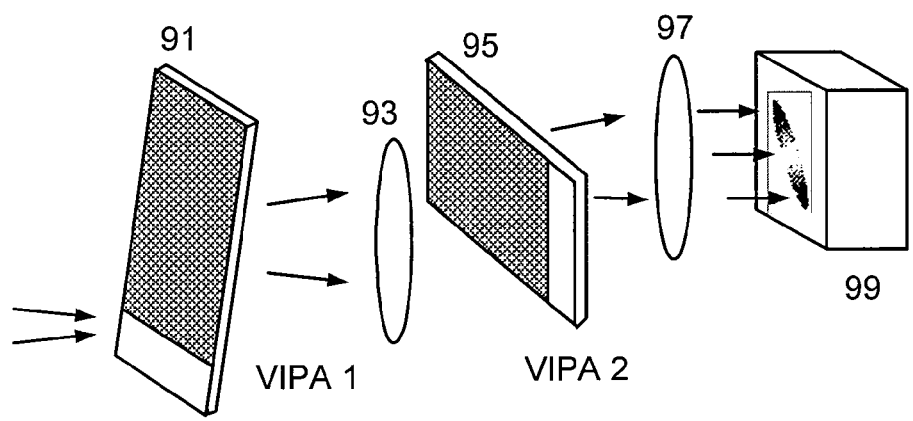
F I G. 5
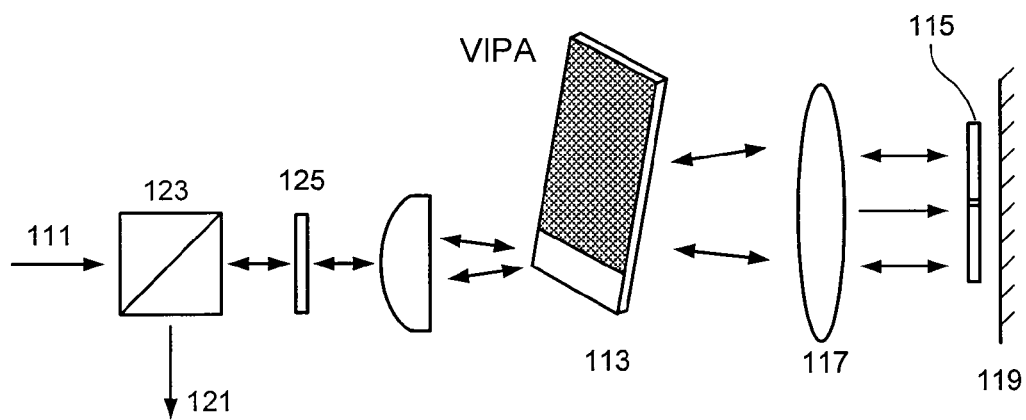
F I G. 6

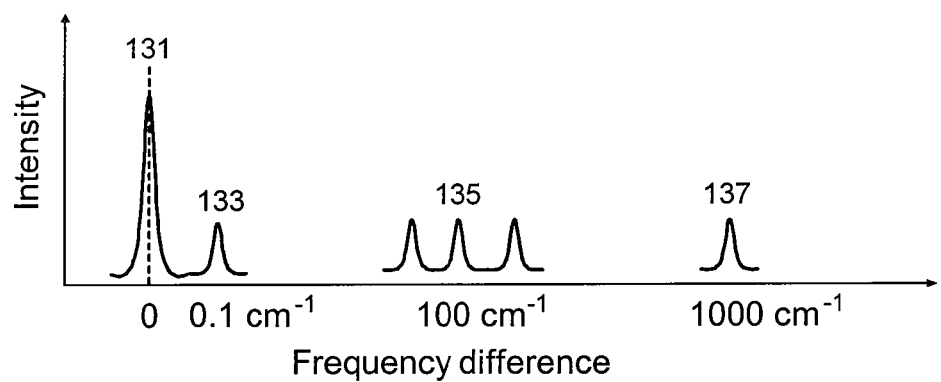
F I G. 7
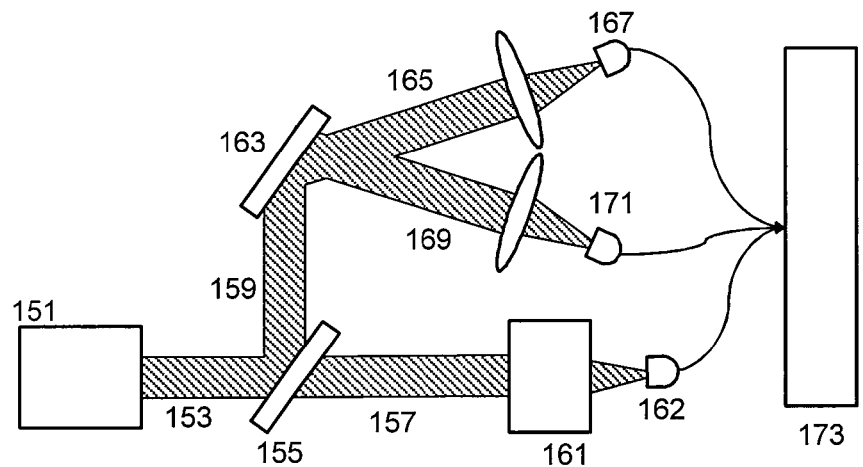
F I G. 8

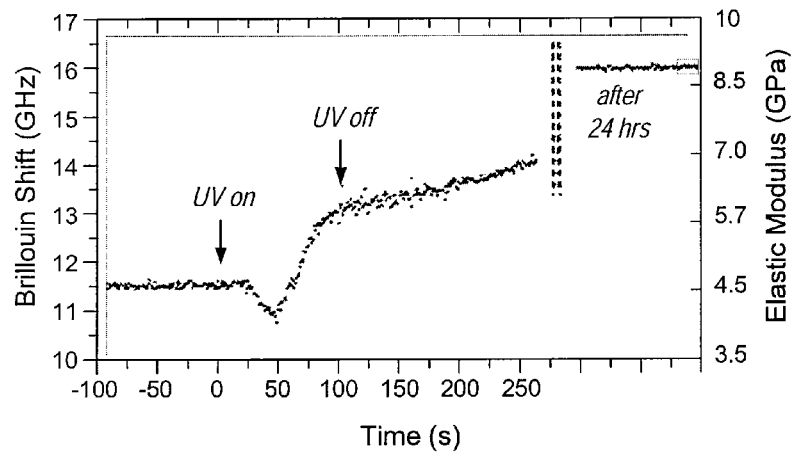
F I G. 13
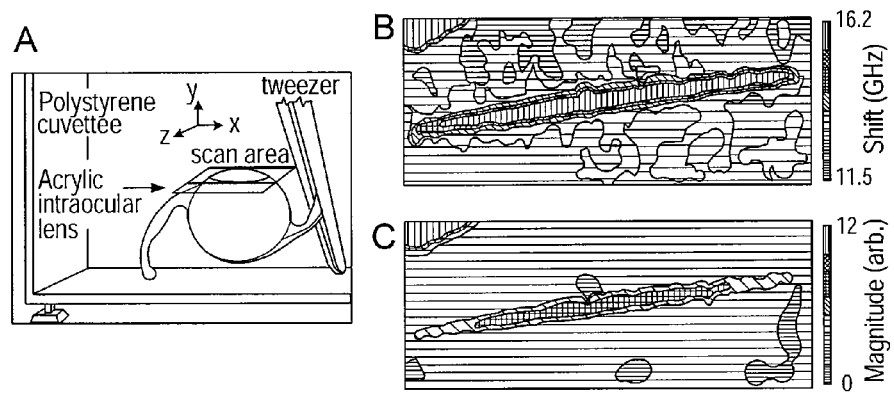
F I G. 14

METHODS, ARRANGEMENTS AND SYSTEMS FOR OBTAINING INFORMATION ASSOCIATED WITH A SAMPLE USING OPTICAL MICROSCOPY

STATEMENT REGARDING FEDERALLY SPONSORED RESEARCH

The invention was made with the U.S. Government support under Grant Number DAD17-02-2-0002 awarded by the U.S. Department of the Army. Thus, the U.S. Government has certain rights in the invention.

CROSS-REFERENCE TO RELATED APPLICATION(S)

This application is based upon and claims the benefit of priority from U.S. Patent Application Ser. No. 60/915,990, filed May 4, 2007, the entire disclosure of which is incorporated herein by reference.

FIELD OF THE INVENTION

The present invention relates to methods, arrangements and systems which can obtain acoustic information associated with a sample using electromagnetic radiation, and more particularly to such methods, systems and arrangements that can obtain viscoelastic properties of the sample by performing highly efficient Brillouin optical spectroscopy and imaging. This invention further relates to methods, arrangements and systems that combine Brillouin spectroscopy or imaging with reflectance, fluorescence, or Raman spectroscopy or imaging for simultaneous multimodal characterization of a sample.

BACKGROUND INFORMATION

When an electromagnetic radiation or an optical wave is propagated in a medium, it can be scattered inelastically by acoustic phonons inside the material. This process is known as Brillouin scattering. Brillouin scattering involves acoustic phonons, which may be different from Raman scattering that involves vibrational or rotational phonons.

Spontaneous Brillouin scattering involves acoustic phonons that may be present in a material by thermally-induced density fluctuations. Brillouin scattering can be further enhanced, stimulated, or forced by one or multiple optical pump waves with strong intensity. The magnitude and frequency of Brillouin-scattered light, or its optical spectrum, can be determined by characteristics of the acoustic phonons inside the material. The latter may be closely related to mechanical properties of the medium, such as modulus and hypersonic damping coefficient. Such viscoelastic properties therefore may be measurable by examining the Brillouin scattered light. This technique is referred to as Brillouin spectroscopy. Various techniques to detect the Brillouin signal have been widely applied in physics, material science, and mechanical engineering.

Prior Brillouin scattering studies have been also performed on biological samples, such as collagen fibers, cornea, and crystalline lens, ex vivo, as described in J. M. Vaughan and J. T. Randall, "Brillouin-Scattering, Density and Elastic Properties of the Lens and Cornea of the Eye," *Nature*, vol. 284, pp. 489-491, 1980, R. Harley, D. James, A. Miller, and J. W. White, "Phonons and Elastic-Moduli of Collagen and Muscle," *Nature*, vol. 267, pp. 285-287, 1977, and J. Randall and J. M. Vaughan, "Brillouin-Scattering in Systems of Biological Significance," *Philosophical Transactions of the Royal Society of London Series a-Mathematical Physical and Engineering Sciences*, vol. 293, pp. 341-348, 1979. However, the potential of using Brillouin scattering for tissue biomechanics and tissue engineering has not been significantly explored, possibly because of long acquisition times required by the spectral analysis.

Accordingly, there is a need to overcome the deficiencies described herein above, and to provide improved apparatus, systems and processes for analyzing tissue biomechanics using Brillouin techniques.

OBJECTS AND SUMMARY OF EXEMPLARY EMBODIMENTS

To address and/or overcome the above-described problems and/or deficiencies, exemplary embodiments of imaging systems, arrangements and processes can be provided that are capable of combining a rapid spectroscopic analysis of Brillouin scattering with high spatial-resolution microscopy to probe a sample such as human tissue or artificially engineered tissue or other natural and synthetic biomaterial and retrieve their biomechanical properties such as complex modulus at the tissue.

In one exemplary apparatus, a novel rapid yet high-resolution spectroscopic analysis can enable the image formation. A pump beam can be scanned over a sample through an objective lens, and Brillouin-shifted optical waves are detected to characterize their Brillouin spectra. The measured spectral features of the Brillouin signal can be used as contrast for imaging; an image can be obtained by use of a proper lookup table or an appropriate processing computational routine. Thin cross-sectional images of a biological sample can be obtained by using a high numerical-aperture objective lens and confocal detection.

In another exemplary apparatus in accordance with the present invention, the rapid spectral analysis can be multiplexed for different regimes. This can include empowering an optical microscope with different spectral modalities. Elastic scattering, Raman scattering, and/or fluorescence as well as Brillouin scattering from a sample can be simultaneously measured and three-dimensionally mapped to obtain a structural, chemical, functional as well as mechanical information of the sample.

Exemplary embodiments of the present invention provide apparatus and methods which can allow information about biomechanical properties of a material, particularly a biomaterial, to be obtained non-invasively. Such exemplary embodiments can find a wide range of applications in biology and medicine as well as tissue engineering. Potential applications of Brillouin microscopy include in situ, or in vivo, real-time characterization of collagen cross-linking, intraoperative characterizations of tissues based on biomechanical properties, in vivo disease diagnosis, intraoperative tumor margin determination, wound healing monitoring and/or tissue ablation monitoring.

For example, using the exemplary embodiments of the present invention, it is possible to obtain the viscoelastic properties of a sample such as biomaterial, by performing highly efficient Brillouin optical spectroscopy or imaging. Further exemplary embodiments of the present invention can further relate to methods, arrangements and systems that combine Brillouin spectroscopy and imaging with reflectance, fluorescence, or Raman spectroscopy and imaging for simultaneous multimodal characterization of a sample.

Thus, in accordance with certain exemplary embodiments of the present invention, arrangements and methods are provided for obtaining information about a sample. For example, in one exemplary embodiment, it is possible (e.g., using a first arrangement) to receive a first electro-magnetic radiation from a sample which is based on a second electro-magnetic radiation forwarded to the sample. The first electro-magnetic radiation can have a first frequency and the second electro-magnetic radiation has a second frequency which is different from the first frequency. The difference between the first and second frequencies can be based on an acoustic wave inside the sample related to at least one characteristic of the sample. For example, such difference can be is between about −100 GHz and +100 GHz and may be based on an acoustic wave inside the sample related to at least one characteristic of the sample. The first arrangement may employ a confocal pinhole or single-mode optical fiber.

Further exemplary embodiments of the present invention can facilitate (e.g., using a second arrangement) a receipt of at least a portion of the first electromagnetic radiation and separate such second electromagnetic radiation into a particular finite number (N) of frequency component radiations. For example, N can correspond to the number of spectrally resolvable elements and, typically, can range from about 10 to 100 for a Fabry-Perot interferometer or a diffractive grating. A plurality of such frequency component radiations can be simultaneously measured by an array of detectors, where the total combined energy of the frequency component radiations may be greater than 1/N times the energy of the received portion of the first electromagnetic radiation.

In addition, according to the exemplary embodiment of the present invention, it is possible (e.g., using a third arrangement) to receive a particular energy of more than 1/N of energy of the third electro-magnetic radiation, and generate information associated with the sample.

According to another exemplary embodiment of the present invention, it is possible (e.g., using a fourth arrangement) to generate information associated with the sample and to create images of the sample based on the information. In addition, it is possible (e.g., using a fifth arrangement) to scan the second electromagnetic radiation or to move the sample to probe different locations in the sample.

According to another exemplary embodiment of the present invention, the information may be related to a difference between the first and second frequencies, an optical energy associated with a particular finite group of frequency component radiations, and/or a linewidth of a plurality of the frequency component radiations, each of which may be associated with a particular frequency. This linewidth can be equivalent to a linewidth of Brillouin scattering, which may be related to an acoustic damping coefficient of the sample. In contrast, a linewidth of each frequency component radiation can be equivalent to an intrinsic spectral resolution of the second arrangement such as, e.g., a spectrometer. The retrieved information can relate to bio-mechanical properties of the sample that include but are not limited to a complex modulus of the sample, a cross linking of collagen or another anatomical structure.

In a still further exemplary embodiment of the present invention, the first arrangement can include a narrow-band spectral filter arrangement which can receive the first electromagnetic radiation and attenuate at least a portion thereof which has a frequency which is approximately the same as the second frequency.

Still further exemplary embodiments of the present invention can provide (e.g., using another first arrangement) for a receipt of a first electro-magnetic radiation and a second electro-magnetic radiation provided from a sample, where the first and second electro-magnetic radiations may be based on a third electro-magnetic radiation forwarded to the sample. The first electro-magnetic radiation can have a first frequency, and the second electro-magnetic radiation can have a second frequency and the third electro-magnetic radiation can have a third frequency which may be different from the first frequency. A difference between the first and third frequencies can be based on an acoustic wave inside the sample which may be related to at least one characteristic of the sample. The second electromagnetic radiation can be based on at least one of an elastic scattering, a Raman scattering or a fluorescence within the sample.

In another exemplary embodiment of the present invention, it is possible (e.g., using such other first arrangement) to separate the first and second electro-magnetic radiations into first and second frequency component radiations, respectively. A narrow band spectral separating arrangement can be provided to separate the first electro-magnetic radiation, and a broadband spectral separating arrangement configured to separate the second electro-magnetic radiation. For example, it is possible (e.g., using another second arrangement) to simultaneously detect the first and second frequency component radiations, and to generate information associated with the sample based on the first and second frequency component radiations.

In another exemplary embodiment of the present invention, it is possible (e.g., using another third arrangement) to image the portion of the sample based on the information.

These and other objects, features and advantages of the present invention will become apparent upon reading the following detailed description of embodiments of the invention, when taken in conjunction with the appended claims.

BRIEF DESCRIPTION OF THE DRAWINGS

Further objects, features and advantages of the present invention will become apparent from the following detailed description taken in conjunction with the accompanying figures showing illustrative embodiments of the present invention, in which:

FIG. 1 is a schematic illustration of an exemplary Brillouin effect;

FIG. 2 is a block diagram of an exemplary apparatus which includes a scanning-beam Brillouin spectroscopy arrangement in accordance with certain exemplary embodiments of the present invention;

FIG. 3A is a first schematic illustration of an exemplary embodiment of a exemplary beam focusing procedure;

FIG. 3B is a second schematic illustration of an exemplary embodiment of a beam focusing procedure;

FIG. 3C is a third schematic illustration of an exemplary embodiment of a beam focusing procedure;

FIG. 4 is a schematic illustration of a parallel detection spectrometer arrangement in accordance with exemplary embodiments of the present invention;

FIG. 5 is a schematic illustration of a tandem parallel detection spectrometer arrangement in accordance with exemplary embodiments of the present invention;

FIG. 6 is a schematic illustration of a narrowband spectral filter arrangement in accordance with exemplary embodiments of the present invention;

FIG. 7 is an exemplary graph of intensities of collected light in accordance with exemplary embodiments of the present invention;

FIG. 8 is a schematic illustration of an exemplary scanning-beam multi-modal spectroscopy-microscopy apparatus in accordance with exemplary embodiments of the present invention;

FIG. 13 is an exemplary graph showing a dynamic monitoring of a Brillouin shift in accordance with exemplary embodiments of the present invention;

FIG. 14A is an illustration of a biomaterial sample which was imaged in accordance with exemplary embodiments of the present invention;

FIG. 14B is a first image obtained from the biomaterial sample shown in FIG. 14A in accordance with exemplary embodiments of the present invention;

FIG. 14C is a second image obtained from the biomaterial sample shown in FIG. 14A in accordance with exemplary embodiments of the present invention;

Figure 9:
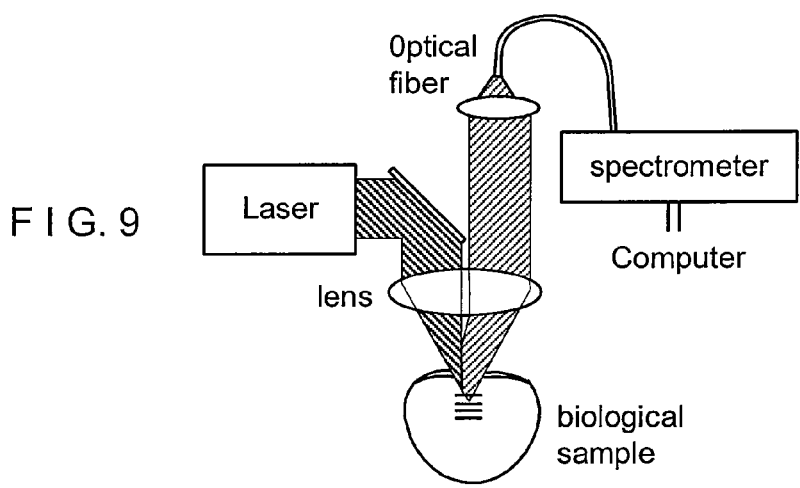
FIG. 9 is a schematic illustration of a prototype system in accordance with exemplary embodiments of the present invention.

Throughout the figures, the same reference numerals and characters, unless otherwise stated, are used to denote like features, elements, components or portions of the illustrated embodiments. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF EXEMPLARY EMBODIMENTS

FIG. 1 illustrates the principle of Brillouin scattering which may be used in exemplary embodiments of the present invention. For example, monochromatic pump light 11 with a frequency $v_P=\omega_P 2\pi$ or wavelength $\lambda_P=c/v_P$ can be provided incident on a medium 13 to be tested. In a spontaneous version of the process, the acoustic waves, due to thermally-induced density fluctuations inside the medium, can generate a periodic refractive index variation 15. Thus, the analyzed sample can be considered as being optically equivalent to a grating which is traveling at the velocity of sound. The scattered light 17 has a different direction because of Bragg-diffraction, and may be Doppler-shifted in frequency by an acoustic wavelength. It can have a spectral linewidth which may be determined by the inverse of the lifetime of the measured acoustic phonon. Both Stokes and anti-Stokes components, of lower and higher frequencies respectively, can be equally generated in the spontaneous process.

The phase matching conditions between the pump and scattering light and the acoustic wave can be expressed as:

$$\omega_A = \omega_p - \omega_s; \tag{1}$$

$$\vec{k}_A = \vec{k}_p - \vec{k}_s, \tag{2}$$

where $\omega$ and $k$ are angular frequency and wave number, respectively, and the subscript A, p, and s represent the acoustic phonons, pump and scattering (or signal) photons, respectively.

The frequency of the phase matched phonons, e.g., a difference between the pump and scattering photons, can be expressed as:

$$v_A = \pm \frac{2nV}{\lambda_P} \sin\left(\frac{\theta}{2}\right), \tag{3}$$

where n is a refractive index of the sampled material, V is a sound velocity inside the medium, and $\theta$ is an angle between incident and scattered optical radiation. When the two waves propagate at the opposite direction, e.g., $\theta=180$ deg, the magnitude of Brillouin shift can attain a maximum value.

The linewidth of Brillouin radiation can be expressed as:

$$\Delta v_A = \frac{\alpha V}{\pi}, \tag{4}$$

where $\alpha$ represents an attenuation coefficient of the sound wave inside the sample.

The magnitude of the scattered radiation can provide additional information related to the coupling of acoustic and optical energy inside the sample and can be determined by the scattering cross section $R_B$, as described in H. Z. Cummins and R. W. Gammon, "Rayleigh and Brillouin Scattering in Liquids—Landau-Placzek Ratio," *Journal of Chemical Physics*, vol. 44, pp. 2785-&, 1966:

$$R_B \equiv \frac{1}{V_{INT}} \frac{d\sigma}{d\Omega} \approx \frac{\pi^2 kT}{2\lambda_p^4} \frac{1}{\rho V^2} \left(\rho \frac{\partial \varepsilon}{\partial \rho}\right)^2, \quad (5)$$

where $V_{INT}$ is the interaction volume inside the sample, k is the Boltzmann constant, T is the temperature, $\rho$ is the density of the material, and $$\left(\rho \frac{\partial \varepsilon}{\partial \rho}\right)^2$$

can represent an electrostriction coefficient of the material.

Once the acoustic wave is initially developed, the Brillouin phenomenon may be accelerated because of the presence of the scattered light. The scattered light, coherent with the pump light, can amplify the resonant acoustic wave which in turn enhances the Brillouin scattering. This positive feedback can result in strong Brillouin shifted scattered light, a process which may be referred to as stimulated Brillouin scattering. Typically, a Stokes Brillouin component (e.g., having a frequency down shifted) may be predominantly generated in the stimulated scattering process. The process can also be enhanced or forced when two monochromatic pump waves with frequencies separated by $v_A$ are incident on a sample, as described in T. Sonehara and H. Tanaka, "Forced Brillouin Spectroscopy Using Frequency-Tunable Continuous-Wave Lasers," *Physical Review Letters*, vol. 75, pp. 4234-4237, 1995. When the frequency difference is matched to one of the acoustic phonon frequencies in the sample, multiple Brillouin lines can be generated.

Brillouin interaction is typically a bulk phenomenon measuring bulk acoustic modes. However, as the sizes of the analyzed samples shrink or the opacity of materials increases, boundary effects can become significant in Brillouin scattering. Confined acoustic modes can be preferentially enhanced depending on the geometrical properties of analyzed environments such as size and shape of boundaries or of their individual constituents. An example of this effect is Brillouin scattering from thin films where optical radiation can be dominantly scattered by a surface acoustic wave that determines a dynamical deformation of the sample border known as surface-ripple, as described in R. Loudon, "Theory of Surface-Ripple Brillouin-Scattering by Solids," *Physical Review Letters*, vol. 40, pp. 581-583, 1978. Recently, confined acoustic modes have also been observed in nanoparticles, as described in H. S. Lim, M. H. Kuok, S. C. Ng, and Z. K. Wang, "Brillouin observation of bulk and confined acoustic waves in silica microspheres," *Applied Physics Letters*, vol. 84, pp. 4182-4184, 2004. For example, empirically, the limit on the dimensions at which bulk Brillouin interactions may be observable has been evinced to be a few acoustic wavelengths, e.g., $\approx \lambda_P/2n$.

Brillouin spectroscopy is a technique that can measure a spectrum of Brillouin scattered light with respect to the pump waves, thereby probing the characteristics of acoustic phonons in a medium. Under certain conditions, it can serve as a mechanical fingerprint of the medium. For example, mechanically, Brillouin scattering can monitor the stress response of a sample to a one-dimensional sinusoidal strain of high frequency (GHz). For viscoelastic materials, the stress of the sample can be determined by a complex longitudinal modulus (M=M'+iM") whose real part expresses the elastic response and whose imaginary part expresses the viscous response, e.g., the loss of acoustic energy in the sample. The acoustic parameters directly measured (V and $\alpha$) can be related to the longitudinal modulus through the density $\rho$ of the material [3], e.g.:

$$M'=\rho V^2; M''=2\rho V^3 \alpha/v_B. \quad (6)$$

In exemplary embodiments of the present invention, a two-dimensional or three-dimensional microscopic mapping of the mechanical properties of a material, in particular a biological sample, can be constructed by using rapidly acquired Brillouin spectroscopic signatures as contrast. In an exemplary embodiment of the present invention, a pump or probe beam may be scanned laterally across the sample and spectral patterns from each region are recorded to create an image. Light can be scanned with various conventional scanners including, e.g., galvanometer-mounted mirrors, polygonal mirror scanners and/or MEMS mirrors. Another exemplary embodiment of the present invention can use a scanning mechanism located on a fiber-optic catheter or endoscope for an application to, for example, luminal organ imaging.

In principle, three independent parameters can be extracted by each collected spectrum and can serve as contrast mechanisms for imaging: Brillouin frequency shift (Eq. 3), Brillouin linewidth (Eq. 4), and Brillouin intensity (Eq. 5). All of these three properties can have peculiar signatures (e.g., elasticity, viscosity and electrostriction, respectively) of the sampled material. Thus, three separate images can be obtained, for example, using a false color lookup table, featuring such properties. Alternatively, the three pieces of information can be used simultaneously for higher accuracy, especially at the interfaces between two different materials. For example, at the borders of the objects, a non-trivial imaging processing procedure can be applied rather than a simple false-color lookup table. At the interfaces, Brillouin lines of both materials can be measured, proportionally to the amount of incident light that excites each particular material. Therefore, rather than relying on only one of the spectral signatures, the various Brillouin lines can be discriminated, and their total strength can be accurately quantified and compared to the strength that would be observed away from an interface.

FIG. 2 depicts a block diagram of an exemplary apparatus in accordance with exemplary embodiments of the present invention. The exemplary arrangement in FIG. 2 includes a light source 21 which can act as pump beam 23 and may be delivered to the sample 25 through a beam splitter 27, a beam scanner 29, and an objective lens 31. The scattered light 33 can be collected by the objective lens 31, which may be a first element of a microscope arrangement 35, to obtain spatially resolved information. Light can then be sent to a spectrometer 37 for spectral analysis and to a detector 39 to convert the optical information in electrical signals.

Possible light sources which may be used include, e.g., monochromatic lasers emitting a wavelength in the range of visible to infrared. The light source can employ an optical arrangement to deliver more than one frequency line. The linewidth of the laser may be typically less than about 1 MHz, which can provide temporal coherence longer than the lifetime of acoustic phonons. The scattered light 33 from a sample may include multiple frequency components originated from simple elastic scattering, as well as Brillouin scattering.

Exemplary applications for microscope implementation include, e.g., wide-field or confocal microscopy, dual-axis confocal microscopy (see T. D. Wang, M. J. Mandella, C. H.

Contag, and G. S. Kino, "Dual-axis confocal microscope for high-resolution in vivo imaging," *Optics Letters*, vol. 28, pp. 414-416, 2003) and/or fiber confocal microscopy. In an exemplary embodiment of the present invention, an epi-detection configuration may be used in which a backward-propagating Brillouin light 33 is collected by the same lens 31 used for illumination. Epi-detection can take advantage of an intrinsic property of Brillouin scattering, e.g., the scattered signal wave can be a phase conjugate to the pump wave. This property may enhance the collection efficiency of the Brillouin wave through a turbid medium such as tissue.

Exemplary focusing mechanisms are shown in FIG. 3. For coarse resolutions, a collimated pump beam with a relatively small beam diameter may be used. However, for three dimensional resolutions, the pump/probe beams can be focused to a sample by the use of objective lenses. In the exemplary configuration of FIG. 3A, objective lenses with low numerical aperture (NA) 51 can result in a low transverse resolution, but the longitudinal interaction length may be long and well-defined. In FIG. 3B, objective lenses 53 having a high NA may provide better transverse and axial resolution. Since the Brillouin interaction length can be short and the interaction can be made over a large solid angle, the phase matching condition may become less stringent. This condition can broaden the linewidth of the scattered light, thereby affecting the strength of Brillouin signal and the accuracy of the spectral analysis, as described in Danielme. Hg, "Aperture Corrections for Sound-Absorption Measurements with Light Scattering," *Journal of the Acoustical Society of America*, vol. 47, pp. 151-&, 1970.

More than one pump beam may be provided using multiple objective lenses. FIG. 4C depicts an exemplary embodiment of the present invention using two objective lenses 55, 57. This scheme, however, may not be suitable for in vivo biomedical applications. Confocal techniques can be used to enhance depth sectioning. For example, a dual-axis confocal configuration can maximize axial resolution for a given NA and at the same time allows a reduction of back-reflections and elastic scattering components. A fiber arrangement can also be used, for example, by having a single-mode fiber as confocal pinhole. Acting as tight spatial mode filter, the fiber can provide strict confocal imaging which may reduce the amount of stray or spurious unwanted radiation.

The requirements on spectral analysis for Brillouin spectroscopy can be stringent because 0.1 GHz to 50 GHz features may be resolved. High spectral resolution and rapid analysis can be essential to facilitate imaging capabilities as well as dynamic studies.

High resolution and simultaneously high sensitivity in the spectral analysis can be important. Fabry-Perot interferometry can be used for the spectral analysis of Brillouin signal in both scanning (see J. R. Sandercock, "Some Recent Developments in Brillouin-Scattering," *Rca Review*, vol. 36, pp. 89-107, 1975) and non-scanning configurations (as described in K. J. Koski, J. Muller, H. D. Hochheimer, and J. L. Yarger, "High pressure angle-dispersive Brillouin spectroscopy: A technique for determining acoustic velocities and attenuations in liquids and solids," *Review of Scientific Instruments*, vol. 73, pp. 1235-1241, 2002). Fabry-Perot scanning interferometers can have very high resolution. However, they can be intrinsically slow because they perform the spectral analysis in a sequential manner by measuring the energy of the various frequency components one at a time. Non-scanning (or angle-dispersive) Fabry-Perot interferometry may be faster because it can measure all frequency components at once in a parallel fashion using an array of detectors. However, angle-dispersive Fabry-Perot interferometry may also have intrinsic limitations in sensitivity as described below.

In angle-dispersive Fabry-Perot spectroscopy, the spectral separation can be determined by the interference of multiple reflections at two optical mirrors. Two interference patterns can be formed, one in transmission and one in reflection, but only the transmission pattern may be measured by the detecting device. All energy of the reflected interference pattern can be lost, thereby hindering the sensitivity of the spectrometer.

The maximum amount of light that may be forwarded to the detector in this configuration can be easily quantified. The resolution performance of spectrally dispersive elements can be characterized by a parameter known as finesse (f), which may be defined as a ratio of the separation between different orders of diffraction to the linewidth of an individual resolved line. The finesse f can be similar to the number of spectral components can be resolved; e.g., f=N. A higher finesse can correspond to a higher resolution of the spectral dispersive element.

However, in angle dispersive Fabry-Perot interferometry, for each frequency component that is discriminated in the transmitted pattern, a certain, proportional, amount of light may be lost in the reflected pattern. Thus, a higher finessecan correspond to a lower total light throughput. If f is the finesse of the angle-dispersive Fabry-Perot interferometer, then a maximum of 1/f of the input light can be sent to the detecting device. This is a limit which does not include other practical loss mechanisms. The 1/f throughput limit can be overcome by various other spectral dispersive elements such as, e.g., diffraction gratings or prisms, but such devices cannot provide the high resolution needed for Brillouin spectroscopy.

The simultaneous requirements of resolution and light throughput can be met by a fully parallel-detection spectroscopic technique. A preferred solution for such spectroscopy is shown in FIG. 4, which includes a diffractive tilted etalon 71, e.g., a virtually-imaged phased array (VIPA) (see M. Shirasaki, "Large angular dispersion by a virtually imaged phased array and its application to a wavelength demultiplexer," *Optics Letters*, vol. 21, pp. 366-368, 1996), in combination with an array-type detector such as a CCD camera. Light can be focused on the VIPA element 71 by a cylindrical lens 75 while light is collected from the VIPA 71 onto the CCD by another lens 77. The VIPA spectrometer can achieve high spectral resolution with high temporal resolution. As in angle-dispersive Fabry-Perot spectroscopy, the spectral selection can be provided by the interference of multiple reflections at two optical flats, yielding equivalent performances in terms of resolution. Unlike Fabry-Perot etalons, however, the first surface can be totally reflective but may be cut (or coated) to allow all the light to enter the interferometer. Besides minimizing losses, this design can avoid useful light being wasted in a reflected interference pattern. As a consequence, with respect to an equivalent Fabry-Perot spectrometer, the signal strength can be improved by a factor f equal to the finesse of the interferometer. Such improvement in light throughput of the spectrometer can allow real time monitoring of dynamical processes such as collagen cross-linking.

the exemplary VIPA spectrometer generally may have a limited resolution of about 1 GHz and a limited extinction efficiency of about 30 dB (1 over a thousand) and, as a result, may be effective only for optically transparent samples. In a turbid sample such as a biological tissue, elastic (Rayleigh) scattering can be several orders of magnitude stronger than Brillouin scattering and is separated by only a few GHz from Brillouin signal. For this reason, additional spectral selection may be preferable. Possible solutions include diffraction gratings, fiber Bragg gratings, or notch filters based on narrow absorption line of gas cells. Two further procedures may be used, e.g., a multiple VIPA spectrometer and a spatial-to-spectral VIPA notch filter.

FIG. 5 shows a schematic illustration of an exemplary embodiment of a tandem-VIPA spectrometer. The exemplary role of the first-stage VIPA 91 in this figure can be to provide spectral dispersion along a vertical axis. A lens 93 can transfer this vertically dispersed beam to the second stage VIPA 95. The second-stage VIPA can further disperse the beam, but along the horizontal direction. After the second stage, the tail of the Rayleigh spectrum, which had been overlapped with Brillouin peaks, may be separated from the Brillouin signals. The resulting spectrum can be imaged by a lens 97 onto a 2D CCD array 99 or a 1D array oriented at 45 degrees. A spatial mask may be placed to reject Rayleigh light and to prevent it from entering the second VIPA. The addition of the second VIPA may likely lead to an about 20-25 dB improvement of contrast suppression.

This approach can be extended further to three or more VIPA stages to improve contrast, but additional stages may increase optical loss. Besides the intrinsic losses of a VIPA, a single VIPA stage can produce multiple diffraction orders, but only one or a few of them may be transferable to another VIPA at the next stage. Even with optimal optical design, a total loss of 6 to 10 dB may result. These additional losses can be compensated by increasing CCD integration time or by spectrum averaging. Moreover, improving the extinction of the spectrometer greatly reduces the problem arising from the backscattered light, thereby allowing for more efficient collection procedures.

FIG. 6 shows an exemplary spatial-to-spectral VIPA notch filter that can be used to selectively attenuate Rayleigh light with respect to Brillouin light. For example, the output of the collection optical system 111 can enter a VIPA 113 and become spectrally separated. A spatial mask 115 can be placed at the back focal plane of an imaging lens 117 and may block the Rayleigh light. The rest of the spectrum can be reflected by a mirror 119 and combined by the same VIPA 113 to exit the device 121 unchanged, apart from being spectrally filtered. Combining a polarization beam splitter 123 and a quarter wave plate 125 can eliminate beam-splitting loss. An additional extinction efficiency of ~20 dB can be expected by such spectral notch filter.

For specific situations in which high spectral resolution and contrast are needed a scanning filter such as a Fabry-Perot interferometer can be used. The Fabry-Perot scanning interferometer may have a free spectral range of 50 GHz, and finesse of 1000; it can operate in single-pass configuration or in multipass, fixed or tandem, to enhance contrast. Alternatively, a fixed filter with a bandpass, notch, or edge type may be used, instead of a scanning filter, to measure the magnitude of certain frequency components. However, an optical frequency of the pump wave should be stabilized or locked with respect to the fixed filter.

Further exemplary embodiments of the present invention can be provided which combine exemplary embodiments described herein above with different spectral modalities. For example, once light is delivered to a material, the light collected from the sample can include various components arising from different phenomena which may carry independent information about the sample under study.

FIG. 7 shows an example of various components of such collected light separated by their frequency shift with respect to the incoming light. For example, reflected light 131, unshifted in frequency, can provide information about the structure of the sample as a standard reflectance confocal microscope might do. A Brillouin component 133 can provide mechanical information about the sample. Raman components 135 can arise from vibrational phonons of the analyzed material, and thus yield chemical information about its constituents. Fluorescence 137, either endogenous or induced by the introduction of fluorophores, can help identify particular elements in the material and can provide functional information about the sample under scrutiny. In addition, in Brillouin spectral region, Raman scattering arising from rotational degrees of freedom of the sample can be analyzed as well as Rayleigh-Wing scattering, a process related to the optical anisotropy of the material, e.g., the fluctuations in the orientation of its molecules. Reflectance, Raman and fluorescence spectroscopy can be used individually for imaging purposes, and a combination of two or more of such modalities may also be used.

In exemplary embodiments of the present invention, a combination of Brillouin microscopy with other modalities can be provided. An exemplary block diagram of such multi-modal microscopy via the simultaneous implementation of Brillouin as well as Raman and fluorescence spectroscopy is shown in FIG. 8. For example, fluorescence, Raman and Brillouin spectra can be in different regions of the electromagnetic spectrum after passing through the collection optics 151. Scattered and fluorescent light 153 can undergo a coarse spectral dispersion 155 to separate the Brillouin, reflectance and rotational Raman components 157 from the fluorescence and vibrational Raman beam components 159. Possible solutions for such coarse spectral dispersion can include, but are not limited to, gratings, dichroic mirrors and/or interferometric bandpass filters.

Beam 157, containing Brillouin reflectance and rotational Raman information, can be analyzed by a spectrometer 161 and a detector 162. Exemplary solutions for this analysis can include various spectrometers as described herein above. Beam 159, containing fluorescence and Raman scattering, can be further spectrally separated by a dispersive element 163, whose exemplary implementations are gratings, bandpass filters, prisms or other conventional spectral dividing methods. The fluorescence beam 165 is collected and measured by a detector 167; the vibrational Raman component 169 is collected and measured by a detector 171. Exemplary solutions for detectors 169, 171, 162 include, but are not limited to, photomultiplier tubes or photodiodes, or they can be combined in a single array detector such as, e.g., a CCD camera. Such detectors can allow delivery of Raman, Brillouin and fluorescent information simultaneously to the same computer 173.

This multi-modality technique and apparatus can be particularly advantageous because, as previously stated, the various processes can be used to sample independent and diverse characteristics of a given material, thus yielding mechanical as well as optical and/or chemical information about the analyzed sample.

FIG. 9 is a schematic diagram of a prototype instrument according to an exemplary embodiment of the present invention. Such instrument includes a light source, imaging optics, a spectrometer, and a computer. The light source is a frequency-doubled diode-pumped Nd—YAG laser emitting, e.g., a 532-nm wavelength with a linewidth of 1 MHz (Laser Quantum, Inc.) Light is focused on a sample through a 30 mm focal length lens. A dual-axis confocal geometry with a free-space entrance angle of about 6 degrees was chosen to minimize back-reflections and achieve higher sectioning capabilities with low numerical apertures (0.03). Scattered light is collected through the same lens. A single mode fiber is then used as confocal pinhole. This allows for strict confocal imaging because the fiber is effectively a single-mode spatial filter, thus it minimizes stray light. The output of the fiber is spectrally filtered by a 3 nm bandpass filter, mainly to avoid fluorescence from the samples. Light is then coupled into the VIPA spectrometer for high spatial separation of the spectral components in the plane of an Electron-Multiplied CCD camera. The optical design of the spectrometer, with the combination of input cylindrical lens before the VIPA and spherical lens after the VIPA as well as CCD binning, can maximize the SNR of the setup by achieving one-dimensional spectral dispersion. According to one exemplary embodiment of the present invention, it is possible to utilize a number of types of VIPA, e.g., (a) a custom-built 3-mm solid etalon made of fused silica, as shown in FIG. 4, with coatings of about R1=99.9%; about R2=95%, about FSR=33 GHz and finesses between about 40 and 60; and (b) a home-built air-spaced VIPA which can include two mirrors (e.g., R1=99.9%; R2=95%), variable FSR between about 1 and 40 GHz and finesses between about 10 and 20. The exemplary total light throughput of an exemplary VIPA spectrometer can be as high as 75%.

Figure 10A:
FIG. 10A is an illustration of an exemplary CCD pixel index in accordance with exemplary embodiments of the present invention.
Figure 10B:
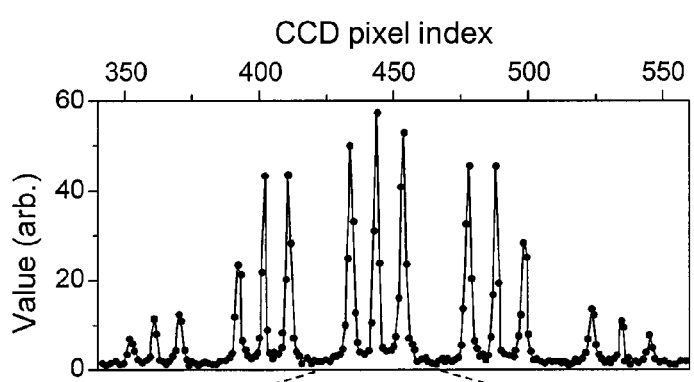
FIG. 10B is an exemplary analysis of spectral measurement of the index shown in FIG. 10A.
Figure 10C:
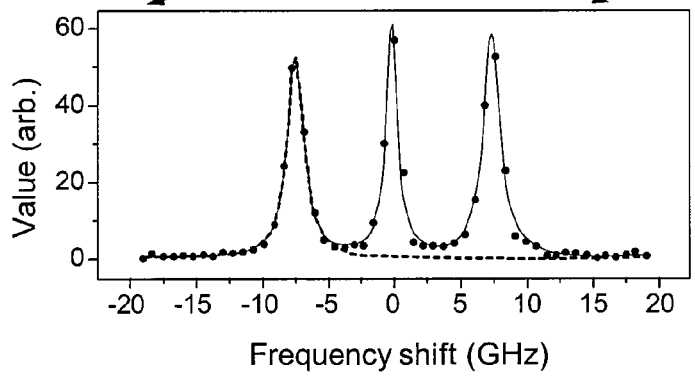
FIG. 10C is an illustration of an expanded view of a portion of the exemplary analysis of spectral measurement shown in FIG. 10B.

A typical spectrum recorded from water in 1 s under 10 mW of illumination power is shown in FIGS. 10A-10C. Several diffraction orders are visible in the CCD retrieved image shown in FIG. 10A. FIG. 10B shows the central peak in each order, which can correspond to the elastic Rayleigh scattering, and the ancillary peaks on the right and on the left which can correspond to Stokes and anti-Stokes components of Brillouin scattering. The acquired spectrum can be mapped onto an actual frequency scale as shown, e.g., in FIG. 10C, to allow for the evaluation of Brillouin frequency shift and linewidth.

Figure 11:
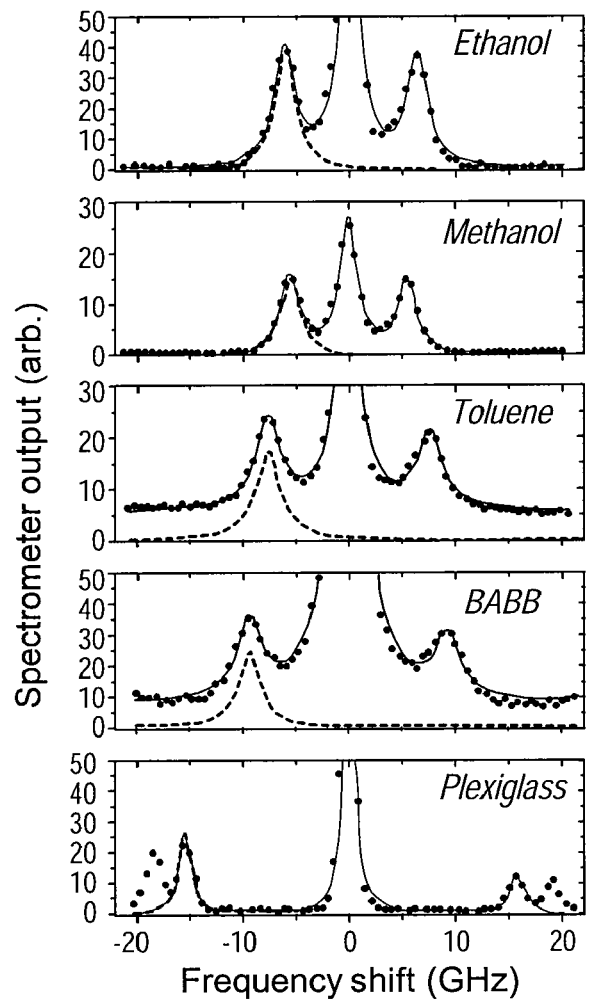
FIG. 11 is a further exemplary analysis of a spectral measurement in accordance with exemplary embodiments of the present invention.

Several spectra acquired from different materials using this prototype instrument are shown in FIG. 11. Among the various samples examined, BaBb (2:1 solution of Benzene and Benzyl alcohol) may be particularly relevant for future biological studies because it is a clearing agent widely used to achieve optical transparency in numerous biological samples. The experimental data (dots) are fitted to a triplet of Lorentzian functions (solid line) while a fit of the single Stokes Brillouin line is shown by the dashed lines. Plexiglas has a Brillouin shift very close to half the FSR of the spectrometer. Thus, Brillouin peaks from neighbor orders may also be visible. The graphs shown in FIG. 11 suggest that some materials, e.g., Toluene and BaBB, can exhibit a measurable background arising from Rayleigh-wing scattering. The measured spectral width of Rayleigh-wing scattering in Toluene (8 cm$^{-1}$) is consistent with previously observed data, as described in K. J. Koski, J. Muller, H. D. Hochheimer, and J. L. Yarger, "High pressure angle-dispersive Brillouin spectroscopy: A technique for determining acoustic velocities and attenuations in liquids and solids," *Review of Scientific Instruments*, vol. 73, pp. 1235-1241, 2002. Acquiring several spectra from different known materials can be used to calibrate spectral separations with respect to the actually observed spatial discrimination of different peaks, as described in the K. J. Koski reference. A linear relationship can be observed between measured pixel separation and literature data on Brillouin frequency shifts. Using the slope of such curves, the spectrometer can be calibrated. With such calibration, the Brillouin analysis on elasticity and viscosity retrieval can exhibit agreement with reported values. as described in the H. Z. Cummins and R. W. Gammon reference, the K. J. Koski reference, and G. W. Faris, L. E. Jusinski, and A. P. Hickman, "High-Resolution Stimulated Brillouin Gain Spectroscopy in Glasses and Crystals," *Journal of the Optical Society of America B-Optical Physics*, vol. 10, pp. 587-599, 1993

Figure 12:
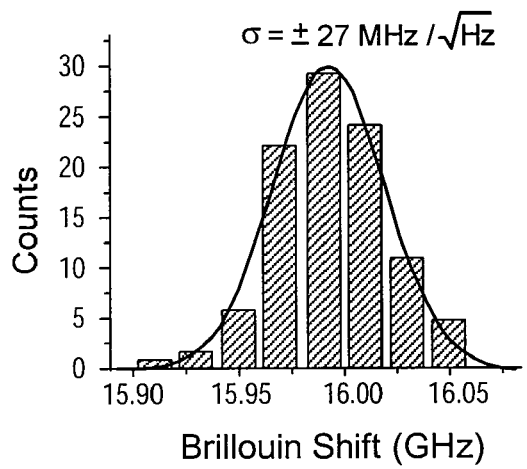
FIG. 12 is an exemplary graph showing stability of a spectral analysis.

FIG. 12 shows a histogram of the occurrence of retrieved shifts as recorded over time from the same sample in the same experimental condition. This histogram thereby indicates the stability of Brillouin spectral analysis. The material used for this measurement is cured, fully solid, epoxy resin. Based on the histogram, the sensitivity of the instrument in the frequency (and thus elasticity) evaluation can be estimated (in this case, e.g., the sensitivity is about 20 MPa/$\sqrt{Hz}$).

Rapid data acquisition achievable by parallel detection can be critical for following dynamic processes that may change the elastic properties of materials in real time. Such a capability is shown in FIG. 13 with respect to a UV curable epoxy resin sample. A UV lamp was used for this measurement, characterized by an output of 90 mW/cm$^2$ in the 300 nm-400 nm wavelength range, and placed 8 cm away from the sample. At time t=0, a UV lamp was turned on to begin curing the resin. The measurement of Brillouin shifts over time reveals rapid changes under UV light as well as a slow curing process afterward. No curing effect was observed based on the incident green light, as suggested by the Brillouin signatures for t<0. The elastic modulus changed from 4.5 GPa when uncured to 9 GPa after fully cured over 1 day.

No previous data was available for comparison to such observations. However, the experimental result corresponds to the expected time-dependent curing process, because UV curing can induce crosslinking in a polymer adhesive and thereby increase its modulus. This experiment demonstrates the capability of exemplary embodiments of the present invention to monitor mechanical changes associated with crosslinking of a polymer with a high sensitivity (e.g., 40 MPa/$\sqrt{Hz}$) and a high temporal resolution (e.g., about 1 sec).

Three-dimensional Brillouin microscopy can be achieved using exemplary embodiments of the present invention that include a confocal arrangement. For imaging, Brillouin spectra can be acquired continuously as the sample is translated with respect to the beam focus. The spatial resolution of an exemplary confocal apparatus was observed to be about 6 μm in a transverse direction and 60 μm in an axial direction. Resolution measurements were obtained by recording Brillouin frequency shifts at the interface of two materials by over-sampling the acquisition data to a much smaller step than the actual resolution. At the interface of two materials, Brillouin signatures from both materials were observed, having different strengths depending on the amount of light that is shining onto a particular material. A meaningful parameter retrieved for such measurement can be a ratio between Brillouin signal amplitudes in the two frequency regimes that correspond to the two different materials.

To demonstrate cross-sectional imaging, an intraocular polymer lens, e.g., a popular biomedical implant used to replace a human crystalline lens, was used as a sample. The intra-ocular lens is made of acrylate-methacrylate copolymer with bonded UV absorber and blue-light filtering chromophore (transmission of about 90% at 532 nm) to mimic the performance of human lenses. To minimize backscattering and back-reflections, the intraocular lens was placed in a bath of epoxy resin of similar refractive index, inside a plastic cuvette, and the sample was slightly tilted with respect to the optical axis as shown in FIG. 14A. Such tilting can be seen by analyzing the processed image of the lens in FIGS. 14B and 14C. To expedite the image acquisition and avoid unwanted curing effects in the resin, all the data of this experimental run were taken with 3.5 mW of illuminating power and 0.5 seconds of exposure time.

FIGS. 14B and 14C depict exemplary processed cross sectional images of an x-z plane of the lens. In FIG. 14B, Brillouin frequency shifts are color mapped vs. spatial position inside the sample. In FIG. 14C, the normalized Brillouin signal amplitude at a given frequency shift is color mapped vs. spatial position. As suggested by Eq. (5), Brillouin amplitude, which can be related to a material coupling of acoustic and optical energy, may be peculiar to each medium and can be used as additional signature for material discrimination. The biconvex shape of the lens can be distinguished in these images, as well as small dust particles on the lens surface and the plastic cuvette in the top left corner.

Figure 15:
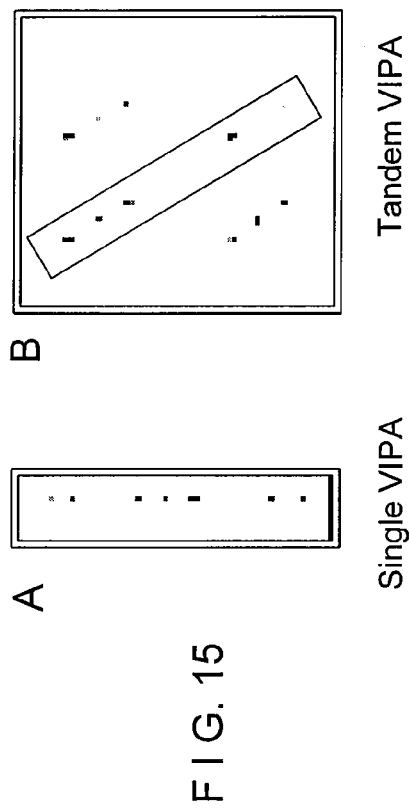
FIG. 15A is an illustration of an exemplary Brillouin spectrum collected with a single-VIPA spectrometer in accordance with exemplary embodiments of the present invention.
FIG. 15B is an illustration of an exemplary Brillouin spectrum collected with a tandem VIPA spectrometer in accordance with exemplary embodiments of the present invention.

Certain previous exemplary data have been collected with a single VIPA spectrometer. Thus, such data may be limited to optical transparent samples. According to one exemplary embodiment of the present invention, by using an exemplary tandem VIPA spectrometer, the extinction can be improved significantly and therefore more scattering samples can be analyzed. FIGS. 15A-15C show exemplary acquired Brillouin spectrum for Methanol using a single (see FIG. 15A) vs a tandem (see FIG. 15B) VIPA spectrometer featuring substantially two identical VIPAs with FSR=about 33 GHz and nominal coating reflectivities of about 99.9% and 95%. At half FSR, the extinction for a single VIPA spectrometer can be estimated to be about 34 dB, with one for a tandem VIPA spectrometer possibly approaching about 59 dB. The total throughput of a tandem VIPA spectrometer can typically be about 50%.

Figure 16:
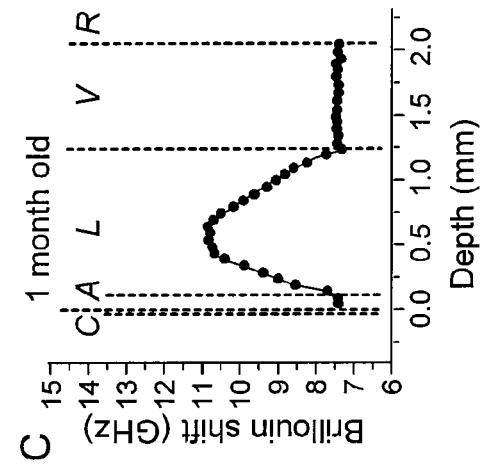
FIG. 16A is an illustration of the anatomy of a murine eyeball which was imaged in accordance with exemplary embodiments of the present invention.
FIG. 16B is a first exemplary measurement showing the depth profile of elasticity of a mouse eyeball measured in vivo in accordance with exemplary embodiments of the present invention.
FIG. 16C is a second exemplary measurement showing the depth profile of elasticity of a mouse eyeball measured in vivo in accordance with exemplary embodiments of the present invention.
Figure 16:
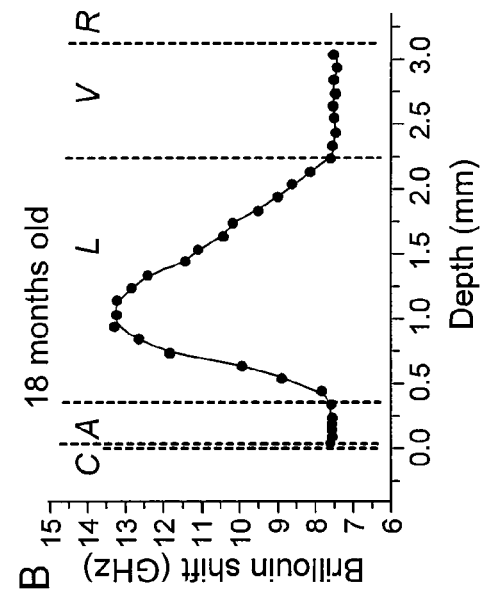
Figure 16:
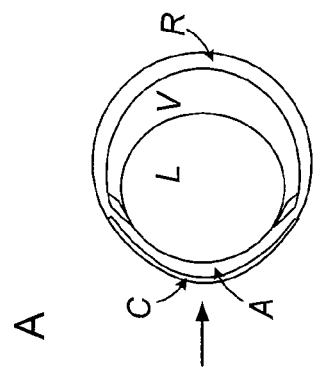

Using an exemplary tandem VIPA spectrometer, it may be possible to measure, e.g., the Brillouin signature from crystalline lens of a mouse eye in vivo. FIG. 16A depicts the exemplary geometry of the measurement and the exemplary anatomy of the murine eyeball. For example, a coverslip may be placed on the anterior surface of the cornea with methylcellulose to minimize the corneal refraction. The laser beam may enter the crystalline lens through the center of the pupil. It is possible to acquire Brillouin spectra along the optic axis of the eye, e.g., at a depth interval of about 100 µm, with approximately 5-mW optical power and about 3-s integration time. FIG. 16B depicts the exemplary measured Brillouin frequency shift in an 18-month-old C57BL/6 mouse. For example, the Brillouin shifts of the aqueous and vitreous humors may be close to the one typical of distilled water. In the crystalline lens, the Brillouin shift can increase from the outer layers (cortices) toward the center (nucleus). This exemplary result may be consistent with previous measurements of excised lenses in vitro (see Ref. [1]), obtained using a multipass F-P scanning interferometer with higher power levels of about 10-25 mW and a longer integration time of about 10 min per spectrum. FIG. 16C depicts a similar measurement as that performed shown in FIG. 16B except that it was performed on a 1-month-old C57BL/6 mouse. The basic features of the measurement remain mostly the same, other than the physiological enlargement of the physical size of the eye. However, the stiffness of the crystalline lens is likely remarkably higher in the older mouse. This measurement likely indicates the ability of our instrument to detect changes in the mechanical properties of crystalline lenses with age, and illustrates the likely use of the exemplary embodiments of the present invention, e.g., for ophthalmology studies related for example to presbyopia, cataracts, refractive surgery, etc.

Based on such exemplary data, Brillouin Microscopy can be used as a preferable non-invasive diagnostic tool in, e.g., ophthalmology for early diagnosis, treatment evaluation and scientific understanding of ocular diseases such as presbyopia and cataracts. The exemplary embodiments of the present invention can also be used for various other applications, including and not limited to, e.g., auxiliary instruments for surgical treatments of cataracts, to monitor the procedure and/or evaluate pre- and post-surgical biomechanical signatures.

Exemplary embodiments of the present invention can be used in a variety of fields other than ophthalmology, as indicated by the preliminary exemplary data obtained using the exemplary embodiment of the system described herein above. One such exemplary application may be, e.g., to follow real-time dynamical changes of mechanical properties of a material which can occur, e.g., in tissue engineering.

For instance, injury to articular cartilage is a common orthopedic problem, with more than one million surgical procedures being performed in the United States each year. Tissue engineering offers new strategies for repairing cartilage, for example, by using chondrocytes and scaffolds to promote a formation of new cartilage matrix that closely resembles native tissue. Cartilage has an important biomechanical function. Consequently, the biomechanical properties of a scaffold and the micromechanical environment it provides for the implanted cells can play a significant role in cartilage repair. Although conventional mechanical testing techniques are widely used for such scaffolds, they can be invasive, time consuming, and difficult to use in situ and in vivo.

Figure 17:
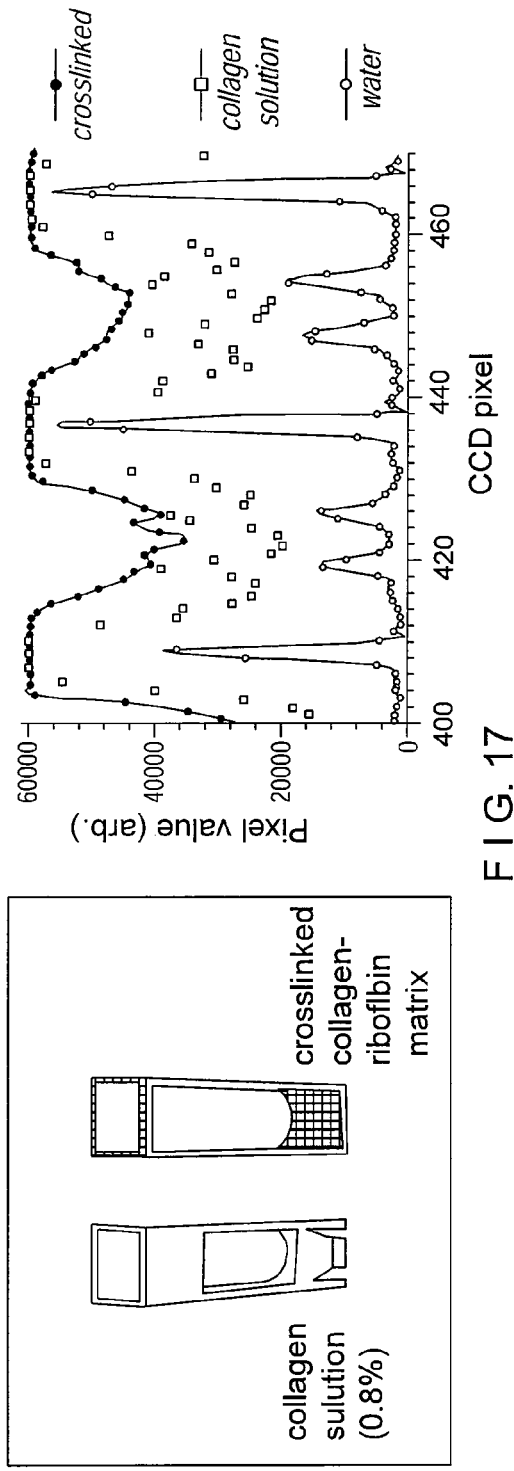
FIG. 17 is an illustration of exemplary collagen samples and their corresponding Brillouin signatures determined in accordance with exemplary embodiments of the present invention.

Exemplary embodiments of the present invention may facilitate more sophisticated studies and uses, such as characterizing the micromechanical environment of implanted chondrocytes and their effects on new cartilage formation in vivo and over time. In order to assess the feasibility of applying dynamic visco-elastic characterization for such cartilage formation, Brillouin spectra of a type-I collagen gel (0.8 wt %) in 0.02N acetic acid solution and a photochemically cross-linked collagen-riboflavin mixture were measured. FIG. 17 shows exemplary measured Brillouin spectra. The large peaks centered at CCD pixel numbers 409, 437, and 465 correspond to elastic Rayleigh scattering, whereas other peaks in between originated from inelastic Brillouin scattering. Rayleigh scattering in the collagen solution was substantially stronger than that in water, producing larger background under the Brillouin peaks. Nevertheless, well-defined Brillouin peaks are observed with Brillouin shifts nearly the same as that of water, consistent with the high water content (~99%) in the gel. Additional peaks at a shift of about 3.5 GHz are also observed, although it may not be clear what these peaks represent. Mixing collagen gel with riboflavin further increased the Rayleigh peak (data not shown).

Crosslinking of the gel was induced by illuminating with blue light for 40 sec. After crosslinking, strong Rayleigh scattering, appreciable even with the naked eye, was observed to dominate nearly the entire spectral window, which may prohibit an accurate detection of Brillouin peaks.

Figure 18:
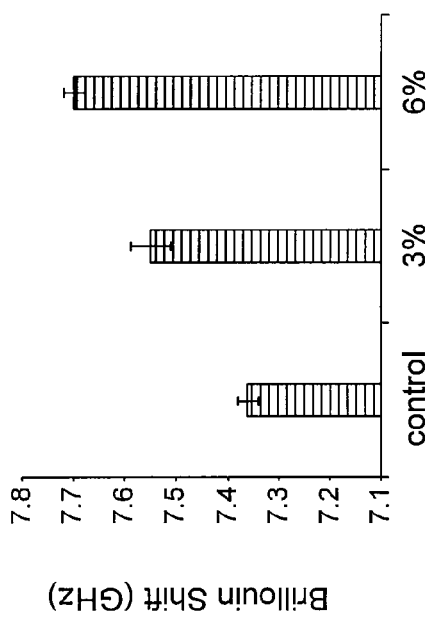
FIG. 18 is an exemplary measurement of different Brillouin signatures for different concentration of collagen samples and different degrees of collagen cross-linking determined in accordance with exemplary embodiments of the present invention.

A tandem VIPA spectrometer may have a certain amount of a extinction to measure collagen cross-linking. In order to demonstrate this ability, it is possible to prepare two acidic solutions with about 3% and 6% collagen, and measure their Brillouin signatures with and without crosslinking. In this exemplary case, it may be preferable to use, e.g., Rose Bengal as a photo sensitizer; and the curing may occur with, e.g., 532 nm laser light. FIG. 18 depicts the exemplary results of this measurement. For example, 50 measurements with 10 mW illumination power and 2 seconds exposure may be preformed for each sample. As shown in FIG. 18, the exemplary embodiment of the apparatus according to the present invention is able to discriminate between, e.g., the control (non-cross-linked sample) and the cross-linked ones. In addition, a distinction can be seen between the 3% and the 6% solution, e.g., showing enough sensitivity of the exemplary instrument to discriminate different tissue engineering compounds.

Based on this exemplary data, Brillouin microscopy may be useful, e.g., in reviewing and determining the mechanical properties and their effects on chondrocytes-encapsulated collagen scaffolds and neocartilage formation in vitro as well as in vivo. Exemplary embodiments of the present invention may further be used to characterize living cells and tissues. However, stronger Rayleigh scattering arises in cells and tissue. An additional Rayleigh rejection efficiency of about 20-25 dB can be sufficient for tissue studies. Exemplary data may indicate that triple-VIPA spectrometer can be sufficient to achieve such exemplary task. Thus, Brillouin microscopy may be applied to biological tissues successfully. Water has a bulk modulus, E, of about 2.2 GPa at room temperature and a density, $\rho$, of about 1 g/cm$^3$. Thus, e.g., at $\lambda$=532 nm, n=1.33, and $\theta$=0°, and $\Delta\nu$=7.5 GHz. Since water is the most abundant molecule in biological tissue, studies show that biological tissue can exhibit Brillouin shifts in a range of about 2-20 GHz at $\lambda$=532 nm, as described in the J. M. Vaughan and J. T. Randall publication and the R. Harley, D. James, A. Miller, and J. W. White publication. Most biopolymers, such as PMMA or acrylate polymer, have Brillouin shifts also in the GHz range. Non-isotropic samples such as muscle or collagen fibers can produce multiple Brillouin shifts, which may depend on the scattering direction with respect to their symmetry axes, as described in N. Berovic, N. Thomas, R. A. Thornhill, and J. M. Vaughan, "Observation of Brillouin-Scattering from Single Muscle-Fibers," *European Biophysics Journal with Biophysics Letters*, vol. 17, pp. 69-74, 1989.

The energy of an acoustic wave involved in spontaneous Brillouin scattering may be too weak to cause any significant biological perturbation. The Young's modulus and damping coefficient of a viscoelastic sample may be frequency dependent. Thus, such parameters measured by Brillouin spectroscopy in the GHz frequency range may be different from those measured by conventional strain-stress test or dynamic mechanical analysis, which may be typically performed from 0 Hz (e.g., using DC signals) to 100 Hz, as described in R. L. Y. Sah, Y. J. Kim, J. Y. H. Doong, A. J. Grodzinsky, A. H. K. Plaas, and J. D. Sandy, "Biosynthetic Response of Cartilage Explants to Dynamic Compression," *Journal of Orthopaedic Research*, vol. 7, pp. 619-636, 1989. Most biological tissue and biopolymers can be viscoelastic and, consequently, the elasticity may vary considerably with strain rate and temperature. Therefore, it can be important to establish a correlation between Brillouin measurements and conventional mechanical measurements. In contrast, water has a very rapid relaxation time, shorter than about 10 ps, so its elastic modulus may not vary much from 0 Hz to 10 GHz.

Measuring viscoelastic properties of living tissues using Brillouin microscopy can provide a useful clinical non-invasive tool for the detection of early-stage cancers or intraoperative determination of tumor margins. Tumors may be generally stiffer than surrounding healthy tissue, and a Brillouin spectrum of a tumor can thereby exhibit a stronger magnitude than normal tissues at high frequencies. Atherosclerosis is another medical area the Brillouin microscopy may be used for characterizing stress and tissue compliance, e.g., to help identify plaques which may be at risk for causing an acute coronary event.

The foregoing merely illustrates the principles of the invention. Various modifications and alterations to the described embodiments will be apparent to those skilled in the art in view of the teachings herein. Indeed, the arrangements, systems and methods according to the exemplary embodiments of the present invention can be used with any OCT system, OFDI system or other imaging systems, and for example with those described in U.S. Provisional Patent Appn. No. 60/514,769 filed Oct. 27, 2003, and International Patent Application No. PCT/US03/02349 filed on Jan. 24, 2003, the disclosures of which are incorporated by reference herein in their entireties. It will thus be appreciated that those skilled in the art will be able to devise numerous systems, arrangements and methods which, although not explicitly shown or described herein, embody the principles of the invention and are thus within the spirit and scope of the present invention. In addition, to the extent that the prior art knowledge has not been explicitly incorporated by reference herein above, it is explicitly being incorporated herein in its entirety. All publications referenced herein above are incorporated herein by reference in their entireties. Exemplary references cited herein are as follows:

[1] J. M. Vaughan and J. T. Randall, "Brillouin-Scattering, Density and Elastic Properties of the Lens and Cornea of the Eye," Nature, vol. 284, pp. 489-491, 1980.

[2] R. Harley, D. James, A. Miller, and J. W. White, "Phonons and Elastic-Moduli of Collagen and Muscle," Nature, vol. 267, pp. 285-287, 1977.

[3] J. Randall and J. M. Vaughan, "Brillouin-Scattering in Systems of Biological Significance," Philosophical Transactions of the Royal Society of London Series a-Mathematical Physical and Engineering Sciences, vol. 293, pp. 341-348, 1979.

[4] H. Z. Cummins and R. W. Gammon, "Rayleigh and Brillouin Scattering in Liquids—Landau-Placzek Ratio," Journal of Chemical Physics, vol. 44, pp. 2785-&, 1966.

[5] T. Sonehara and H. Tanaka, "Forced Brillouin Spectroscopy Using Frequency-Tunable Continuous-Wave Lasers," Physical Review Letters, vol. 75, pp. 4234-4237, 1995.

[6] R. Loudon, "Theory of Surface-Ripple Brillouin-Scattering by Solids," Physical Review Letters, vol. 40, pp. 581-583, 1978.

[7] H. S. Lim, M. H. Kuok, S. C. Ng, and Z. K. Wang, "Brillouin observation of bulk and confined acoustic waves in silica microspheres," Applied Physics Letters, vol. 84, pp. 4182-4184, 2004.

[8] T. D. Wang, M. J. Mandella, C. H. Contag, and G. S. Kino, "Dual-axis confocal microscope for high-resolution in vivo imaging," Optics Letters, vol. 28, pp. 414-416, 2003.

[9] Danielme. Hg, "Aperture Corrections for Sound-Absorption Measurements with Light Scattering," Journal of the Acoustical Society of America, vol. 47, pp. 151-&, 1970.

[10] J. R. Sandercock, "Some Recent Developments in Brillouin-Scattering," Rca Review, vol. 36, pp. 89-107, 1975.

[11] K. J. Koski, J. Muller, H. D. Hochheimer, and J. L. Yarger, "High pressure angle-dispersive Brillouin spectroscopy: A technique for determining acoustic velocities and attenuations in liquids and solids," Review of Scientific Instruments, vol. 73, pp. 1235-1241, 2002.

[12] M. Shirasaki, "Large angular dispersion by a virtually imaged phased array and its application to a wavelength demultiplexer," Optics Letters, vol. 21, pp. 366-368, 1996.

[13] H. Tanaka and T. Sonehara, "New Method of Superheterodyne Light Beating Spectroscopy for Brillouin-Scattering Using Frequency-Tunable Lasers," Physical Review Letters, vol. 74, pp. 1609-1612, 1995.

[14] G. W. Faris, L. E. Jusinski, and A. P. Hickman, "High-Resolution Stimulated Brillouin Gain Spectroscopy in Glasses and Crystals," Journal of the Optical Society of America B-Optical Physics, vol. 10, pp. 587-599, 1993.

[15] N. Berovic, N. Thomas, R. A. Thornhill, and J. M. Vaughan, "Observation of Brillouin-Scattering from Single Muscle-Fibers," European Biophysics Journal with Biophysics Letters, vol. 17, pp. 69-74, 1989.

[16] R. L. Y. Sah, Y. J. Kim, J. Y. H. Doong, A. J. Grodzinsky, A. H. K. Plaas, and J. D. Sandy, "Biosynthetic Response of Cartilage Explants to Dynamic Compression," Journal of Orthopaedic Research, vol. 7, pp. 619-636, 1989.

What is claimed is:

1. An apparatus comprising:
   at least one first arrangement configured to receive at least one first electro-magnetic radiation provided from a sample which is based on at least one second electro-magnetic radiation forwarded to the sample, wherein the at least one first electro-magnetic radiation has a first frequency and the at least one second electro-magnetic radiation has a second frequency which is different from the first frequency, and wherein a difference between the first and second frequencies is based on an acoustic wave inside the sample related to at least one characteristic of the sample;
   at least one second arrangement configured to receive at least one third electro-magnetic radiation from the at least one first arrangement which is based on the at least one first electro-magnetic radiation and separate the at least one third electro-magnetic radiation into a particular finite number (N) of frequency component radiations; and
   at least one third arrangement configured to receive a particular energy of more than 1/N of energy of the at least one third electro-magnetic radiation, and generate information associated with the sample.

2. The apparatus according to claim 1, wherein the at least one third arrangement is configured to receive the particular energy of at least one particular radiation of the frequency component radiations.

3. The apparatus according to claim 1, wherein the at least one third arrangement includes an array of detectors.

4. The apparatus according to claim 1, wherein the at least one second arrangement includes a virtually imaged phased array.

5. The apparatus according to claim 1, wherein the particular number is between about 10 and 100.

6. The apparatus according to claim 1, wherein the at least one third arrangement is configured to simultaneously receive a plurality of the frequency component radiations.

7. The apparatus according to claim 1, wherein the at least one first arrangement includes a narrow-band spectral filter arrangement which receives the at least one first electro-magnetic radiation and attenuates at least one portion thereof which has a frequency which is approximately the same as the second frequency.

8. The apparatus according to claim 1, wherein the at least one first arrangement includes a single-mode optical fiber arrangement.

9. The apparatus according to claim 1, wherein the at least one first arrangement includes a confocal arrangement.

10. The apparatus according to claim 1, wherein a resolvable linewidth of at least one frequency component radiation is less than 2 GHz.

11. The apparatus according to claim 1, further comprising at least one fourth arrangement configured to image the at least one portion of the sample based on the information.

12. The apparatus according to claim 11, wherein the information includes a difference between a frequency of at least one of the frequency component radiations and the second frequency.

13. The apparatus according to claim 12, wherein the difference is between approximately −100 GHz and +100 GHz.

14. The apparatus according to claim 11, wherein the information includes an energy of each of the frequency component radiations.

15. The apparatus according to claim 11, wherein the information includes a linewidth of a plurality of the frequency component radiations each of which being associated with a particular frequency.

16. The apparatus according to claim 11, wherein the information includes at least one characteristic of the sample.

17. The apparatus according to claim 16, wherein the at least one characteristic includes at least one bio-mechanical property of the sample.

18. The apparatus according to claim 17, wherein the at least one bio-mechanical property includes complex viscoelastic modulus.

19. The apparatus according to claim 16, wherein the at least one characteristic includes a crosslinking of collagen in the sample.

20. The apparatus according to claim 11, wherein the sample includes at least one of an anatomical structure or a biomaterial.

21. The apparatus according to claim 1, further comprising at least one fifth arrangement configured to deliver the at least one second electro-magnetic radiation to the sample.

22. The apparatus according to claim 21, wherein the at least one fifth arrangement scans the sample by moving the at least one second electro-magnetic radiation across the sample.

23. The apparatus according to claim 21, wherein the at least one fifth arrangement includes a fiber optic arrangement.

24. An apparatus comprising:
   at least one first arrangement configured to receive at least one first electro-magnetic radiation and at least one second electro-magnetic radiation provided from a sample, wherein the first and second electro-magnetic radiations which are based on at least one third electro-magnetic radiation forwarded to the sample, wherein the at least one first electro-magnetic radiation has a first frequency, the at least one second electro-magnetic radiation has a second frequency and the at least one third electro-magnetic radiation has a third frequency which is different from the first frequency, wherein a difference between the first and third frequencies is based on an acoustic wave inside the sample related to at least one characteristic of the sample, wherein the at least one first arrangement is further configured to separate the first and second electro-magnetic radiations into first and second respective frequency component radiations; and
   at least one second arrangement configured to simultaneously detect the first and second frequency component radiations, and generate information associated with the sample based on the first and second frequency component radiations.

25. The apparatus according to claim 24, wherein the at least one second electro-magnetic radiation is based on at least one of an elastic scattering, a vibrational Raman scattering or a fluorescence within the sample.

26. The apparatus according to claim 24, wherein the difference between the at least one first frequency and the at least one third frequency is greater than 10 THz.

27. The apparatus according to claim 24, further comprising at least one third arrangement configured to image the at least one portion of the sample based on the information.

28. The apparatus according to claim 24, wherein the at least one first arrangement includes a narrow band spectral separating arrangement for separating the at least one first electro-magnetic radiation, and a broadband spectral separating arrangement for separating the at least one second electro-magnetic radiation.

29. A method comprising:
receiving at least one first electro-magnetic radiation provided from a sample which is based on at least one second electro-magnetic radiation forwarded to the sample, wherein the at least one first electro-magnetic radiation has a first frequency and the at least one second electro-magnetic radiation has a second frequency which is different from the first frequency, and wherein a difference between the first and second frequencies is based on an acoustic wave inside the sample related to at least one characteristic of the sample;
receiving at least one third electro-magnetic radiation which is based on the at least one first electro-magnetic radiation and separate the at least one third electro-magnetic radiation into a particular finite number (N) of frequency component radiations;
receiving a particular energy of more than 1/N of energy of the at least one third electro-magnetic radiation; and
generating information associated with the sample.

30. A method comprising:
receiving at least one first electro-magnetic radiation and at least one second electro-magnetic radiation provided from a sample, wherein the first and second electro-magnetic radiations which are based on at least one third electro-magnetic radiation forwarded to the sample, wherein the at least one first electro-magnetic radiation has a first frequency, the at least one second electro-magnetic radiation has a second frequency and the at least one third electro-magnetic radiation has a third frequency which is different from the first frequency, and wherein a difference between the first and third frequencies is based on an acoustic wave inside the sample related to at least one characteristic of the sample;
separating the first and second electro-magnetic radiations into first and second respective frequency component radiations; and
simultaneously detecting the first and second frequency component radiations, and generate information associated with the sample based on the first and second frequency component radiations.

* * * * *